(12) United States Patent
Miller et al.

(10) Patent No.: US 10,919,888 B2
(45) Date of Patent: *Feb. 16, 2021

(54) BENZYL AMINE-CONTAINING HETEROCYCLIC COMPOUNDS AND COMPOSITIONS USEFUL AGAINST MYCOBACTERIAL INFECTION

(71) Applicant: UNIVERSITY OF NOTRE DAME DU LAC, South Bend, IN (US)

(72) Inventors: Marvin J. Miller, South Bend, IN (US); Garrett C. Moraski, Bozeman, MT (US)

(73) Assignee: UNIVERSITY OF NOTRE DAME DU LAC, South Bend, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/760,939

(22) PCT Filed: Sep. 19, 2016

(86) PCT No.: PCT/US2016/052558
§ 371 (c)(1),
(2) Date: Mar. 16, 2018

(87) PCT Pub. No.: WO2017/049321
PCT Pub. Date: Mar. 23, 2017

(65) Prior Publication Data
US 2018/0265506 A1    Sep. 20, 2018

Related U.S. Application Data

(60) Provisional application No. 62/220,192, filed on Sep. 17, 2015.

(51) Int. Cl.
*C07D 471/04* (2006.01)
*C07D 513/04* (2006.01)
*A61P 31/00* (2006.01)

(52) U.S. Cl.
CPC .......... *C07D 471/04* (2013.01); *A61P 31/00* (2018.01); *C07D 513/04* (2013.01)

(58) Field of Classification Search
CPC ...... A61P 31/00; C07D 471/04; C07D 513/04
See application file for complete search history.

(56) References Cited

U.S. PATENT DOCUMENTS

| | | | |
|---|---|---|---|
| 4,492,695 A | 1/1985 | Kaplan | |
| 4,891,371 A | 1/1990 | George | |
| 5,464,843 A | 11/1995 | Hansen, Jr. | |
| 5,721,273 A | 2/1998 | Sallee | |
| 6,080,767 A | 6/2000 | Klein | |
| 6,323,227 B1 | 11/2001 | Klein | |
| 6,379,649 B1 | 4/2002 | Katsifis et al. | |
| 6,403,588 B1 | 6/2002 | Hayakawa | |
| 6,552,037 B2 | 4/2003 | Cai | |
| 7,345,055 B2 | 3/2008 | Oberboersch | |
| 7,566,781 B2 | 7/2009 | Sakuraba | |
| 7,829,568 B2 | 11/2010 | Frank et al. | |
| 8,198,449 B2 | 6/2012 | Pracitto | |
| 8,293,909 B2 | 10/2012 | Pracitto | |
| 9,278,968 B2* | 3/2016 | Kurosaki | C07D 471/04 |
| 9,309,238 B2 | 4/2016 | Miller et al. | |
| 9,908,876 B2* | 3/2018 | Miller | A01N 43/90 |
| 2002/0091116 A1 | 7/2002 | Zhu | |
| 2005/0137395 A1 | 6/2005 | Hong | |
| 2006/0084806 A1 | 4/2006 | Sridharan | |
| 2008/0200473 A1 | 8/2008 | Falco | |
| 2008/0221093 A1 | 9/2008 | Gege et al. | |
| 2009/0163545 A1 | 6/2009 | Goldfarb | |
| 2010/0298314 A1 | 11/2010 | Reddy | |
| 2011/0166146 A1 | 7/2011 | Fang | |
| 2012/0010188 A1 | 1/2012 | Nilsson | |
| 2014/0088080 A1 | 3/2014 | Koga et al. | |
| 2014/0155387 A1 | 6/2014 | No et al. | |
| 2014/0256736 A1 | 9/2014 | Liu et al. | |
| 2017/0313697 A1 | 11/2017 | Lu et al. | |
| 2018/0354944 A1 | 12/2018 | Miller et al. | |

FOREIGN PATENT DOCUMENTS

| | | |
|---|---|---|
| CN | 104718213 | 6/2017 |
| DE | 4023215 | 1/1992 |
| EP | 450566 | 10/1991 |
| EP | 499995 | 8/1992 |
| GB | 2006067444 | 6/2006 |
| JP | 05039205 | 2/1993 |
| JP | 09249666 | 9/1997 |
| WO | 1995028389 | 10/1995 |
| WO | 1996002542 | 2/1996 |
| WO | 1999000356 | 1/1999 |
| WO | 1999063940 | 12/1999 |
| WO | 2000078726 | 12/2000 |
| WO | 2001019798 | 3/2001 |
| WO | 2001083481 | 11/2001 |
| WO | 2002020484 | 3/2002 |
| WO | 2004100868 | 11/2004 |
| WO | 2006015737 | 2/2006 |
| WO | 2007015866 | 2/2007 |
| WO | 2008038251 | 9/2007 |
| WO | 2007136607 | 11/2007 |
| WO | 2008063287 | 5/2008 |
| WO | 2008082490 | 7/2008 |
| WO | 2008109180 | 9/2008 |
| WO | 2008125594 | 10/2008 |
| WO | 2008154271 | 12/2008 |

(Continued)

OTHER PUBLICATIONS

Moraski, et al., Advent of Imidazo[1,2-a]pyridine-3-carboxamides with Potent Multi- and Extended Drug Resistant Antituberculosis Activity, ACS Med. Chem. Lett., 2, 466-470 (2011) (Year: 2011).*

(Continued)

*Primary Examiner* — Erich A Leeser
(74) *Attorney, Agent, or Firm* — Law Office of John K. Pike, PLLC

(57) ABSTRACT

Described herein are compounds and compositions, and methods of making and their use as effective agents against mycobacterial infections.

7 Claims, 37 Drawing Sheets

(56) References Cited

FOREIGN PATENT DOCUMENTS

| | | |
|---|---|---|
| WO | 2009015208 | 1/2009 |
| WO | 2008109179 | 9/2009 |
| WO | 2009148961 | 12/2009 |
| WO | 2010019796 | 2/2010 |
| WO | 2010030538 | 3/2010 |
| WO | 2011050245 | 4/2011 |
| WO | 2011113606 | 9/2011 |
| WO | 2014015167 | 1/2014 |
| WO | 2015014993 | 2/2015 |
| WO | 2017001660 | 1/2017 |
| WO | 2017001661 | 1/2017 |
| WO | 2017216281 | 12/2017 |
| WO | 2017216283 | 12/2017 |
| WO | 2018158280 | 9/2018 |

OTHER PUBLICATIONS

2009, Odell, Luke R., "Functionalized 3-amino-imidazo[1,2-a]pyridines: A Novel Class of Drug-like Mycobacterium Tuberculosis Glutamine Synthetase Inhibitors,"Bioorganic & Medicinal Chemistry Letters, 2009, vol. 19, pp. 4790-4793.
2004, Anaflous, A., et al., "Armed Imidazo [1,2-a} Pyridines): Evluation of Antibacterial Activity," Letters in Drug Design & Discovery 2004, vol. 1, pp. 224-229.
2004, Kasimogullari, et al.,"Fused Heterocycles: Synthesis of Some New Imidazo [1,2-a]-pyridine Derivatives." Molecules, 2004, vol. 9, pp. 894-901.
2007, Kasimogullari, et al.,"Fused Heterocycles: Synthesis of Some New Imidazopyridines as Anti-Mycobacterial Agents," Turk J. Chem, 2007, vol. 31, pp. 617-622.
Nov. 12, 2008, Search Results from Chemical Abstracts, Nov. 12, 2008.
2014, Mowbray, et. al.," Molecules" 2014, 19 pp. 13161-13176.
2014, Eoh, H., Tuberculosis xxx:, 2014 pp. 1-6.
2014, Bosch, et. al., "Annu. Rev. Phytopathol", 2014. 52: 175-95.
2010, Cesur, "Synthesis and Biological Evaluation of Some New Imidazo[1,2-a]pyridines," Acta Chim. Slov., 2010 vol. 57, pp. 355-362.
Jul. 20, 2011, International Search Report issued in Application PCT/US2010/055728.
May 8, 2012, International Preliminary Report on Patentability issued in application PCT/US2010/055728.
Jul. 19, 2011, Written Opinion issued in application PCT/US2010/055728.
Nov. 1, 2009, Qiao, L. et al.: " Structure-activity relationship study of EphB3 receptor tyrosine Kinase inhibitors", Bioorganic & Medicinal Chemistry Letters, Pergamon, Amsterdam, Nl vol. 19, No. 21 Nov. 1, 2009.
Sep. 27, 2017, Moraski, Garrett et. al.,: "Preparation and Evaluation of Potent Pentafluorosulfanyl-Substituted Anti-Tuberculosis Compounds", Chemmedchem, vol. 12, No. 14, Jun. 27, 2017, 1108-1115.
Oct. 10, 2017, Extended European Search Report issued for EP17168780 Completed Sep. 13, 2017, dated Oct. 10, 2017.
Apr. 4, 2019, Office Action issued for EP17168780 Completed Apr. 4, 2019 and dated Apr. 5, 2019.
1998, Cesur, "Some Imidazo[1,2-a] Pyridine Derivatives as Possible Antimicrobials" J. Fac. Pharm. Istanbul, 1998 vol. 32, pp. 2935.
Apr. 9, 2020, Summons to Attend Oral Proceedings issued for EP17168780 Completed Apr. 9, 2020 and dated Apr. 9, 2020.
Feb. 15, 2017, International Search Report issued in Application PCT/US2016/052558.
Mar. 23, 2011, Moraski, Garrett et. al.,: "Advent of Imidazo[1,2-a]pyridine-3-carboxamides with Potent Multi-and Extended Drug Resistant Antituberculosis Activity", Acs Med. Chem. Lett., Mar. 2011 vol. 2, pp. 466-470.

May 17, 2013, Moraski, Garrett et. al.,: "Advent of Imidazo[1,2-a]pyridines with Improved Pharmacokinetics and nM Activity vs. Mycobacterium Tuberculosis", Acs Med. Chem. Lett., May 2013 vol. 4, pp. 675-79.
May 28, 2014, Kang, Sunhee et. al.,: "Lead Optimization of a Novel Series of Imdicazo[1,2-a]pyridine Amides Leading to a Clinical Candidate (Q203) as a Multi-and Extensively-Drug-Resistant Antituberculosis Agent", J. Med. Chem., May 2014, 57, 5293-5305.
Feb. 15, 2017, Search Results STN in Application PCT/US2016/052558.
Feb. 15, 2017, Written Opinion issued in application PCT/US2016/052558.
Oct. 16, 2014, Search Results STN in U.S. Appl. No. 13/508,011.
Jul. 16, 2020, Search Report issued in CN Application 2016800630427.
Jul. 22, 2020, Office Action issued in CN Application 2016800630427.
Jul. 17, 2019, Li, Linhu, et al.,: "N-(2-Phenoxy)ethylimidazo[1,2-a]pyridine-3-carboxamides containing various amine moieties: Design, synthesis and antitubercular activity", Chinese Chem. Lett. 2020, 31, pp. 409-12.
Reddyrajula, R. et al,: "Structural modification of zolpidem led to potent antimicrobial activity in imidazo[1,2-a]pyridine/ pyrimidine-1,2,3-triazoles", New. J. Chem. 2019, 43 16281.
Dec. 28, 2018, Wang, Hongjian, et al.,: "Synthesis and antitubercular evaluation of reduced lipophilic imidazo [1,2-a]pyridine-3-carboxamide derivatives", European J. Med. Chem., 165 (2019) 11-17.
Jun. 14, 2019, Wang, Apeng, et al.,: "Design, synthesis and biological activity of N-(2-phenoxy)ethyl imidazo[1,2-a]pyridine-3-carboxamides as new antitubercular agents", European J. Med. Chem., 178 (2019) 715-725.
Jan. 23, 2019, Wang, Apeng, et al.,: "Design, synthesis and antimycobacterial activity of less lipophilic Q203 derivatives containing alkaline fused ring moieties", Bioorg. & Med. Chem., 27 (2019) 813-21.
May 27, 2017, Lv, Kai, et al.,: "Design, synthesis and antimycobacterial activity of novel imidazo[1,2- a]pyridine-3-carboxamide derivatives", European J. Med. Chem., 137 (2017) 117-125.
May 10, 2017, Kang, Sunhee, et al.,: "Synthesis and structure-activity relationships of novel fused ring analogues of Q203 as antitubercular agents", European J. Med. Chem., 136 (2017) 420-427.
Sep. 28, 2016, Kang, Suhee, et al.,: "Synthesis and structure-activity studies of side chain analogues of the anti-tubercular agent, Q203", European J. Med. Chem., 125 (2017) 807-815.
Oct. 11, 2016, Wu, Zhaoyang, et al.,: "Identification of N-(2-Phenoxyethyl)imidazo[1,2 - a] pyridine-3-carboxamides as New Antituberculosis Agents", Acs Med. Chem. Lett., 2016, 7, 1130-1133.
May 23, 2016, Moraski, Garrett, et al.,: "Imidazo[1,2-a]Pyridine-3-Carboxamides Are Active Antimicrobial Agents against Mycobacterium avium Infection in Vivo", Antimicrobial Agents and Chemotherapy, Aug. 2016, vol. 60, No. 8, 5018-5022.
Apr. 30, 2016, Pulipati, Lokesh, et al.,: "Synthesis and antitubercular evaluation of novel dibenzo[b,d] thiophene tethered imidazo[1,2-a]pyridine-3-carboxamides", Bioorg. & Med. Chem., 26 (2016) 3135-3140.
Apr. 5, 2016, Moraski, et al.,: "Arrival of Imidazo[2,1-b]thiazole-5-carboxamides: Potent Antituberculosis Agents That Target QcrB", Acs Infect. Dis. 2016, 2, 393-398.
Apr. 22, 2016, Ko, Yoonae, et al.,: "Putative 3D Structure of QcrB from Mycobacterium tuberculosis Cytochrome bc1 Complex, a Novel Drug-Target for New Series of Antituberculosis Agent Q203", Bull. Korean Chem. Soc. 2016, vol. 37, 725-731.
Dec. 30, 2015, Li, Linhu, et al.,: "Design, Synthesis and Antimycobacterial Activity of Novel Imidazo[1,2-a]pyridine Amide-Cinnamamide Hybrids", Molecules 2016, vol. 21, pp. 1-14.
Mar. 11, 2015, Abhale, Yogita K., et al.,: "Fused Heterocycles: Synthesis and Antitubercular Activity of Novel 6-Substituted-2-(4-methyl-2-substituted phenylthiazol-5-y1)H-imidazo[1,2-a]pyridine", J. Heterocyclic Chem., 53, 229 (2016), pp. 229-233.

(56) References Cited

OTHER PUBLICATIONS

Dec. 27, 2014, Moraski, Garrett, et al.,: "Putting Tuberculosis (Tb) to Rest: Transformation of the Sleep Aid, Ambien, and "Anagrams" Generated Potent Antituberculosis Agents", Acs Infect. Dis. 2015, 1, 85-90.

Oct. 30, 2014, Jose, Gilish, et al.,: "Synthesis, molecular docking and anti-mycobacterial evaluation of new imidazo[1,2-a]pyridine-2-carboxamide derivatives", European J. Med. Chem. 89 (2015) 616-627.

May 28, 2014, Moraski, Garrett, et al.,: "Scaffold-switching: an exploration of 5,6-fused bicyclic heteroaromatics systems to afford antituberculosis activity akin to the imidazo[1,2-a]pyridine-3-carboxylates", Bioorg. Med. Chem. Lett. 24 (2014) 34933498.

Jan. 31, 2014, Cheng, Yong, et al.,: "Bactericidal Activity of an Imidazo[1, 2-a]pyridine Using a Mouse M. tuberculosis Infection Model", Plos One, Jan. 2014, vol. 9, Issue 1, e87483, pp. 1-8.

Jun. 24, 2013, Ramachandran, Sreekanth, et al.,: "Synthesis and structure activity relationship of imidazo[1,2-a]pyridine-8-carboxamides as a novel antimycobacterial lead series", Bioorg. Med. Chem. Lett. 23 (2013) 49965001.

May 17, 2013, Moraski, Garrett, et al.,: "Advancement of Imidazo[1,2 - a]pyridines with Improved Pharmacokinetics and nM Activity vs. Mycobacterium tuberculosis", Acs Med. Chem. Lett. 2013, 4, 675-679.

Apr. 4, 2013, Ollinger, Juliane, et al.,: "A Dual Read-Out Assay to Evaluate the Potency of Compounds Active against Mycobacterium tuberculosis", PLOS One, Apr. 2013, vol. 8, Issue 4, e60531, pp. 1-9.

Dec. 31, 2012, Abrahams, Katherine a., et al.,: "Identification of Novel Imidazo[1,2-a]pyridine Inhibitors Targeting M. tuberculosis QcrB", PLOS One, Dec. 2012, vol. 7, Issue 12, e52951, pp. 1-10.

Feb. 16, 2012, Moraski, Garrett, et al.,: "Generation and exploration of new classes of antitubercular agents: The optimization of oxazolines, oxazoles, thiazolines, thiazoles to imidazo[1,2-a]pyridines and isomeric 5,6-fused scaffolds", Bioorg. Med. Chem. 20 (2012) 2214-2220.

U.S. Appl. No. 61/258,549, filed Nov. 5, 2009.

U.S. Pat. No. PCT/US10/55728, dated Nov. 5, 2020.

U.S. Appl. No. 13/508,011, now U.S. Pat. No. 9,309,238, dated May 3, 2012.

U.S. Appl. No. 15/056,630, now U.S. Pat. No. 9,908,876, dated Feb. 29, 2016.

U.S. Appl. No. 15/888,605, filed Feb. 5, 2018.

Aug. 21, 2020, Office Action issued in JP2018-514425 dated Aug. 21, 2020.

* cited by examiner

*M. avium In Vivo* Efficacy in Mouse
(ND-10885)
ND-10885 displays ~1.5 log10 CFU bacterial drop in lung (A); spleen (B) and liver (C) when dosed alone.
Combination treatment ND-10885 and Rifampcin (RMP) improves potency in lung (site of infection).

Figure 3: Example: MICs – Against *M. avium*

| | MIC M. avium 101 (ug/mL) | MIC M. avium Serotype 1 (ug/mL) | MIC M. avium 2151 (ug/mL) | MIC M. avium Serotype 9 (ug/mL) | MIC M. avium Serotype 10 (ug/mL) | MIC M. avium Serotype 5 (ug/mL) | MIC M. avium Serotype 6 (ug/mL) | MIC M. avium Serotype 8 (ug/mL) | MIC M. avium A5 (ug/mL) | MIC M. avium Serotype 4 (ug/mL) | MIC M. avium 104 Gentamicin Res. (ug/mL) |
|---|---|---|---|---|---|---|---|---|---|---|---|
| ND-11176 | <0.0078 | 0.01562 | 0.3125 | 0.3125 | 0.125 | 0.125 | 0.125 | 0.0625 | >1.0 | >1.0 | 0.0156 |
| ND-11543 | 0.3125 | <0.0078 | 0.0625 | 0.125 | 0.125 | 1 | >1.0 | 1 | >1.0 | >1.0 | 0.3125 |
| ND-11544 | 0.01562 | <0.0078 | 0.0625 | 0.0625 | 0.0625 | 0.125 | 0.125 | 0.125 | >1.0 | >1.0 | <0.0078 |
| ND-11598 | 0.01562 | <0.0078 | 0.3125 | 0.3125 | 0.3125 | 0.0625 | 0.125 | 0.0625 | >1.0 | >1.0 | <0.0078 |
| ND-11622 | <0.0078 | <0.0078 | 0.3125 | 0.125 | 0.125 | 0.0625 | 0.0625 | 0.3125 | >1.0 | >1.0 | <0.0078 |
| Rifampin | 0.3125 | 0.25 | 0.0156 | <0.0078 | 0.25 | 0.5 | 0.125 | 0.3125 | 0.01562 | 0.0078 | 0.125 |
| DMSO | >1.0 | >1.0 | >1.0 | >1.0 | >1.0 | >1.0 | >1.0 | >1.0 | >1.0 | >1.0 | >1.0 |

Figure 4
Example: MICs Against *M. intracellulare* (ATCC 13950)

| Compound | *M. intracellulare* ATCC 13950 MIC (µg/ml) |
|---|---|
| ND-11176 | <0.0078 |
| ND-11543 | 0.125 |
| ND-11544 | 0.03125 |
| ND-11598 | 0.03125 |
| ND-11622 | 0.015625 |
| Rifampin | <0.0078 |
| Clarithromycin | 0.125 |
| Ethambutol | 1 |
| Azithromycin | 5 |
| DMSO (neg. control) | >10 |

Figure 5
MICs Against *M. avium*
*(clinical isolates)*

| Compound | *M. avium* (clinical isolates) MIC in ug/mL | | | | |
| --- | --- | --- | --- | --- | --- |
| | MAC PRV | MAC 224 | MAC LPR | MAC 9141 | MAC KAL |
| Clarithromycin | 128 | 128 | 0.25 | ≤0.125 | 0.5 |
| ND-11176 | <0.03 | 0.06 | 2 | <0.03 | 0.06 |
| ND-10885 | 4 | 4 | >32 | 2 | 4 |
| ND-11450 | NT | 0.25 | NT | NT | 0.25 |
| ND-11666 | NT | ≤0.03 | NT | NT | ≤0.03 |

Figure 6
MICs Against *M. kansasii*
(clinical isolates)

| | M. kansasii clinical isolates MIC in ug/mL | | |
|---|---|---|---|
| Compound | MK SHP | MK 379 | MK 0008 |
| Clarithromycin | 0.125 | <0.06 | 0.125 |
| ND-11176 | 0.125 | <0.06 | 0.25 |
| ND-10885 | 32 | 1 | 32 |

MICs of ND-11176 + Clofazimine Against *M. abscessus*

Figure 8
| Cpd ID | Structure | Mol Wt | Toxicity: VERO Cells: IC50 (uM) | 7H12: H37Rv TB: MIC 90 | GAS: H37Rv TB: MIC 90 | LORA: MIC 90 | Resazurin M. Avium 101 | Resazurin M. avium 2151 | Resazurin M. intracellulare |
|---|---|---|---|---|---|---|---|---|---|
| | | | A = < 2 uM; B = 2 uM - 10 uM; C = < 10 uM - 20 uM; D = < 20 uM - 32 uM; E = >32 uM | | | | | | |
| ND-009584 | 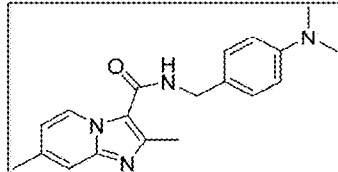 | 322.4 | E | A | A | B | A | B | |
| ND-009873 | 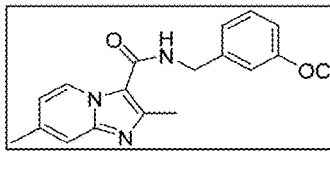 | 363.3 | E | A | A | E | A | B | |
| ND-010885 | 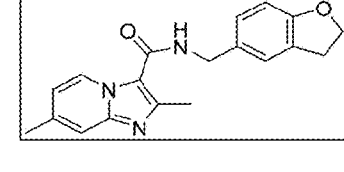 | 321.4 | E | A | A | E | A | B | |
| ND-010890 | 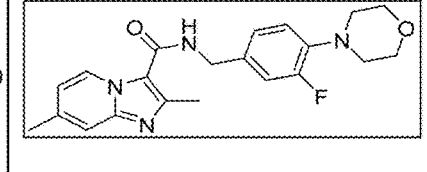 | 382.4 | E | A | A | E | A | B | |
| ND-011176 | 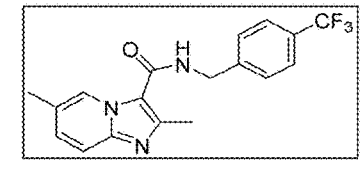 | 347.3 | E | A | A | C | A | A | A |

Figure 8 (continued)
| | | | | | | | | | |
|---|---|---|---|---|---|---|---|---|---|
| ND-011454 | 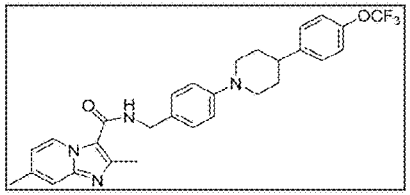 | 522.6 | E | A | A | A | A | A | A |
| ND-011457 | 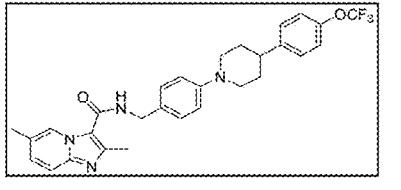 | 522.6 | E | A | A | B | | | |
| ND-011458 | 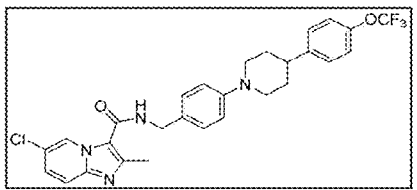 | 543 | E | A | A | B | | | |
| ND-011461 | 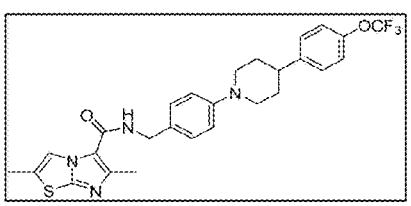 | 528.6 | E | A | A | A | A | A | A |
| ND-011496 | 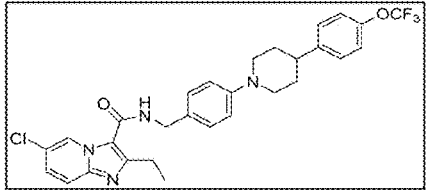 | 557 | E | A | A | B | A | A | A |

Figure 8 (continued)

| ID | Structure | MW | | | | | | | |
|---|---|---|---|---|---|---|---|---|---|
| ND-011530 | 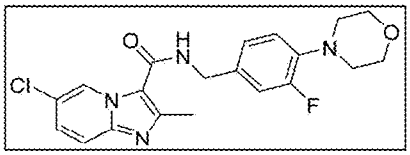 | 402.9 | E | A | A | E | | | |
| ND-011543 | 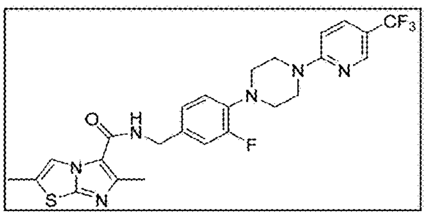 | 532.6 | E | A | A | D | A | A | A |
| ND-011544 | 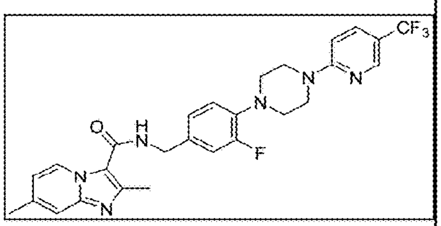 | 526.5 | E | A | A | B | A | A | A |
| ND-011546 | 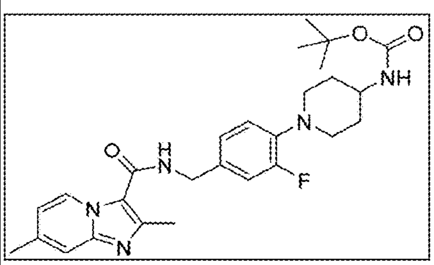 | 495.6 | E | A | A | E | A | B | |

Figure 8 (continued)
| | | | | | | | | |
|---|---|---|---|---|---|---|---|---|
| ND-011560 | 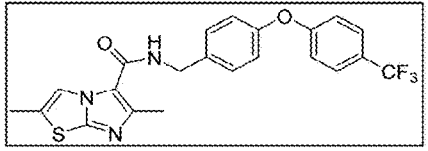 | 445.6 | E | A | A | D | A | A |
| ND-011561 | 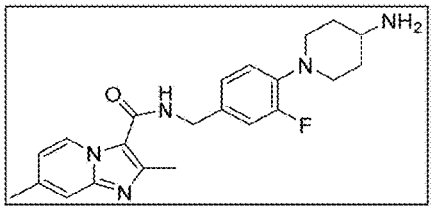 | 395.5 | E | A | A | E | | |
| ND-011563 | 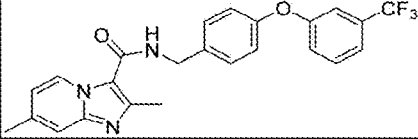 | 439.4 | E | A | A | C | A | A |
| ND-011586 | 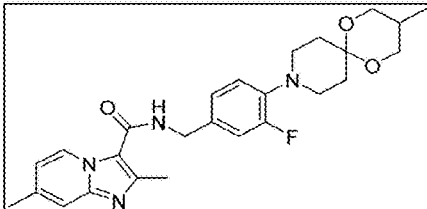 | 466.6 | E | A | A | D | B | B |
| ND-011592 | 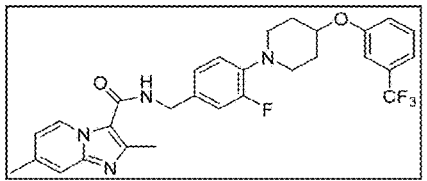 | 540.6 | E | A | A | A | | |

Figure 8 (continued)
| ID | Structure | MW | | | | | | |
|---|---|---|---|---|---|---|---|---|
| ND-011594 | 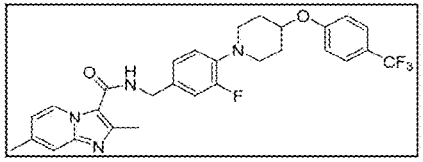 | 540.6 | D | A | A | A | | |
| ND-011598 | 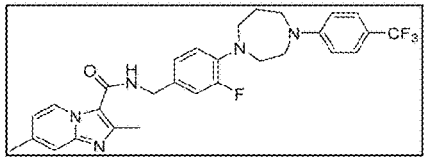 | 539.6 | E | A | A | A | A | A | A |
| ND-011613 | 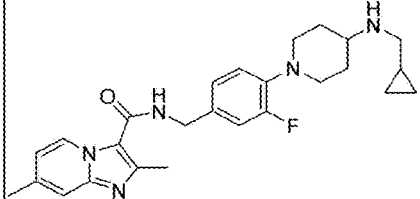 | 449.6 | E | A | A | B | | |
| ND-011617 | 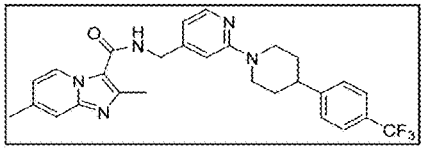 | 507.6 | E | A | A | B | B | C |
| ND-011619 | 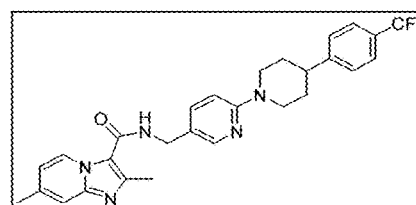 | 507.6 | E | A | A | B | A | A |

Figure 8 (continued)
| | | | | | | | | | |
|---|---|---|---|---|---|---|---|---|---|
| ND-011620 | 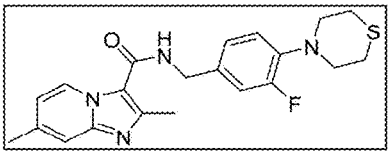 | 398.5 | E | A | A | A | A | B | |
| ND-011621 | 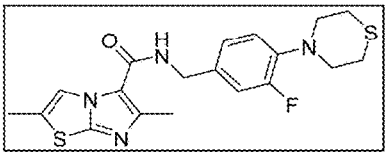 | 404.5 | E | A | A | E | A | A | A |
| ND-011622 | 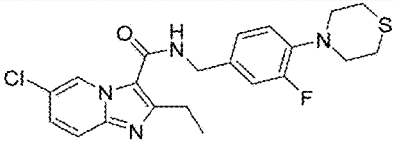 | 432.9 | E | A | A | A | A | A | A |
| ND-011657 | 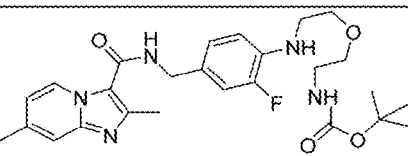 | 500.6 | E | C | B | E | | | |
| ND-011658 | 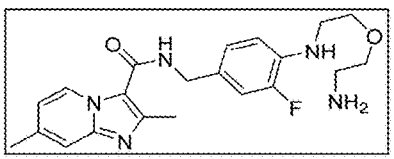 | 400.5 | E | E | D | E | | | |

Figure 8 (continued)
| | | | | | | | | | | |
|---|---|---|---|---|---|---|---|---|---|---|
| ND-011662 | 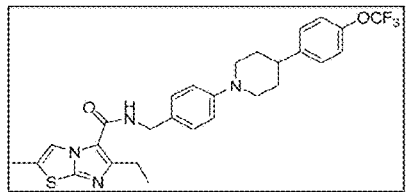 | 542.6 | E | A | A | E | | | | |
| ND-011666 | 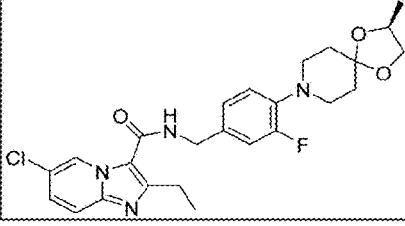 | 487 | E | C | A | E | | | | |
| ND-011667 | 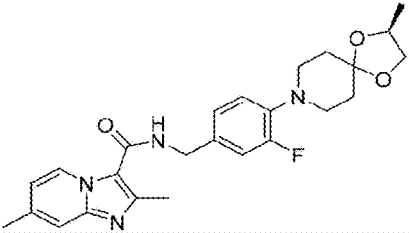 | 452.5 | E | D | A | E | | | | |
| ND-011769 | 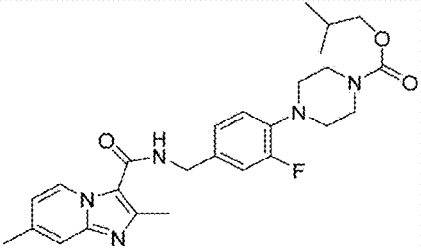 | 481.6 | C | B | A | E | | | | |

Figure 8 (continued)

| ID | Structure | MW | | | | | | | |
|---|---|---|---|---|---|---|---|---|---|
| ND-011770 | (structure) | 487.6 | E | A | B | E | | | |
| ND-011772 | (structure) | 425.5 | E | D | B | E | | | |
| ND-011774 | (structure) | 459.9 | E | B | A | E | | | |
| ND-011459 | (structure) | 327.4 | E | B | A | B | | | |
| ND-11503 | (structure) | 341.4 | E | A | A | B | | | |

Figure 8 (continued)
| | | | | | | | | | | |
|---|---|---|---|---|---|---|---|---|---|---|
| ND-11460 | 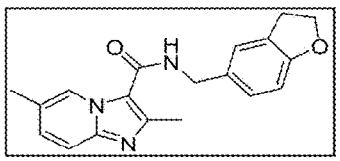 | 321.4 | E | A | A | D | | | | |
| ND-11497 | 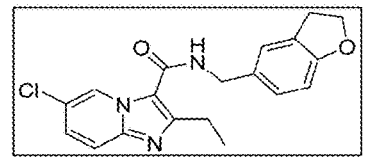 | 355.8 | E | A | A | A | | | | |
| ND-11465 | 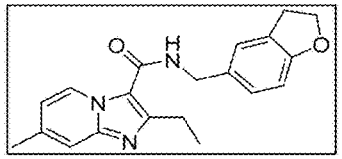 | 335.4 | E | A | A | E | | | | |
| ND-11935 | 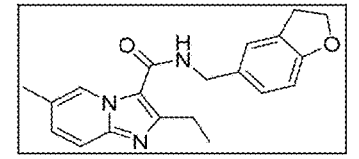 | 335.4 | E | A | A | D | | | | |
| ND-11535 | 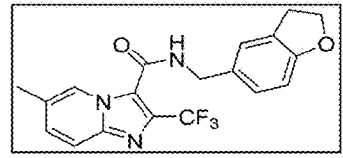 | 375.3 | E | A | A | D | | | | |
| ND-11504 | 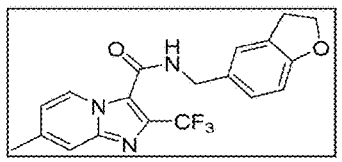 | 375.3 | E | A | A | D | | | | |

Figure 8 (continued)
| ID | Structure | MW | | | | | | | |
|---|---|---|---|---|---|---|---|---|---|
| ND-11493 | 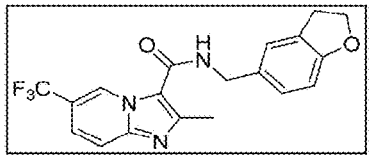 | 375.3 | E | B | B | E | | | |
| ND-11466 | 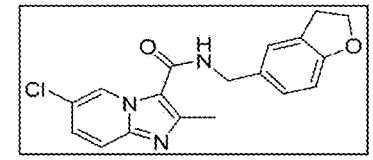 | 341.8 | E | A | A | D | | | |
| ND-11505 | 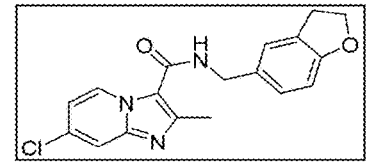 | 341.8 | E | A | A | A | | | |
| ND-11584 | 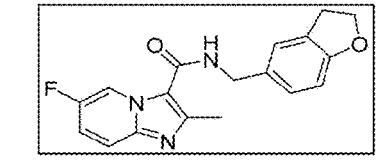 | 325.3 | E | A | A | E | | | |
| ND-11460 | 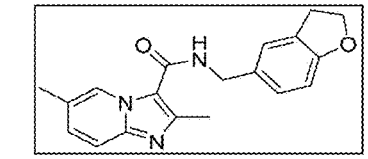 | 321.4 | E | A | A | E | | | |
| ND-11860 | 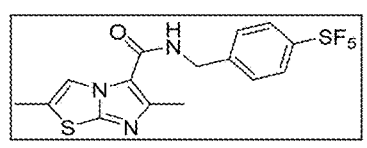 | 411.4 | E | A | A | B | | | |

Figure 8 (continued)

| | | | | | | |
|---|---|---|---|---|---|---|
| ND-11919 | | 425.4 | E | A | A | B |
| ND-11859 | | 405.4 | E | A | A | A |
| ND-11858 | | 439.8 | E | A | A | A |
| ND-11920 | | 419.4 | E | A | A | B |
| ND-11857 | | 405.4 | E | A | A | A |
| ND-11867 | | 411.4 | D | A | A | D |

Figure 8 (continued)
| ID | Structure | | | | | | | | | |
|---|---|---|---|---|---|---|---|---|---|---|
| ND-11921 | 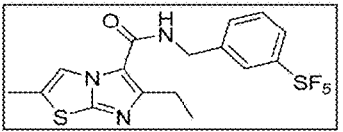 | 425.4 | D | A | A | D | | | | |
| ND-111866 | 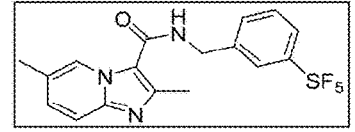 | 405.4 | D | A | A | C | | | | |
| ND-11865 | 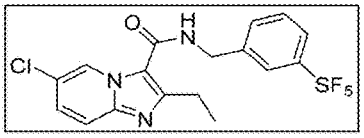 | 439.8 | E | A | A | D | | | | |
| ND-11922 | 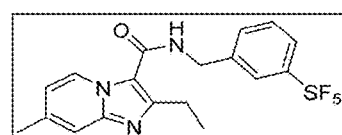 | 419.4 | E | A | A | D | | | | |
| ND-11864 | 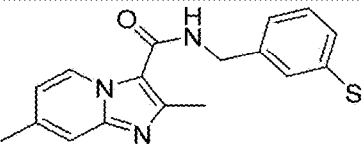 | 419.4 | D | A | A | B | | | | |
| ND-11878 | 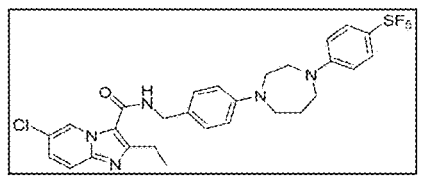 | 613.2 | E | A | A | A | | | | |

Figure 8 (continued)
| | | | | | | | | | | |
|---|---|---|---|---|---|---|---|---|---|---|
| ND-11877 | 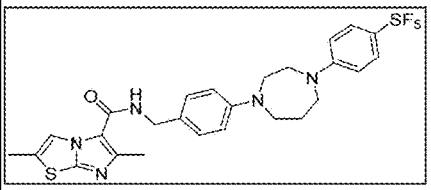 | 585.7 | E | A | A | A | | | | |
| ND-11876 | 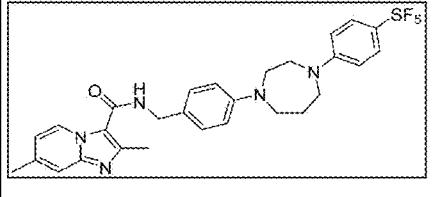 | 579.6 | C | A | A | A | | | | |
| ND-11875 | 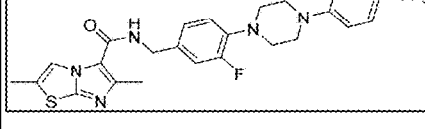 | 589.6 | E | A | A | A | | | | |
| ND-11874 | 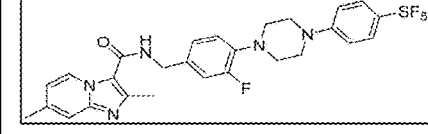 | 583.6 | C | A | A | A | | | | |
| ND-11873 | 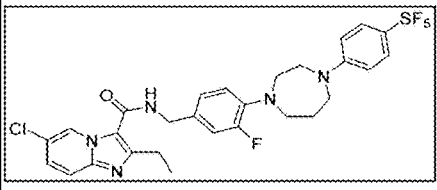 | 632.1 | E | A | A | A | | | | |

Figure 8 (continued)
| | | | | | | |
|---|---|---|---|---|---|---|
| ND-11872 | 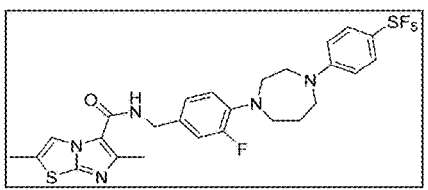 | 597.6 | D | A | A | A |
| ND-11870 | 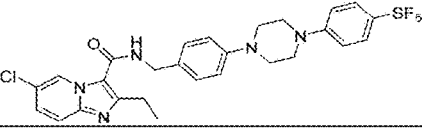 | 600.1 | E | A | A | A |
| ND-11869 | 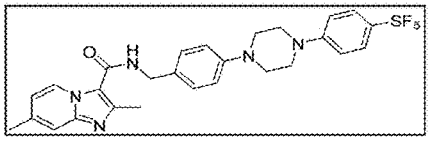 | 571.6 | D | A | A | A |
| ND-11868 | 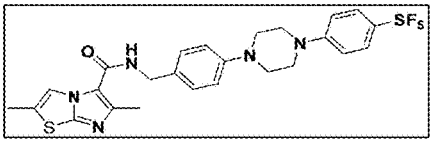 | 565.6 | B | A | A | A |
| ND-11665 | 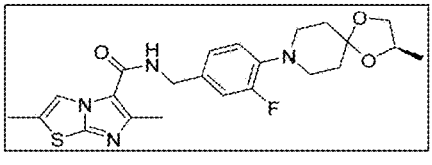 | 458.9 | D | A | A | E |
| ND-11863 | 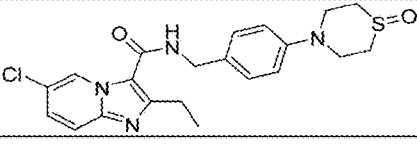 | 431 | E | A | A | A |

Figure 8 (continued)

| ID | Structure | MW | | | | | | | |
|---|---|---|---|---|---|---|---|---|---|
| ND-11901 | 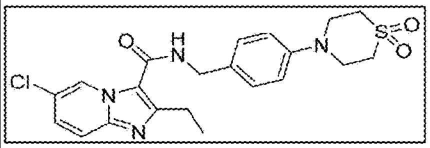 | 447 | E | B | B | D | | | |
| ND-11902 | 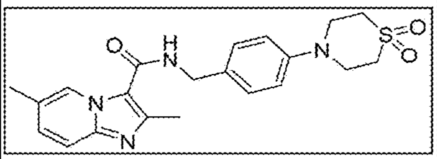 | 430.5 | E | A | A | D | | | |
| ND-11903 | 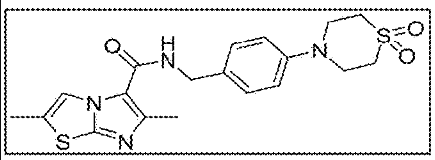 | 436.5 | E | B | A | D | | | |
| ND-11944 | 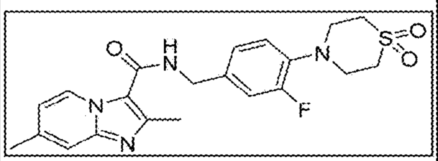 | 430.5 | E | A | A | E | | | |
| ND-11927 | 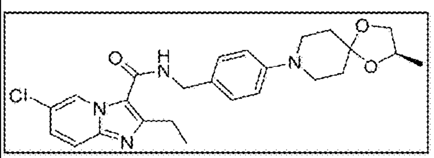 | 469 | | | | | | | |
| ND-11926 | 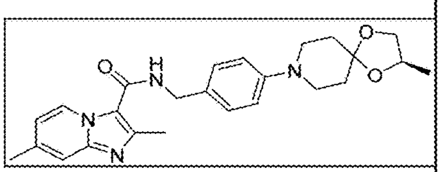 | 434.5 | | | | | | | |

Figure 8 (continued)

| ND-11928 | [structure] | 440.6 | | | | | | | |
| ND-11941 | [structure] | 435.5 | | | | | | | |
| ND-11942 | [structure] | 470 | | | | | | | |
| ND-11943 | [structure] | 441.6 | | | | | | | |
| ND-11929 | [structure] | 466.6 | | | | | | | |
| ND-11929 | [structure] | 441.6 | | | | | | | |

Figure 8 (continued)

| ID | Structure | Mass |
|---|---|---|
| ND-11940 | | 472.6 |
| ND-12000 | | 564.6 |
| ND-12001 | | 564.6 |
| ND-12002 | | 599.1 |
| ND-12003 | | 570.6 |
| ND-12004 | | 426.5 |

Figure 8 (continued)
| | | |
|---|---|---|
| ND-12005 | 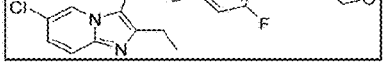 | 460.9 |
| ND-12006 |  | 567.6 |
| ND-12007 |  | 540.6 |
| ND-12008 | 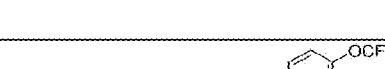 | 540.6 |

Figure 8 (continued)

| | | |
|---|---|---|
| ND-12009 | [structure] | 575 |
| ND-12010 | [structure] | 540.6 |
| ND-12011 | [structure] | 321.4 |
| ND-12012 | [structure] | 321.4 |
| ND-12013 | [structure] | 355.8 |
| ND-12014 | [structure] | 327.4 |

Figure 8 (continued)
| | | |
|---|---|---|
| ND-12015 |  | 319.4 |
| ND-12016 |  | 319.4 |
| ND-12017 |  | 353.8 |
| ND-12018 |  | 325.4 |
| ND-12019 |  | 337.4 |
| ND-12020 |  | 339.4 |
| ND-12021 |  | 335.4 |

Figure 8 (continued)

| ID | Structure | Value |
|---|---|---|
| ND-12022 | | 335.4 |
| ND-12023 | | 369.8 |
| ND-12024 | | 341.4 |
| ND-12025 | | 350.4 |
| ND-12026 | | 350.4 |
| ND-12027 | | 384.9 |

Figure 8 (continued)
| | | | |
|---|---|---|---|
| ND-12028 |  | 356.4 | |
| ND-12029 | 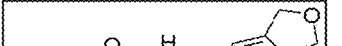 | 321.4 | |
| ND-12030 | 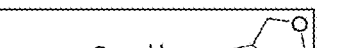 | 321.4 | |
| ND-12031 | 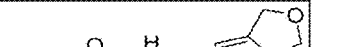 | 355.8 | |
| ND-12032 |  | 327.4 | |
| ND-12033 | 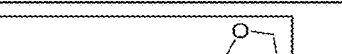 | 323.4 | |
| ND-12034 |  | 323.4 | |

Figure 8 (continued)

| ID | Structure | Value |
|---|---|---|
| ND-12035 | (structure) | 357.8 |
| ND-12036 | (structure) | 329.4 |
| ND-12037 | (structure) | 335.4 |
| ND-12038 | (structure) | 335.4 |
| ND-12039 | (structure) | 369.9 |
| ND-12040 | (structure) | 341.4 |
| ND-12041 | (structure) | 359.3 |

Figure 8 (continued)
| | | |
|---|---|---|
| ND-12042 |  | 359.3 |
| ND-12043 |  | 393.8 |
| ND-12044 |  | 365.4 |
| ND-12045 |  | 337.4 |
| ND-12046 | 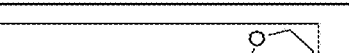 | 337.4 |
| ND-12047 | 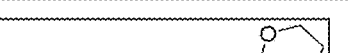 | 371.8 |

Figure 8 (continued)
| | | |
|---|---|---|
| ND-12048 | 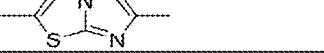 | 343.4 |
| ND-12049 |  | 335.4 |
| ND-12050 |  | 335.4 |
| ND-12051 | 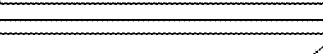 | 369.9 |
| ND-12052 | 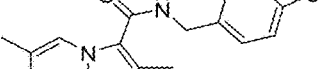 | 341.4 |
| ND-12053 | 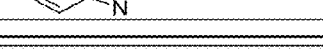 | 351.4 |

Figure 8 (continued)
| | | |
|---|---|---|
| ND-12054 | 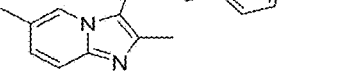 | 351.4 |
| ND-12055 | 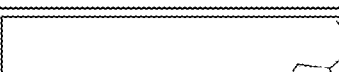 | 385.9 |
| ND-12056 | 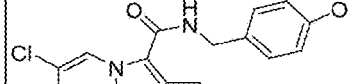 | 357.4 |
| ND-12057 | 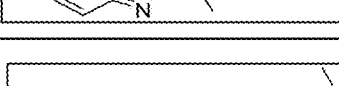 | 337.4 |
| ND-12058 | 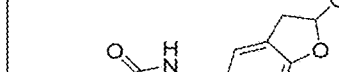 | 339.4 |
| ND-12059 | 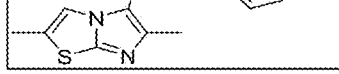 | 335.4 |

Figure 8 (continued)
| | | |
|---|---|---|
| ND-12060 | 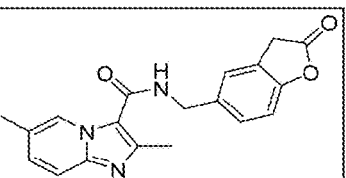 | 335.4 |
| ND-12061 | 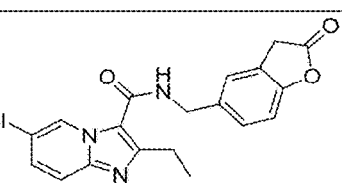 | 369.8 |
| ND-12062 | 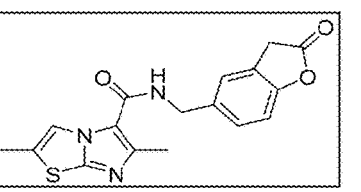 | 341.4 |
| ND-12063 | 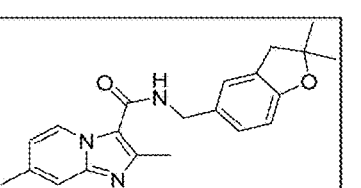 | 349.4 |
| ND-12064 | 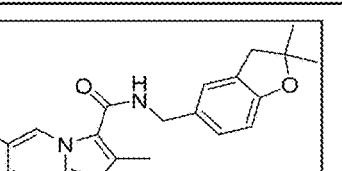 | 349.4 |
| ND-12065 | 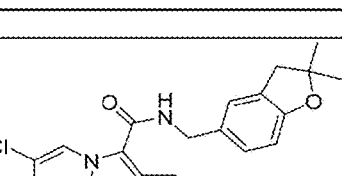 | 383.9 |

Figure 8 (continued)
| | | | | | | | | | | |
|---|---|---|---|---|---|---|---|---|---|---|
| ND-12066 |  | 355.5 | | | | | | | | |
| ND-12067 |  | 335.4 | | | | | | | | |
| ND-12068 |  | 335.4 | | | | | | | | |
| ND-12069 |  | 369.9 | | | | | | | | |
| ND-12070 | 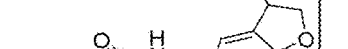 | 341.4 | | | | | | | | |
| ND-12071 | 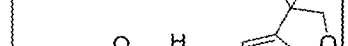 | 349.4 | | | | | | | | |

Figure 8 (continued)
| | | |
|---|---|---|
| ND-12072 | 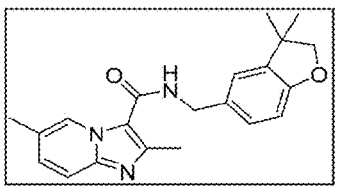 | 349.4 |
| ND-12073 | 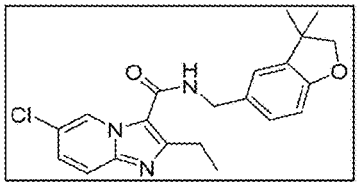 | 383.3 |
| ND-12074 | 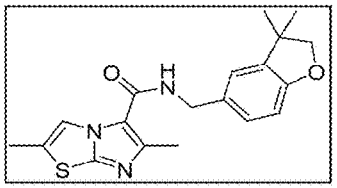 | 355.5 |
| ND-12075 | 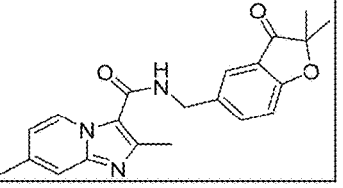 | 363.4 |
| ND-12076 | 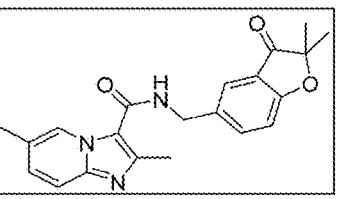 | 363.4 |
| ND-12077 | 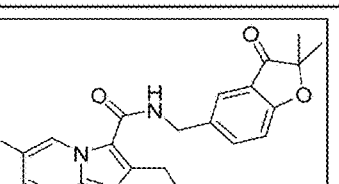 | 397.9 |

Figure 8 (continued)
| | | |
|---|---|---|
| ND-12078 | 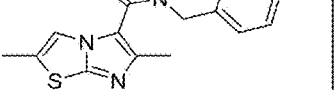 | 369.4 |
| ND-12079 | 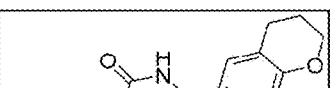 | 335.4 |
| ND-12080 | 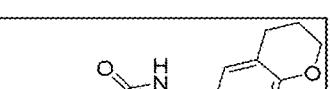 | 335.4 |
| ND-12081 | 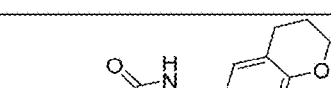 | 369.9 |
| ND-12082 | 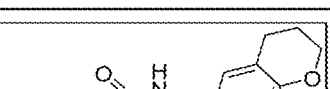 | 341.4 |

BENZYL AMINE-CONTAINING HETEROCYCLIC COMPOUNDS AND COMPOSITIONS USEFUL AGAINST MYCOBACTERIAL INFECTION

RELATED APPLICATIONS

This application claims the benefit of U.S. Provisional Application No. 62/220,192, filed Sep. 17, 2015, the entire contents of which are hereby incorporated by reference.

STATEMENT REGARDING FEDERALLY FUNDED RESEARCH

This invention was made with government support under grant R01AI054193 awarded by the National Institutes of Health (NIH). The government has certain rights in the invention.

BACKGROUND

There is an urgent need for new treatments for mycobacterial infections globally and nationally. Mycobacterial infections are caused by pathogens like *Mycobacterium tuberculosis* (Mtb), the causative agent of tuberculosis (TB), and close relatives such as *Mycobacterium avium* (MAC). Every 20 seconds someone dies of TB, and the cure rate of an MAC infection can be as low as 30%. Over one third of the people on the planet are infected with Mtb, posing a major global health threat. The greatest concern lies in the rapid rise in the hard to kill, drug resistant strains of Mtb. These currently infect 450,000 people globally and are appearing with increasing frequency in the U.S. TB is an air borne pathogen, it is easily transmitted from person to person through coughing, making even one case potentially very dangerous. Available treatments for these strains are only modestly effective but extremely costly.

Described herein are agents that can be a treatment for one or both of Mtb and MAC infections. There is an unmet medical need for compounds effective against one or both of Mtb and MAC pathogens, and the present compounds are considered to be effective against the drug resistant strains as a single agent or in combination therapy.

DESCRIPTION OF THE FIGURES

FIG. 3 presents in table form in vitro potency of several compounds against various serotypes of *Mycobacterium avium* plus a gentamicin resistant *M. avium* strain. Rifampin is included as a positive control and DMSO as a negative control. MIC values are reported in μg/mL and read by Resazurin dye.

FIG. 4 presents in table form in vitro potency of several compounds against *Mycobacterium intracellulare* (ATCC 13950). Rifampin, Clarithromycin, Ethanbutol, and Azithromycin are included as a positive controls and DMSO as a negative control. MIC values are reported in μg/mL and read by Resazurin dye.

FIG. 5 presents in table form in vitro potency of several compounds against clinical isolates of *Mycobacterium avium* and Clarithromycin was used as a positive control. MIC values are reported in μg/mL and read by 3-(4,5-dimethylthiazol-2-yl)-2,5-diphenyltetrazolium bromide (MTT) dye.

FIG. 6 presents in table form in vitro potency of several compounds against clinical isolates of *Mycobacterium kansasii*; Clarithromycin was used as a positive control. MIC values are reported in μg/mL and read by 3-(4,5-dimethylthiazol-2-yl)-2,5-diphenyltetrazolium bromide (MTT) dye.

FIG. 8 presents in table form compounds and screening results obtained against *Mycobacterium tuberculosis* (Mtb) H37Rv in various media (GAS, 7H12), in low oxygen conditions (LORA), the toxicity to Vero cells, as well as the potency against *Mycobacterium avium* (101 and 2151) and *Mycobacterium intracellulare*. Resazurin dye is used to read MICs against *M. avium* and *M. intracellulare* while MABA was used to read out MICs against Mtb.

DESCRIPTION OF THE SEVERAL EMBODIMENTS

Figure 1:
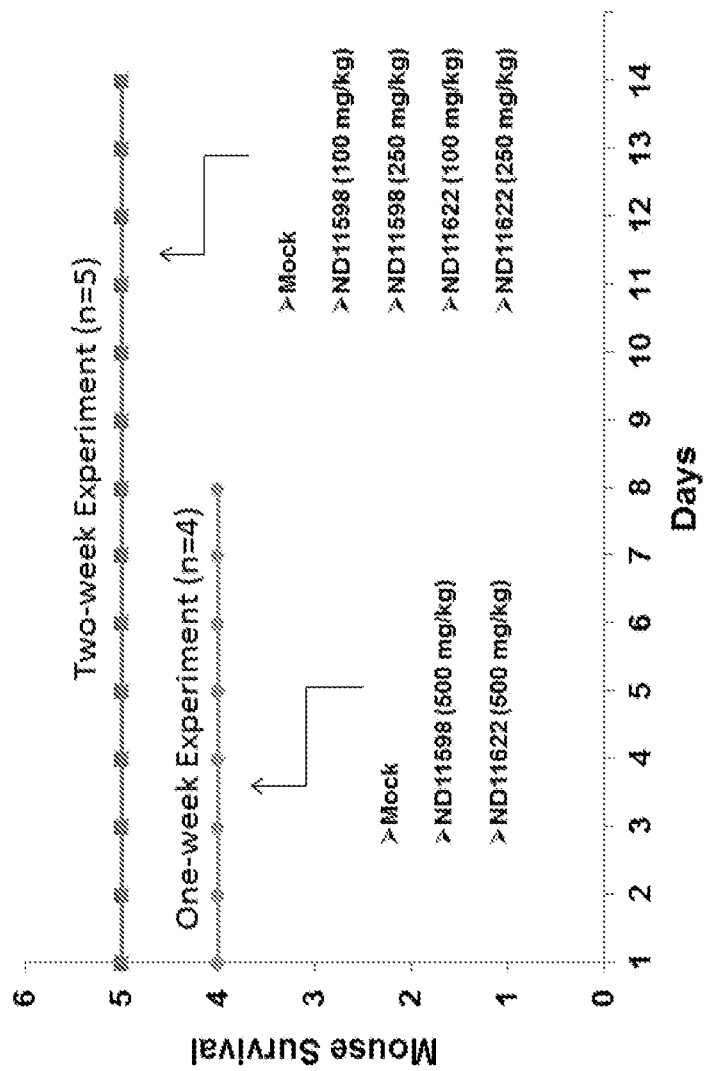
FIG. 1 graphically presents in vivo tolerability observed in mice of two representative compounds ND-11598 and ND-11622 at 100 mg/kg dosed orally for two weeks and 250 mg/kg dosed orally for one week. The mice showed no signs of distress, no weight loss and all survived the treatment course.

In one embodiment, a compound is provided, having one of the following formulas:

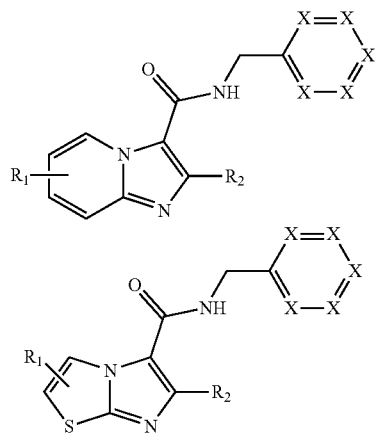

wherein each X is independently N, C—R3, or C—R4; with the proviso that no more than two X's are N and wherein one or more C—R3 or C—R4 group may join with another C—R3 or C—R4 to form a fused ring;

wherein R1 and R2 are each independently hydrogen, acyl group, alkenyl group, alkoxy group, alkoxycarbonyl group, alkoxycarbonyloxy group, alkoxysulfonyloxy group, alkyl group, alkylamino group, alkylaminocarbonyl group, alkylcarbonyl group, alkylcarbonyloxy group, alkylsulfonyl group, alkylsulfonyloxy group, alkylthio group, alkynyl group, amide group, amidine group, amino group, arylalkoxy group, arylalkyl group, aryl group, arylcarbonyl group, arylcarbonyloxy group, aryloxy group, aryloxycarbonyl group, aryloxycarbonyloxy group, aryloxysulfonyloxy group, arylsulfonyl group, atylsulfonyloxy group, azido group, carbamido group, carbamoyl group, carbazoyl group, carbonyl group, carboxylate group, carboxylic acid group, cyanato group, cyano group, cycloalkenyl group, cycloalkyl group, dialkylamino carbonyl group, dialkylamino group, guanidino group, guanyl group, halo group, heteroarylalkoxy group, heteroarylalkyl group, heteroaiyl group, heteroarylcarbonyl group, heteroaryloxy group, heterocyclic group, hydroxamino group, hydroxy group, imino group, isocyanato group, isocyano group, mercapto group, nitro group, oxo group, perhaloalkenyl group, perhaloalkoxy group, perhaloalkyl group, perhaloalkynyl group, perhaloarylalkyl group, perhaloaryl group, perhalocycloalkyl group, phosphate group, phosphine group, phospho group, sulfate group, sulfo group, sulfonyl group, oxidized form thereof, substituted form thereof, heteroatom form thereof, or combination thereof;

wherein each R3 is independently hydrogen, "C-group", acyl group, alkenyl group, alkoxy group, alkoxycarbonyl group, alkoxycarbonyloxy group, alkoxysulfonyloxy group, alkyl group, alkylamino group, alkylaminocarbonyl group, alkylcarbonyl group, alkylcarbonyloxy group, alkylsulfonyl group, alkylsulfonyloxy group, alkylthio group, alkynyl group, amide group, amidine group, amino group, arylalkoxy group, arylalkyl group, aryl group, arylcarbonyl group, arylcarbonyloxy group, aryloxy group, aryloxycarbonyl group, aryloxycarbonyloxy group, aryloxysulfonyloxy group, arylsulfonyl group, arylsulfonyloxy group, azido group, carbamido group, carbamoyl group, carbazoyl group, carbonyl group, carboxylate group, carboxylic acid group, cyanato group, cyano group, cycloalkenyl group, cycloalkyl group, dialkylamino carbonyl group, dialkylamino group, guanidino group, guanyl group, halo group, heteroarylalkoxy group, heteroarylalkyl group, heteroaryl group, heteroarylcarbonyl group, heteroaryloxy group, heterocyclic group, hydroxamino group, hydroxy group, imino group, isocyanato group, isocyano group, mercapto group, nitro group, oxo group, perhaloalkenyl group, perhaloalkoxy group, perhaloalkyl group, perhaloalkynyl group, perhaloarylalkyl group, perhaloaryl group, perhalocycloalkyl group, phosphate group, phosphine group, phospho group, sulfate group, sulfo group, sulfonyl group, oxidized form thereof, substituted form thereof, heteroatom form thereof, or combination thereof; and wherein each R4 is independently hydrogen, "D-group", acyl group, alkenyl group, alkoxy group, alkoxycarbonyl group, alkoxycarbonyloxy group, alkoxysulfonyloxy group, alkyl group, alkylamino group, alkylaminocarbonyl group, alkylcarbonyl group, alkylcarbonyloxy group, alkylsulfonyl group, alkylsulfonyloxy group, alkylthio group, alkynyl group, amide group, amidine group, amino group, arylalkoxy group, arylalkyl group, aryl group, arylcarbonyl group, arylcarbonyloxy group, aryloxy group, aryloxycarbonyl group, aryloxycarbonyloxy group, aryloxysulfonyloxy group, arylsulfonyl group, arylsulfonyloxy group, azido group, carbamido group, carbamoyl group, carbazoyl group, carbonyl group, carboxylate group, carboxylic acid group, cyanato group, cyano group, cycloalkenyl group, cycloalkyl group, dialkylamino carbonyl group, dialkylamino group, guanidino group, guanyl group, halo group, heteroarylalkoxy group, heteroarylalkyl group, heteroaryl group, heteroarylcarbonyl group, heteroaryloxy group, heterocyclic group, hydroxamino group, hydroxy group, imino group, isocyanato group, isocyano group, mercapto group, nitro group, oxo group, perhaloalkenyl group, perhaloalkoxy group, perhaloalkyl group, perhaloalkynyl group, perhaloarylalkyl group, perhaloaryl group, perhalocycloalkyl group, phosphate group, phosphine group, phospho group, sulfate group, sulfo group, sulfonyl group, oxidized form thereof, substituted form thereof, heteroatom form thereof, or combination thereof;

or resonance form thereof, or salt thereof, or salt of resonance form thereof.

Another embodiment provides a composition, which includes the compound and a physiologically acceptable carrier.

Another embodiment provides a method, which includes administering the compound or the composition to a subject in need thereof, to treat said subject.

In some embodiments, the form of the compound is not particularly limiting. For example, it may be in a resonance form, a salt form, or salt of resonance form. Mixtures of different forms, and compositions that include mixtures of forms are possible.

In some embodiments, compound is in the salt form. In some embodiments, compound is in a resonance form. In some embodiments, the resonance form is an ionic resonance form.

In some embodiments, each R1-R4 group may independently and optionally be selected from one or more of the substituent groups described herein. In some embodiments, each R1-R4 group may independently and optionally be further substituted with one or more of the substituent groups described herein. In some embodiments, each R1-R4 group may independently and optionally connected directly to the relevant parent structure via one or more chemical bonds, or may be independently and optionally connected indirectly to the relevant parent structure via one or more divalent intervening substituent groups described herein. Combinations of 1, 2, 3, or 4 divalent intervening substituent groups are possible.

In some embodiments, R1 and R2 are each independently hydrogen, acyl group, alkenyl group, alkoxy group, alkoxycarbonyl group, alkoxycarbonyloxy group, alkoxysulfonyloxy group, alkyl group, alkylamino group, alkylaminocarbonyl group, alkylcarbonyl group, alkylcarbonyloxy group, alkylsulfonyl group, alkylsulfonyloxy group, alkylthio group, alkynyl group, amide group, amidine group, amino group, arylalkoxy group, arylalkyl group, aryl group, arylcarbonyl group, arylcarbonyloxy group, aryloxy group, aryloxycarbonyl group, aryloxycarbonyloxy group, aryloxysulfonyloxy group, arylsulfonyl group, arylsulfonyloxy group, azido group, carbamido group, carbamoyl group, carbazoyl group, carbonyl group, carboxylate group, carboxylic acid group, cyanato group, cyano group, cycloalkenyl group, cycloalkyl group, dialkylamino carbonyl group, dialkylamino group, guanidino group, guanyl group, halo group, heteroarylalkoxy group, heteroarylalkyl group, heteroaryl group, heteroarylcarbonyl group, heteroaryloxy group, heterocyclic group, hydroxamino group, hydroxy group, imino group, isocyanato group, isocyano group, mercapto group, nitro group, oxo group, perhaloalkenyl group, perhaloalkoxy group, perhaloalkyl group, perhaloalkynyl group, perhaloarylalkyl group, perhaloaryl group, perhalocycloalkyl group, phosphate group, phosphine group, phospho group, sulfate group, sulfo group, sulfonyl group, oxidized form thereof, substituted form thereof, heteroatom form thereof, or combination thereof.

In some embodiments, each R3 is independently hydrogen, "C-group", acyl group, alkenyl group, alkoxy group, alkoxycarbonyl group, alkoxycarbonyloxy group, alkoxysulfonyloxy group, alkyl group, alkylamino group, alkylaminocarbonyl group, alkylcarbonyl group, alkylcarbonyloxy group, alkylsulfonyl group, alkylsulfonyloxy group, alkylthio group, alkynyl group, amide group, amidine group, amino group, arylalkoxy group, arylalkyl group, aryl group, arylcarbonyl group, arylcarbonyloxy group, aryloxy group, aryloxycarbonyl group, aryloxycarbonyloxy group, aryloxysulfonyloxy group, arylsulfonyl group, arylsulfonyloxy group, azido group, carbamido group, carbamoyl group, carbazoyl group, carbonyl group, carboxylate group, carboxylic acid group, cyanato group, cyano group, cycloalkenyl group, cycloalkyl group, dialkylamino carbonyl group, dialkylamino group, guanidino group, guanyl group, halo group, heteroarylalkoxy group, heteroarylalkyl group, heteroaryl group, heteroarylcarbonyl group, heteroaryloxy group, heterocyclic group, hydroxamino group, hydroxy group, imino group, isocyanato group, isocyano group, mercapto group, nitro group, oxo group, perhaloalkenyl group, perhaloalkoxy group, perhaloalkyl group, perhaloalkynyl group, perhaloarylalkyl group, perhaloaryl group, perhalocycloalkyl group, phosphate group, phosphine group, phospho group, sulfate group, sulfo group, sulfonyl group, oxidized form thereof, substituted form thereof, heteroatom form thereof, or combination thereof. Each R3 group may independently and optionally be further substituted with one or more of the substituent groups described herein. In some embodiments, each R3 group may independently and optionally connected directly to the pendant group via one or more chemical bonds, or may be independently and optionally connected indirectly to the pendant group via one or more divalent intervening substituent groups described herein. Combinations of 1, 2, 3, or 4 divalent intervening substituent groups are possible.

In some embodiments, wherein when an R3 group is further substituted with a substituent group described herein, the substituent group may independently and optionally connected directly to the R3 group via one or more chemical bonds, or may be independently and optionally connected indirectly to the R3 group via one or more independent divalent intervening substituent groups described herein. Combinations of 1, 2, 3, or 4 independent divalent intervening substituent groups between the R3 group and substituent group are possible.

In some embodiments, each R4 is independently hydrogen, "D-group", acyl group, alkenyl group, alkoxy group, alkoxycarbonyl group, alkoxycarbonyloxy group, alkoxysulfonyloxy group, alkyl group, alkylamino group, alkylaminocarbonyl group, alkylcarbonyl group, alkylcarbonyloxy group, alkylsulfonyl group, alkylsulfonyloxy group, alkylthio group, alkynyl group, amide group, amidine group, amino group, arylalkoxy group, arylalkyl group, aryl group, arylcarbonyl group, arylcarboivloxy group, aryloxy group, aryloxycarbonyl group, aryloxycarbonyloxy group, aryloxysulfonyloxy group, arylsulfonyl group, arylsulfonyloxy group, azido group, carbamido group, carbamoyl group, carbazoyl group, carbonyl group, carboxylate group, carboxylic acid group, cyanato group, cyano group, cycloalkenyl group, cycloalkyl group, dialkylamino carbonyl group, dialkylamino group, guanidino group, guanyl group, halo group, heteroarylalkoxy group, heteroarylalkyl group, heteroaryl group, heteroarylcarbonyl group, heteroaryloxy group, heterocyclic group, hydroxamino group, hydroxy group, imino group, isocyanato group, isocyano group, mercapto group, nitro group, oxo group, perhaloalkenyl group, perhaloalkoxy group, perhaloalkyl group, perhaloalkynyl group, perhaloarylalkyl group, perhaloaryl group, perhalocycloalkyl group, phosphate group, phosphine group, phospho group, sulfate group, sulfo group, sulfonyl group, oxidized form thereof, substituted form thereof, heteroatom form thereof, or combination thereof. Each R4 group may independently and optionally be further substituted with one or more of the substituent groups described herein. In some embodiments, each R4 group may independently and optionally connected directly to the pendant group via one or more chemical bonds, or may be independently and optionally connected indirectly to the pendant group via one or more divalent intervening substituent groups described herein. Combinations of 1, 2, 3, or 4 divalent intervening substituent groups are possible.

In some embodiments, wherein when an R4 group is further substituted with a substituent group described herein, the substituent group may independently and optionally connected directly to the R4 group via one or more chemical bonds, or may be independently and optionally connected indirectly to the R4 group via one or more independent divalent intervening substituent groups described herein. Combinations of 1, 2, 3, or 4 independent divalent intervening substituent groups between the R4 group and substituent group are possible.

In some embodiments, R1-R4 are each independently hydrogen, an alkyl group, a cycloalkyl group, a cycloalkenyl group, a halo group, an alkenyl group, an alkynyl group, an aryl group, a hydroxy group, an acyl group, an oxo group, a mercapto group, an alkylthio group, an alkoxy group, a heterocyclic group, a heteroaryl group, a heteroarylcarbonyl group, an aryloxy group, a heteroaryloxy group, an arylalkyl group, a heteroarylalkyl group, an arylalkoxy group, a heteroarylalkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, an alkylsulfonyl group, an arylsulfonyl group, perhaloalkyl group, a perhaloalkoxy group, a perhalocycloalkyl group, a perhaloalkenyl group, a perhaloalkynyl group, a perhaloaryl group, a perhaloarylalkyl group, oxidized form thereof, substituted form thereof, heteroatom form thereof, or combination thereof.

In some embodiments, each R1-R4 group may independently and optionally be selected from one or more of hydrogen, an alkyl group, a cycloalkyl group, a cycloalkenyl group, a halo group, an alkenyl group, an alkynyl group, an aryl group, a hydroxy group, an acyl group, an oxo group, a mercapto group, an alkylthio group, an alkoxy group, a heterocyclic group, a heteroaryl group, a heteroarylcarbonyl group, an aryloxy group, a heteroaryloxy group, an arylalkyl group, a heteroarylalkyl group, an arylalkoxy group, a heteroarylalkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, an alkylsulfonyl group, an arylsulfonyl group, oxidized form thereof, substituted form thereof, heteroatom form thereof, or combination thereof.

In some embodiments, each R1-R4 group may independently and optionally be selected from one or more of hydrogen, an alkyl group, a cycloalkyl group, a cycloalkenyl group, a halo group, an alkenyl group, an alkynyl group, an aryl group, a hydroxy group, an acyl group, an alkoxy group, a heterocyclic group, a heteroaryl group, a heteroarylcarbonyl group, an aryloxy group, a heteroaryloxy group, an arylalkyl group, a heteroarylalkyl group, an arylalkoxy group, a heteroarylalkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, oxidized form thereof, substituted form thereof, heteroatom form thereof, or combination thereof.

In some embodiments, each R1-R4 group may independently and optionally be selected from one or more of hydrogen, an alkyl group, a cycloalkyl group, a cycloalkenyl group, an alkenyl group, an alkynyl group, an aryl group, an acyl group, an alkoxy group, a heterocyclic group, a heteroaryl group, a heteroarylcarbonyl group, an aryloxy group, a heteroaryloxy group, an arylalkyl group, a heteroarylalkyl group, an arylalkoxy group, a heteroarylalkoxy group, a carbamoyl group, an alkylcarbonyl group, an alkoxycarbonyl group, an alkylaminocarbonyl group, a dialkylamino carbonyl group, an arylcarbonyl group, an aryloxycarbonyl group, oxidized form thereof, substituted form thereof, heteroatom form thereof, or combination thereof.

In some embodiments, each R1-R4 group may independently and optionally be selected from one or more of hydrogen, an alkyl group, a cycloalkyl group, a cycloalkenyl group, an alkenyl group, an alkynyl group, an aryl group, a heterocyclic group, a heteroaryl group, an arylalkyl group, a heteroarylalkyl group, oxidized form thereof, substituted form thereof, heteroatom form thereof, or combination thereof.

In some embodiments, R1-R4 are each independently hydrogen, alkyl, substituted alkyl, linear alkyl, branched alkyl, allyl, substituted allyl, heteroalkyl, cycloalkyl, aryl, substituted aryl, heteroaryl, acyl, aroyl, heteroaroyl, substituted form thereof, heteroatom form thereof, or combination thereof.

In some embodiments, R1-R4 are each independently hydrogen, alkyl, substituted alkyl allyl, substituted allyl, heteroatom substituted alkyl, cycloakyl, aryl, substituted aryl, heteratom substituted aryl, heteroaryl, acyl, aroyl, heteroaroyl, substituted form thereof, heteroatom form thereof, or combination thereof.

In some embodiments, R1-R4 are each independently hydrogen, alkyl, allyl, cycloalkyl, aryl, acyl, aroyl, substituted form thereof, heteroatom form thereof, or combination thereof.

In some embodiments, each R1-R4 group may independently and optionally be substituted, unsubstituted, saturated, unsaturated, or combination thereof. If substituted, the substituent group or groups may be selected from any of those defined herein.

In some embodiments, one or more than one atom in one or more of R1-R4 is independently replaced with one or more independent heteroatom, oxidized form thereof, or combination thereof.

In some embodiments, each R1-R4 group may independently and optionally have one or more atoms replaced with one or more heteroatoms, e.g., N, O, P, S, oxidized form thereof, or combination thereof.

In some embodiments, one or more than one carbon in one or more of R1-R4 is independently replaced with one or more independent heteroatom selected from the group consisting of N, O, S, or combination thereof.

In some embodiments, one or more than one R1-R4 group may independently and optionally be further substituted, one or more than one R1-R4 group may independently and optionally connected directly to the relevant parent structure via one or more chemical bonds, or may be independently and optionally connected indirectly to the relevant parent structure via one or more divalent intervening substituent groups. 1, 2, 3, 4, and 5 independent divalent intervening substituent groups are possible, and may be any of those defined herein.

In some embodiments, one or more than one R1 group may independently and optionally be further substituted with one or more independent substituent groups described herein. In some embodiments, one or more than one R1 group may independently and optionally connected directly to the pyridine or thiazole portion via one or more chemical bonds, or may be independently and optionally connected indirectly to the pyridine or thiazole portion via one or more divalent intervening substituent groups described herein. 1, 2, 3, 4, or 5 independent divalent intervening substituent groups are possible, and may be any of those defined herein.

In some embodiments, one or more than one R2 group may independently and optionally be further substituted with one or more independent substituent groups described herein. In some embodiments, one or more than one R2 group may independently and optionally connected directly to the imidazole portion via one or more chemical bonds, or may be independently and optionally connected indirectly to the imidazole portion via one or more divalent intervening substituent groups described herein. 1, 2, 3, 4, or 5 independent divalent intervening substituent groups are possible, and may be any of those defined herein.

In some embodiments, one or more than one R3 group may independently and optionally be further substituted with one or more independent substituent groups described herein. In some embodiments, one or more than one R3 group may independently and optionally connected directly to the pendant group via one or more chemical bonds, or may be independently and optionally connected indirectly to the pendant group via one or more divalent intervening substituent groups described herein. 1, 2, 3, 4, or 5 independent divalent intervening substituent groups are possible, and may be any of those defined herein.

In some embodiments, one or more than one R4 group may independently and optionally be further substituted with one or more independent substituent groups described herein. In some embodiments, one or more than one R4 group may independently and optionally connected directly to the pendant group via one or more chemical bonds, or may be independently and optionally connected indirectly to the pendant group via one or more divalent intervening substituent groups described herein. 1, 2, 3, 4, or 5 independent divalent intervening substituent groups are possible, and may be any of those defined herein.

In some embodiments, R1 is halogen, Cl, F, Br, alkyl, alkenyl, alkynyl, alkoxy, hydroxyl, nitrile, nitro.

In some embodiments, R1 is Cl, F, Br, $C_1$-$C_4$ alkyl, $C_2$-$C_4$ alkenyl, $C_7$-$C_4$ alkynyl, $C_1$-$C_4$ alkoxy, hydroxyl, nitrile, nitro.

In some embodiments, R1 is Cl, F, or $C_4$-$C_4$ alkyl.

In some embodiments, R2 is halogen, Cl, F, Br, $CF_3$, alkyl, alkenyl, alkoxy.

In some embodiments, R2 is Cl, F, $CF_3$, $C_1$-$C_4$ alkyl, $C_2$-$C_4$ alkenyl, $C_1$-$C_4$ alkoxy. In some embodiments, R2 is Cl, F, $CF_3$, $C_1$-$C_4$ alkyl.

In some embodiments, R3 is a "C-group". In some embodiments, R3 may have one or more independent "D-group" substituents thereon. In some embodiments, R3 may include one or more independent R4 groups substituted thereon. In some embodiments, R3 may be a "C-group", and also include one or more independent R4 substituents thereon. In some embodiments, R3 may be a "C-group" and include one or more independent "D-group" substituents thereon. In some embodiments, at least one R3 is halogen.

In some embodiments, R4 is a "D" group. In some embodiments, at least one R4 is a halogen.

In some embodiments, R1 is not hydrogen. In some embodiments, R2 is not hydrogen. In some embodiments, R3 is hydrogen. In some embodiments, R4 is hydrogen.

In the following formulas:

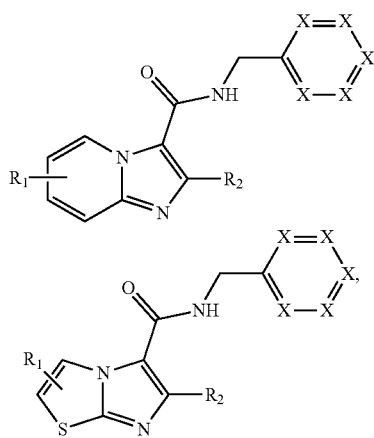

the following portion:

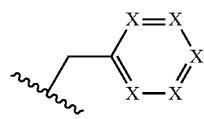

is denoted herein as the "pendant group."

In some embodiments, in the pendant group:

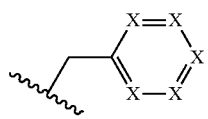

none of the X's are nitrogens. In such an embodiment, each X in the pendant group is independently C—R3 or C—R4, and if more than one C—R3 is present, they may be the same or different, and if more than one C—R4 is present, they may be the same or different. In some embodiments, no X's are C—R3. In some embodiments, no X's are C—R4. In some embodiments, both C—R4 and C—R3 are present. In some embodiments, one or more C—R3 or C—R4 group may form a ring with one or more other C—R3 group, one or more other C—R4 group, or a combination of C—R3 and C—R4 groups, to form a ring fused to the pendant group ring.

In other embodiments, in the pendant group:

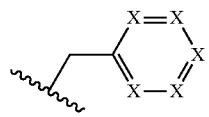

one or two X's are nitrogens, and the pendant group has one of the following structures:

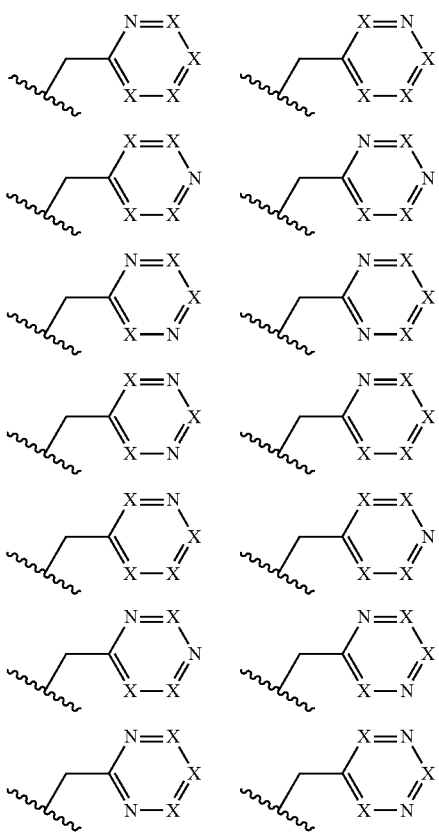

wherein each X is independently C—R3 or C—R4, and if more than one C—R3 is present, they may be the same or different, and if more than one C—R4 is present, they may be the same or different. In some embodiments, no X's are C—R3. In some embodiments, no X's are C—R4. In some embodiments, both C—R3 and C—R4 are present. In some embodiments, one or more C—R3 or C—R4 group may form a fused ring with one or more other C—R3 group, one or more other C—R4 group, or a combination of C—R3 and C—R4 groups.

In some embodiments, one or more C—R3 or C—R4 group may join and form a fused ring with one or more other C—R3 group, one or more other C—R4 group, or a combination of C—R3 and C—R4 groups.

In some embodiments, wherein one or more C—R3 or C—R4 group may join and form a fused ring with one or more other C—R3 group, one or more other C—R4 group, or a combination of C—R3 and C—R4 groups, the pendant group:

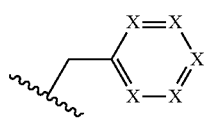

has one of the following fused ring structures:

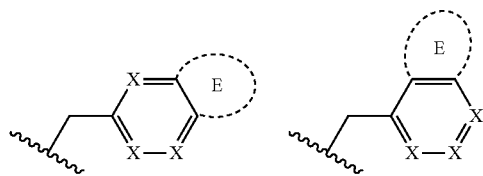

wherein each X is independently N, C—R3, or C—R4; and "E" represents a ring, shown by the dashed line, which is formed from one or more R3 or R4 group joining with one or more other R3, R4, or combination of R3 and R4 groups. The E ring may be carbocyclic or heterocyclic, saturated or unsaturated, substituted or unsubstituted. By carbocyclic it is intended that the E ring is a cycloalkane, cycloalkene, aryl, or the like. If heterocyclic, the E ring may have 1, 2 or 3 ring carbons independently replaced with one or more independent oxygen, nitrogen, sulfur or combination thereof. Counting the C—R3 and C—R4 fused carbons, the E ring may have 4-12 members, which range includes 4, 5, 6, 7, 8, 9, 10, 11, 12 members. In some embodiments, the C—R3 or C—R4 groups that form the E ring are adjacent, although they may be separated by intervening N, C—R3 or C—R4.

In some embodiments, E ring is formed by joining two adjacent independent C—R3 groups. In some embodiments, the E ring is formed by joining two adjacent independent C—R4 groups. In some embodiments, the E ring is formed by joining a C—R3 group with an adjacent C—R4 group.

In some embodiments, the E ring is a carbocyclic or heterocyclic, saturated or unsaturated, substituted or unsubstituted 5, 6, 7, or 8 membered ring. In some embodiments, the E ring is a carbocyclic or heterocyclic 5-6 membered ring, which may be saturated or unsaturated, substituted or unsubstituted. In some embodiments, it is the portion of the E ring represented by the dashed line in the above figure that is saturated or unsaturated, substituted or unsubstituted, or contains or does not contain ring heteroatoms; and it is not the E ring carbons that are common to both the fused ring and the pendant group ring.

In some embodiments, wherein an E ring is present, the pendant group has one of the following formulas:

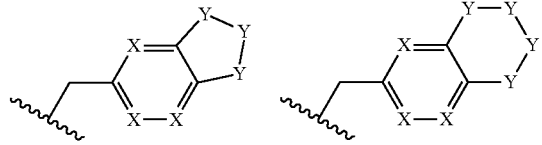

wherein each Y is independently C—R5, C(R5)(R5), C=O, N, N—R5, O, S, S=O, or S(=O)$_2$; with the proviso that no more than two Y's are C=O, N, N—R5, O, S, S=O, or S(=O)$_2$;

wherein when two adjacent Y's are each independently C—R5, or are an N and a C—R5, the bond between said adjacent Y's may be a double bond;

and wherein each R5 is independently hydrogen, "C-group", "D-Group", acyl group, alkenyl group, alkoxy group, alkoxycarbonyl group, alkoxycarbonyloxy group, alkoxysulfonyloxy group, alkyl group, alkylamino group, alkylaminocarbonyl group, alkylcarbonyl group, alkylcarbonyloxy group, alkylsulfonyl group, alkylsulfonyloxy group, alkylthio group, alkynyl group, amide group, amidine group, amino group, arylalkoxy group, arylalkyl group, aryl group, arylcarbonyl group, arylcarbonyloxy group, aryloxy group, aryloxycarbonyl group, aryloxycarbonyloxy group, aryloxysulfonyloxy group, arylsulfonyl group, arylsulfonyloxy group, azido group, carbamido group, carbamoyl group, carbazoyl group, carbonyl group, carboxylate group, carboxylic acid group, cyanato group, cyano group, cycloalkenyl group, cycloalkyl group, dialkylamino carbonyl group, dialkylamino group, guanidino group, guanyl group, halo group, heteroarylalkoxy group, heteroarylalkyl group, heteroaryl group, heteroarylcarbonyl group, heteroaryloxy group, heterocyclic group, hydroxamino group, hydroxy group, imino group, isocyanato group, isocyano group, mercapto group, nitro group, oxo group, perhaloalkenyl group, perhaloalkoxy group, perhaloalkyl group, perhaloalkynyl group, perhaloarylalkyl group, perhaloaryl group, perhalocycloalkyl group, phosphate group, phosphine group, phospho group, sulfate group, sulfo group, sulfonyl group, oxidized form thereof, substituted form thereof, heteroatom form thereof, or combination thereof.

Each R5 group may independently and optionally be further substituted with one or more of the substituent groups described herein. In some embodiments, each R5 group may independently and optionally connected directly to the E ring via one or more chemical bonds, or may be independently and optionally connected indirectly to the E ring via one or more divalent intervening substituent groups described herein. Combinations of 1, 2, 3, or 4 divalent intervening substituent groups are possible.

In some embodiments, wherein when an R5 group is further substituted with a substituent group described herein, the substituent group may independently and optionally connected directly to the R5 group via one or more chemical bonds, or may be independently and optionally connected indirectly to the R5 group via one or more independent divalent intervening substituent groups described herein. Combinations of 1, 2, 3, or 4 independent divalent intervening substituent groups between the R5 group and substituent group are possible.

In some embodiments, wherein an E ring is present, the pendant group has one of the following formulas:

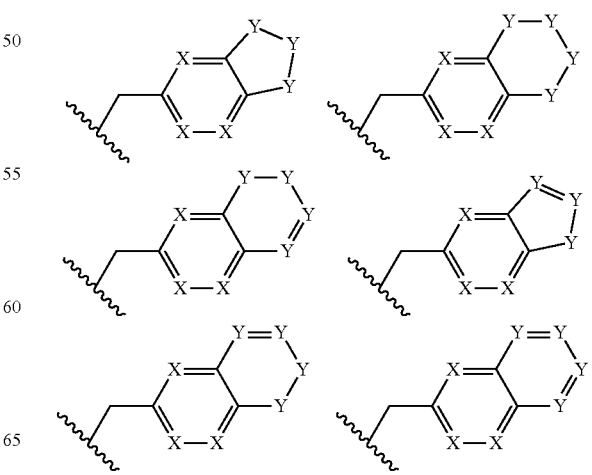

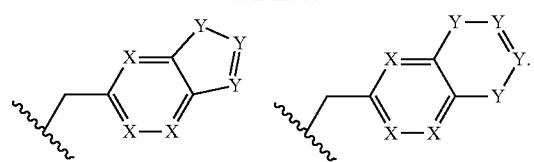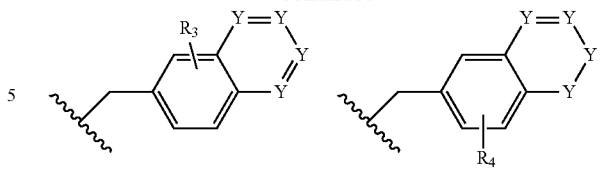
For example, the pendant group may have one of the following pendant group formulas:
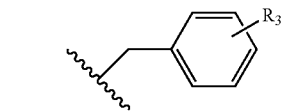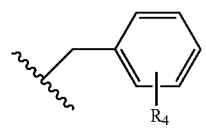
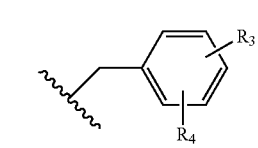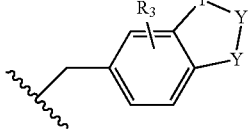
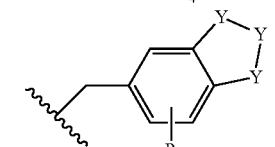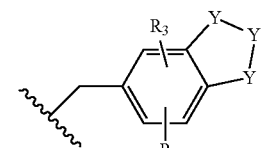
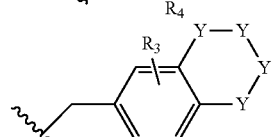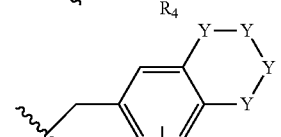
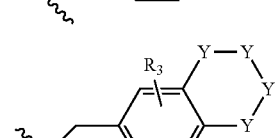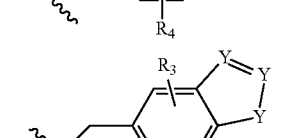
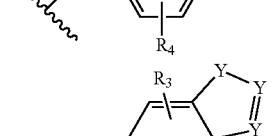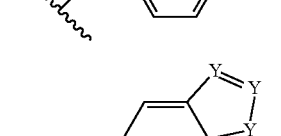
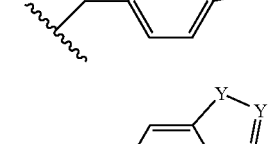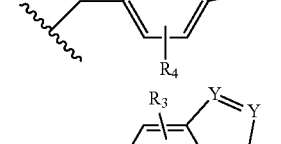
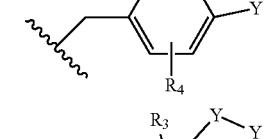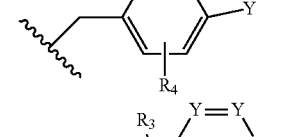
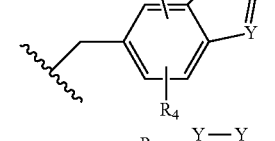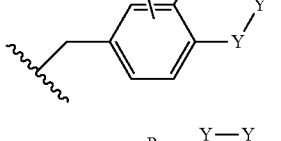
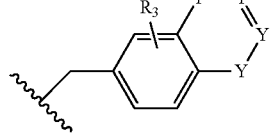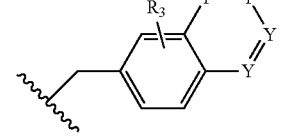
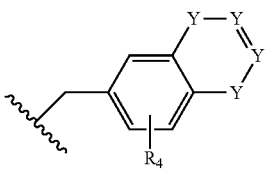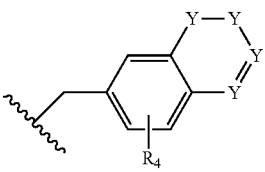
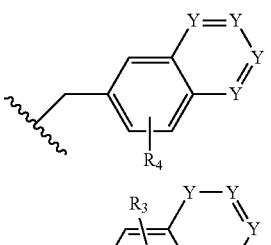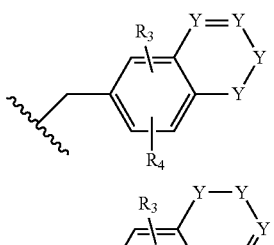
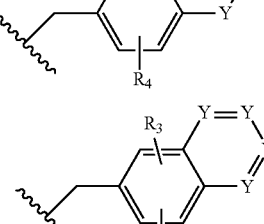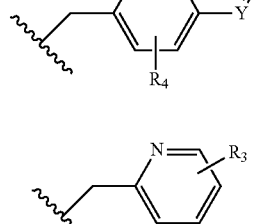
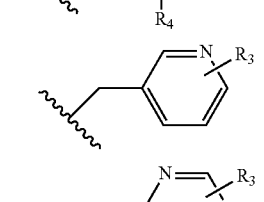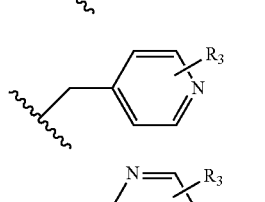
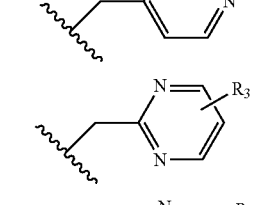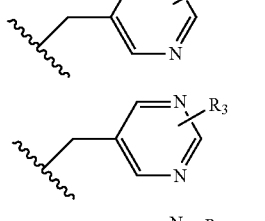
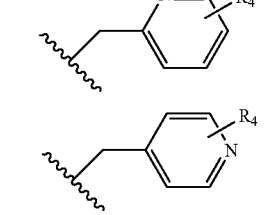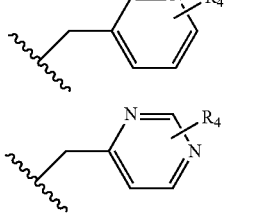
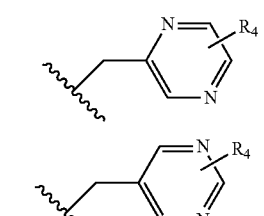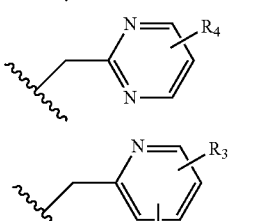

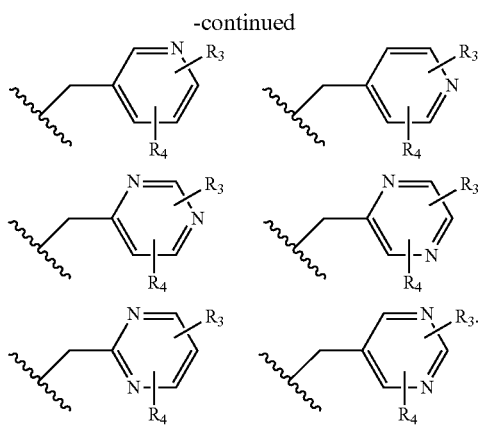

In the above pendant group formulas, the positions on the pendant group ring of the various R3 and R4 groups relative to one another, the nitrogen positions, and/or the fused ring position are not intended to be limiting. Taking one as an example, and unless otherwise specified, a structure illustrated as follows:

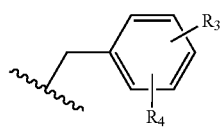

could be illustrated as follows:

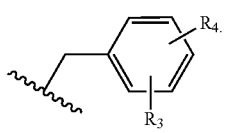

Further, in the said preceding pendant group formulas, wherein when one —R3 is shown, one or more than one —R3, each independently, may be bonded to the pendant group ring. Similarly, wherein when one —R4 is shown, one or more than one —R4, each independently, may be bonded to the pendant group ring.

In some embodiments, wherein an E ring is present, the pendant group may have one of the following formulas, wherein one or more Y's, designated below as G, are each independently selected from N, N—R5, O, S, S=O, or S(=O)$_2$:

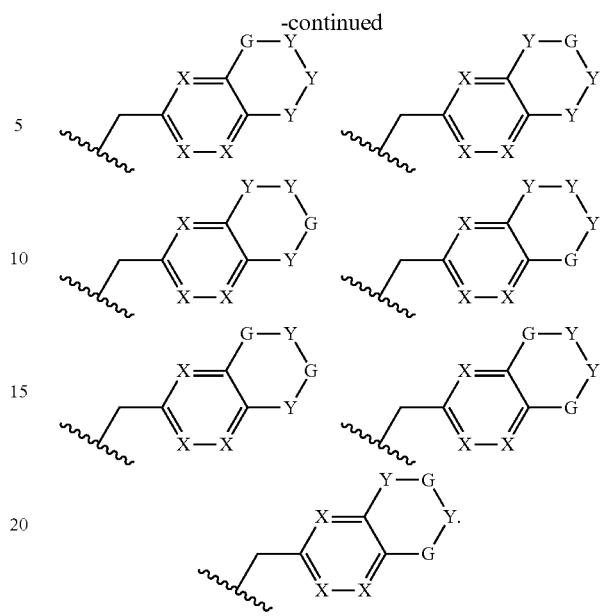

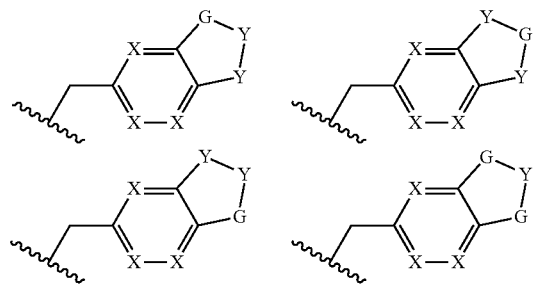

in which each of the remaining Y's, shown, is independently C—R5, C(R5)(R5), or C=O;

and wherein when two adjacent Y's are each independently C—R5, or are an N and a C—R5, the bond between said adjacent Y's may be a double bond.

In some embodiments, R3 is a group having the following formula:

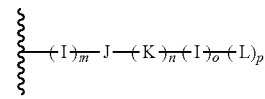

wherein I, each occurrence, is independently a divalent substituent described herein; and m is 0, 1, or 2, and o is 0, 1, or 2;

wherein J is an optionally substituted secondary amine, tertiary amine, cyclic amine, heterocycle, spiro-group-containing heterocycle, N-containing heterocycle, O-containing heterocycle, N- and O-containing heterocycle, heteroaryl, N-containing heteroaryl, aryl, oxidized form thereof, heteroatom form thereof, substituted form thereof, or combination thereof;

wherein K, each occurrence, is independently R4, aryl, heteroaryl, heterocycle, cycloalkyl, cycloalkenyl, oxidized form thereof, heteroatom form thereof, substituted form thereof, or combination thereof, and n is 0, 1, or 2;

and wherein L, each occurrence, is independently an optionally substituted R4, oxidized form thereof, heteroatom form thereof, substituted form thereof, or combination thereof; and p is 0, 1, 2, 3, 4, 5, or 6.

In some embodiments, I, each occurrence, may be independently alkylene, alkenylene, alkyleneoxy, alkenylenoxy, or alkynylene, oxidized form thereof, heteroatom form thereof, or substituted form thereof, and m is 0 or 1, and o is 0 or 1.

In some embodiments, J is an optionally substituted "C-group", tertiary amine, cyclic amine, heterocycle, N-containing heterocycle, O-containing heterocycle, N- and O-containing heterocycle, heteroaryl, N-containing heteroaryl, aryl, oxidized form thereof, heteroatom form thereof, substituted form thereof, or combination thereof.

In some embodiments, K, each occurrence, is independently an optionally substituted R4, aryl, heteroaryl, heterocycle, cycloalkyl, cycloalkenyl, oxidized form thereof, heteroatom form thereof, substituted form thereof, or combination thereof; and n is 0 or 1.

In some embodiments, L, each occurrence, is independently an optionally substituted R4 or "D-group", oxidized form thereof, heteroatom form thereof, or substituted form thereof, and p is 0, 1, 2, 3, 4, 5, or 6.

In some embodiments, wherein n, o and p are 0, then J is a univalent residue of an optionally substituted "C-group", tertiary amine, cyclic amine, heterocycle, N-containing heterocycle, O-containing heterocycle, N- and O-containing heterocycle, heteroaryl, N-containing heteroaryl, aryl, or combination thereof, but wherein any of n, o or p is not 0, then J is a divalent residue of an optionally substituted "C-group", tertiary amine, cyclic amine, heterocycle, N-containing heterocycle, O-containing heterocycle, N- and O-containing heterocycle, heteroaryl, N-containing heteroaryl, aryl, or combination thereof.

In some embodiments, wherein o and p are 0, then K is a univalent residue of an optionally substituted R4, aryl, heteroaryl, heterocycle, cycloalkyl, cyclic, or combination thereof, but wherein any of o or p is not 0, then K is a divalent residue of an optionally substituted R4, aryl, heteroaryl, heterocycle, cycloalkyl, cyclic, or combination thereof.

In some embodiments, R3 is or is substituted to include a 3, 4, 5, 6 membered ring or larger, which contains one or more of carbons, substituted carbons and/or heteroatoms (N, O, S) in addition to their oxidized versions, including alkenes and cycloalkenes, heterocycles and mixed carbocycle and heterocyclic moieties.

In some embodiments, R3 includes a cyclic amine, wherein the nitrogen and carbons form a $C_3$-$C_{10}$ cyclic amine.

In some embodiments, R3 includes a cyclic amine, wherein the nitrogen and carbons form a $C_3$-$C_6$ cyclic group.

In some embodiments, the cyclic amine has the following structure:

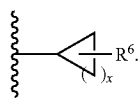

The x in the cyclic amine is not particularly limiting and may have any value. In some embodiments, x is 1-10. This range includes all values and subranges therebetween, including 1, 2, 3, 4, 5, 6, 7, 8, 9, and 10.

In some embodiments, one or more than one of the carbon atoms in the above cyclic amine structure may independently and optionally be substituted with one or more independent substituent groups described herein. In some embodiments, one or more than one carbon in the cyclic amine structure is oxidized. In some embodiments, one or more than of the substituent groups may independently and optionally connected directly to the cyclic amine structure via one or more chemical bonds, or may be independently and optionally connected indirectly to the cyclic amine structure via one or more divalent intervening substituent groups described herein. 1, 2, 3, 4, or 5 independent divalent intervening substituent groups are possible, and may be any of those defined herein. In some embodiments, one or more than one of the carbon atoms in the above cyclic amine structure are replaced with a heteroatom, such as S, O, or N. In some embodiments, the cyclic amine is selected from a "C-group."

So long as the nitrogen is present, the remaining ring portion of the cyclic amine is not particularly limiting. The remaining ring portion may be suitably derived from a divalent cycloalkylene group, divalent heterocycloalkylene group, divalent arylene group, divalent heteroarlyene group, one or more of the divalent intervening substituent groups, oxidized form thereof, or combination thereof. The cyclic amine may have one or more than one ring. Combinations of different rings are possible.

In the cyclic amine, one or more than one of the ring atoms may be optionally and independently replaced with one or more heteroatoms, e.g., N, O, P, S, oxidized form thereof, or combination thereof.

In the cyclic amine, one or more than one of the ring atoms may be optionally and independently substituted with one or more $R^6$ substituent groups. If more than one substituent group is present, they may be the same or different.

In the cyclic amine, one or more than one of the $R^6$ substituent groups may be further substituted with one or more further substituent groups. If more than one further substituent group is present, they may be the same or different.

In some embodiments, each substituent group and/or further substituent groups may independently and optionally be selected from one or more of the substituent groups described herein.

In some embodiments, each $R^6$ group may independently and optionally be selected from one or more of "D-group", hydrogen, an alkyl group, a cycloalkyl group, a cycloalkenyl group, a halo group, an alkenyl group, an alkynyl group, an aryl group, a hydroxy group, an acyl group, an oxo group, a mercapto group, an alkylthio group, an alkoxy group, a heterocyclic group, a heteroaryl group, a heteroarylcarbonyl group, an aryloxy group, a heteroaryloxy group, an arylalkyl group, a heteroarylalkyl group, an arylalkoxy group, a heteroarylalkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, an alkylsulfonyl group, an arylsulfonyl group, oxidized form thereof, heteroatom form thereof, substituted form thereof, or combination thereof.

In some embodiments, each $R^6$ group may independently and optionally be selected from one or more of "D-group", hydrogen, an alkyl group, a cycloalkyl group, a cycloalkenyl group, a halo group, an alkenyl group, an alkynyl group, an aryl group, a hydroxy group, an acyl group, an alkoxy group, a heterocyclic group, a heteroaryl group, a heteroarylcarbonyl group, an aryloxy group, a heteroaryloxy group, an arylalkyl group, a heteroarylalkyl group, an arylalkoxy group, a heteroarylalkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, oxidized form thereof, heteroatom form thereof, substituted form thereof, or combination thereof.

In some embodiments, each $R^6$ group may independently and optionally be selected from one or more of hydrogen, an alkyl group, a cycloalkyl group, a cycloalkenyl group, an alkenyl group, an alkynyl group, an aryl group, an acyl group, an alkoxy group, a heterocyclic group, a heteroaryl group, a heteroarylcarbonyl group, an aryloxy group, a heteroaryloxy group, an arylalkyl group, a heteroarylalkyl group, an arylalkoxy group, a heteroarylalkoxy group, a carbamoyl group, an alkylcarbonyl group, an alkoxycarbonyl group, an alkylaminocarbonyl group, a dialkylamino carbonyl group, an arylcarbonyl group, an aryloxycarbonyl group, oxidized form thereof, heteroatom form thereof, substituted form thereof, or combination thereof.

In some embodiments, each $R^6$ group may independently and optionally be selected from one or more of hydrogen, an alkyl group, a cycloalkyl group, a cycloalkenyl group, an alkenyl group, an alkynyl group, an aryl group, a heterocyclic group, a heteroaryl group, an arylalkyl group, a heteroarylalkyl group, oxidized form thereof, heteroatom form thereof, substituted form thereof, or combination thereof.

Each $R^6$ group may independently and optionally be further substituted, and each $R^6$ group may independently and optionally connected directly to the relevant parent structure via one or more chemical bonds, or may be independently and optionally connected indirectly to the relevant parent structure via one or more divalent intervening substituent groups.

In some embodiments, the compound has one of the following formulas:

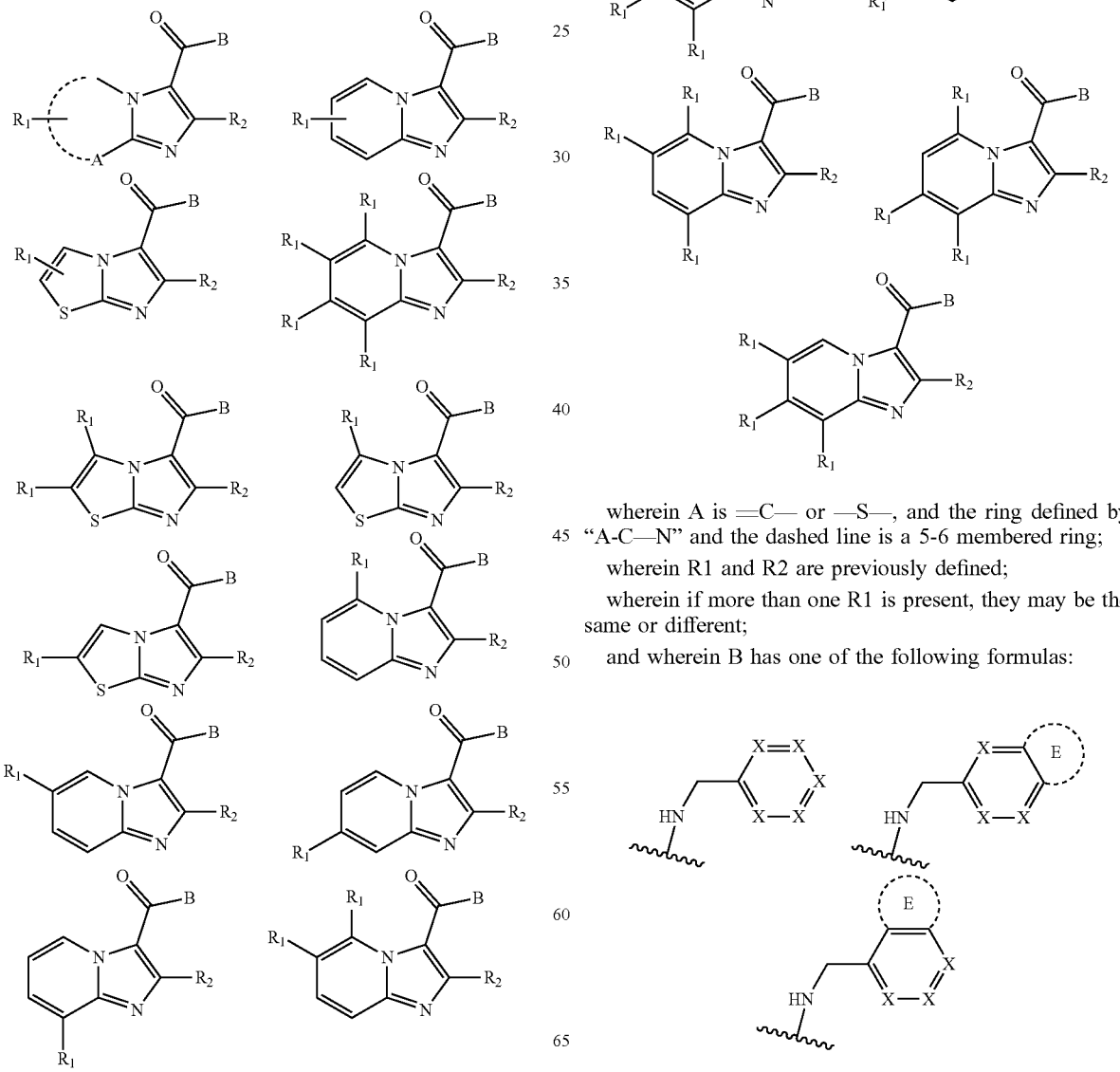

wherein A is =C— or —S—, and the ring defined by "A-C—N" and the dashed line is a 5-6 membered ring;

wherein R1 and R2 are previously defined;

wherein if more than one R1 is present, they may be the same or different;

and wherein B has one of the following formulas:

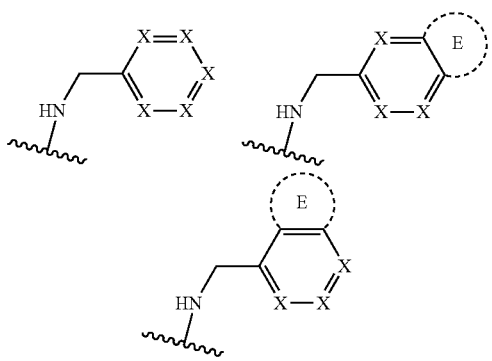

wherein X and E are previously defined.

In some embodiments, B may be benzyl amine substituted with various cycloheteroalkyls like morpholine, piperidine, piperazine, fused or substituted at various positions, which may be easily derived from a cyclic amine or substituted cyclic amine. Non-limiting examples of cyclic amines include morpholine, thiomorpholine, piperidine, piperazine, and the like, for example.

In some embodiments, B has one of the following formulas:

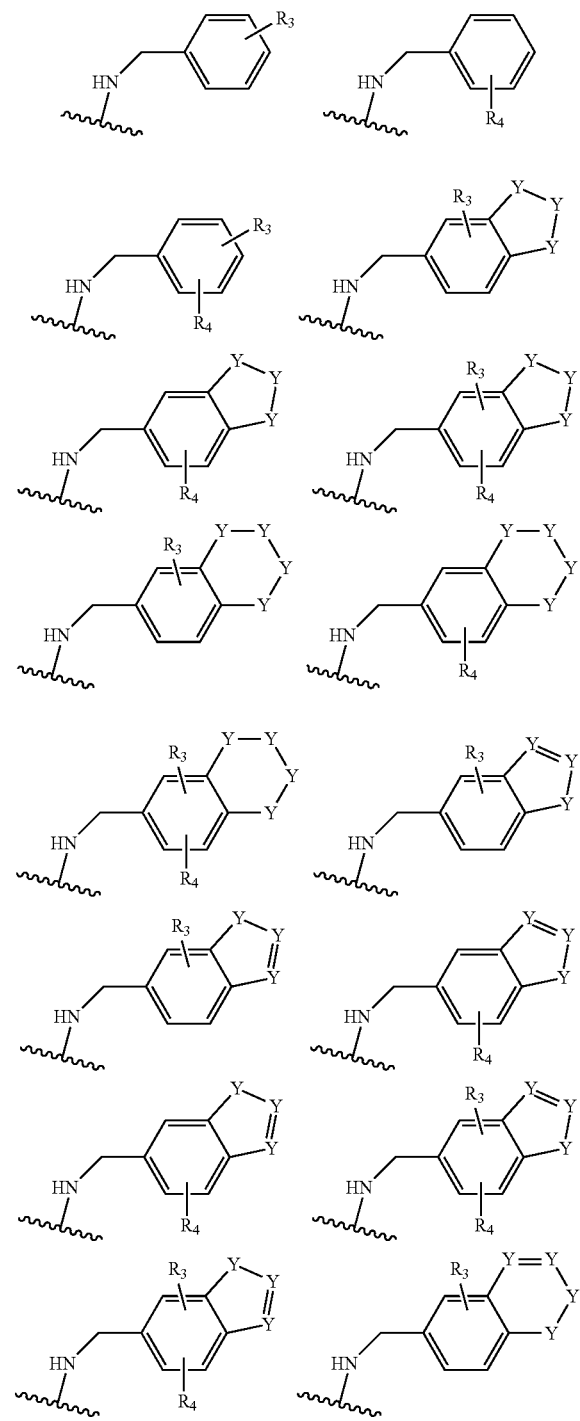
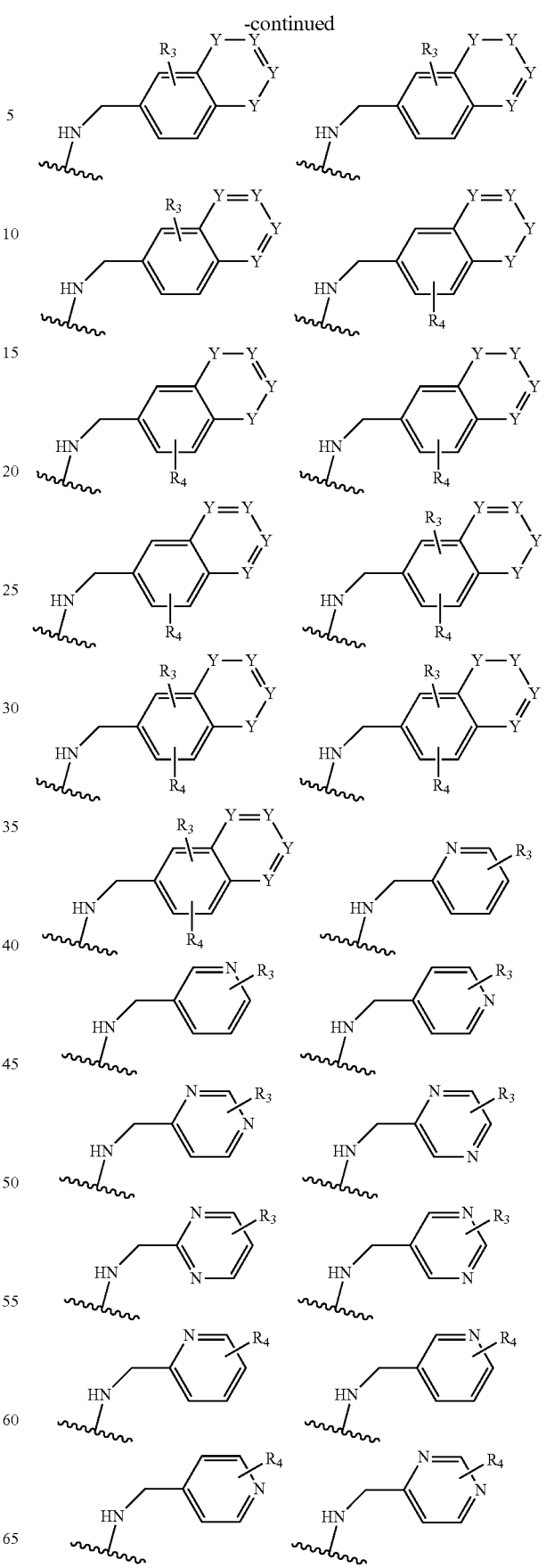

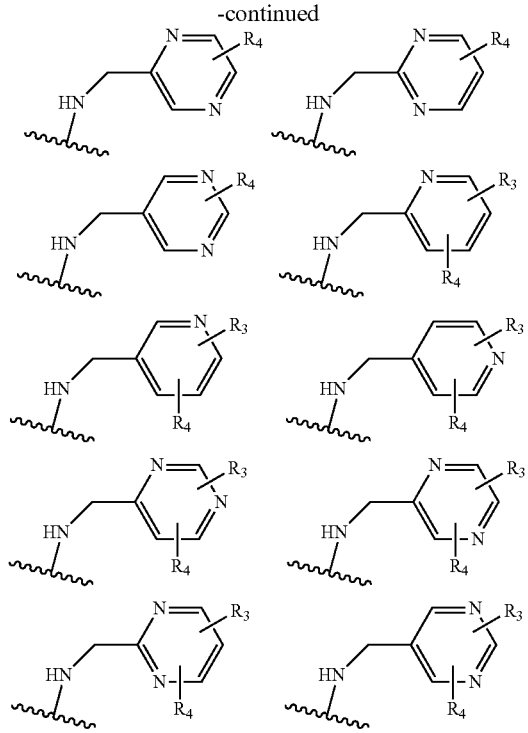
wherein R3, R4 and Y are previously defined.
Some non-limiting examples of B are shown below:
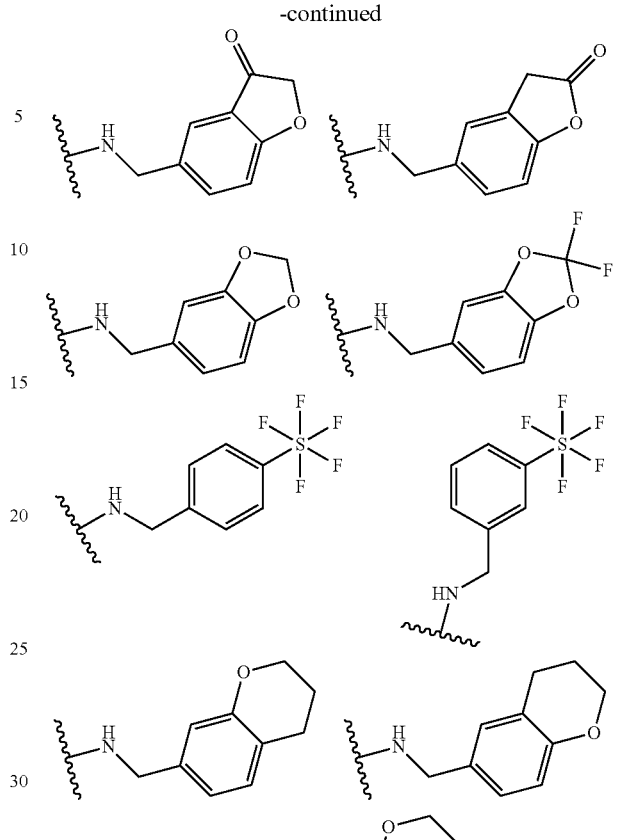
Some non-limiting examples of R3, or "C-group" are shown below:
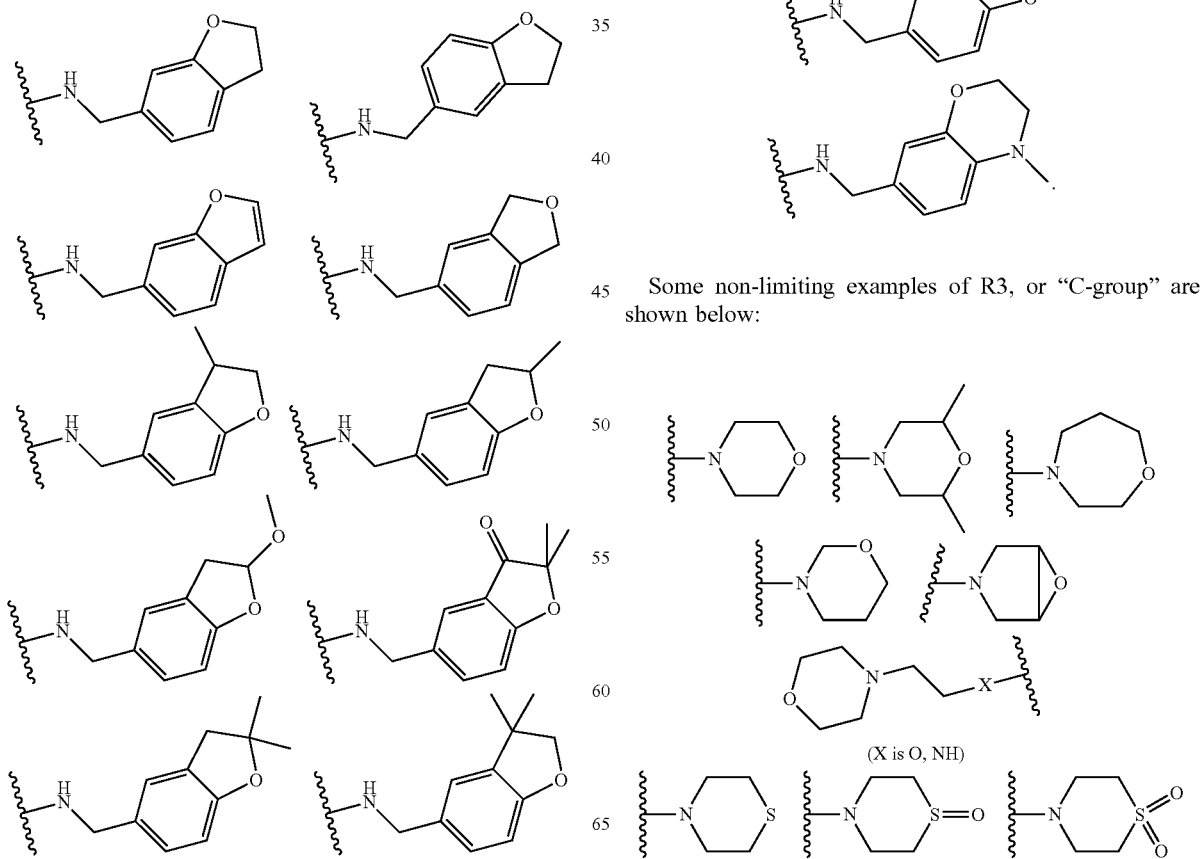
(X is O, NH)

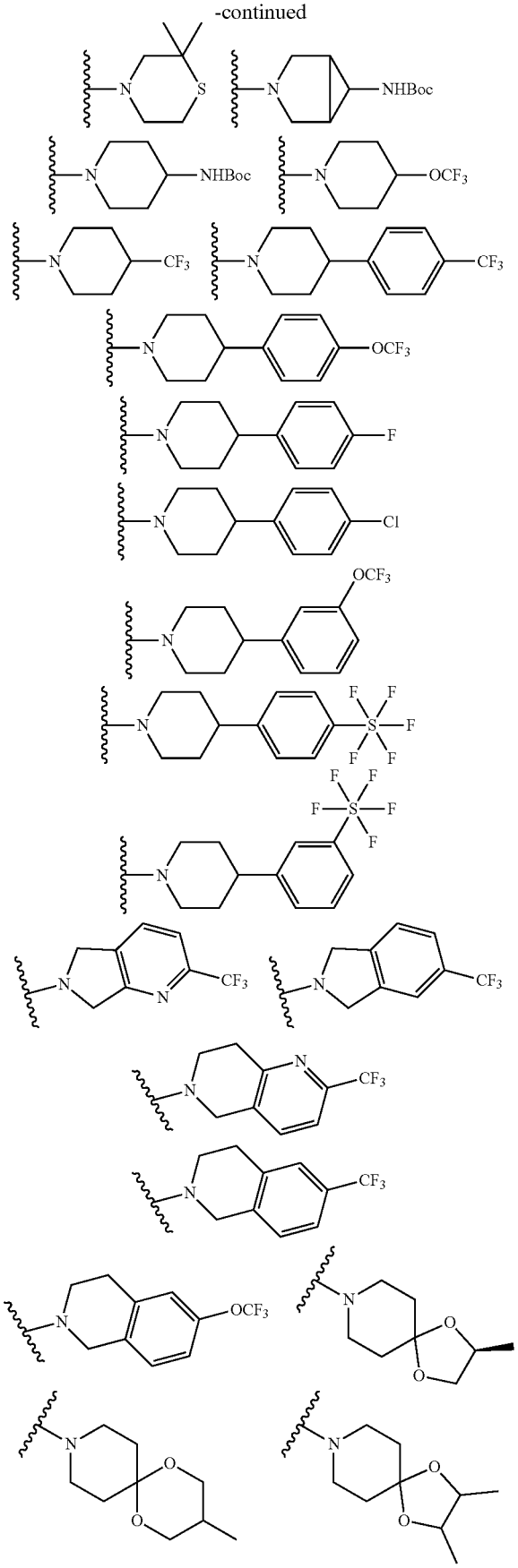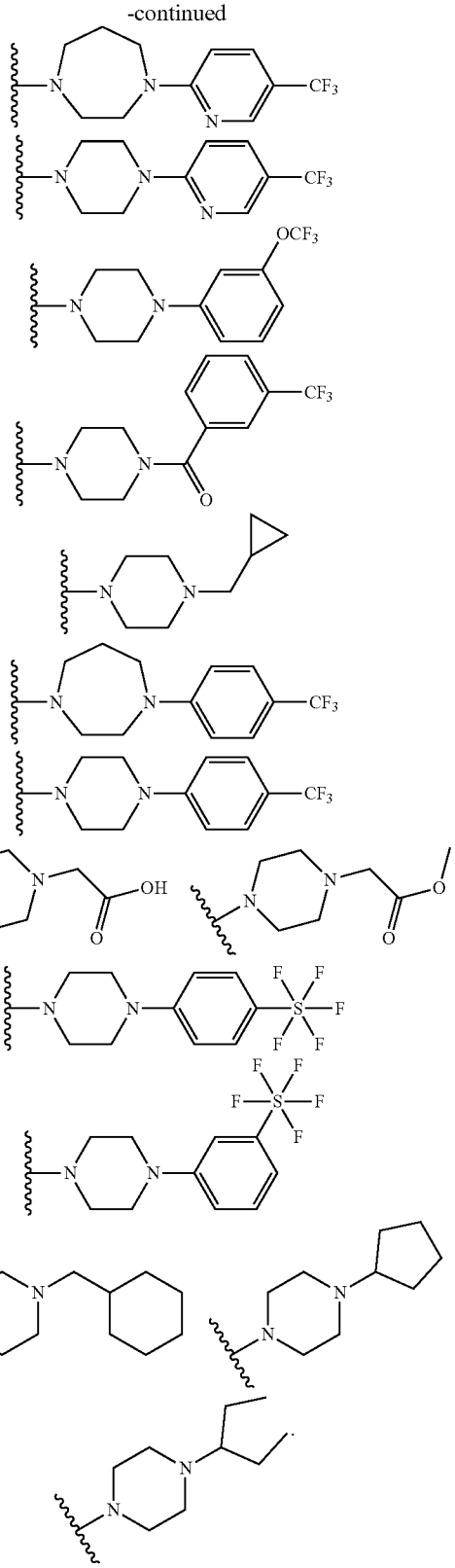
In some embodiments, a "D-group" is hydrogen, halogen, Cl, F, $CH_3$, $CH_2CH_3$, $OCH_3$, $OCH_2CH_3$, $CF_3$, $OCF_3$, $SF_5$.
In some embodiments, a "D-group" is Cl, F, $CH_3$, CN, $CF_3$, $OCF_3$, $SF_5$.

In some embodiments, a "D-group" is F, $CH_3$, CN, $CF_3$, $OCF_3$, $SF_5$.

In some embodiments, an alkyl group is a univalent, acyclic, straight or branched, substituted or unsubstituted, saturated or unsaturated, hydrocarbon radical. In some embodiments, the alkyl group has the general folinula (notwithstanding optional unsaturation, substitution or the like) —$C_nH_{2n+1}$. In some embodiments, n is 1-20 (($C_1$-$C_{20}$) alkyl), which may suitably include $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ alkyl groups. In some embodiments, the alkyl group may be straight or branched, substituted or unsubstituted, saturated or unsaturated, or any combination thereof. In some embodiments, one or more hydrogens may be optionally and independently replaced by one or more substituent groups. In some embodiments, one or more carbon atoms may be optionally and independently replaced with one or more heteroatoms such as O, S, N, B, or any combination thereof. In some embodiments, the alkyl group may contain one or more double bond, one or more triple bond, or any combination thereof. In some embodiments, the alkyl group is attached to the parent structure through one or more independent divalent intervening substituent groups. Some examples of alkyl groups, which are not intended to be limiting, include methyl, ethyl, n-propyl, isopropyl, n-butyl, iso-butyl, secondary-butyl, tertiary-butyl, and the like.

In some embodiments, a cycloalkyl group is a univalent, mono- or polycyclic, substituted or unsubstituted, saturated or unsaturated hydrocarbon radical. In some embodiments, the cycloalkyl group has the general formula (notwithstanding optional unsaturation, substitution, or the like) —$C_nH_{2n-1}$. In some embodiments, n is 3-20 (($C_3$-$C_{20}$) cycloalkyl), which may suitably include $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ cycloalkyl groups. In some embodiments, the cycloalkyl group is substituted or unsubstituted, saturated or unsaturated, mono-, bi-, tri-, or poly-cyclic, or any combination thereof. In some embodiments, one or more hydrogens may be optionally and independently replaced by one or more substituent groups. In some embodiments, the cycloalkyl group may have one or more sites of unsaturation, e.g., it may contain one or more double bond, one or more triple bond, or any combination thereof to form a cycloalkenyl or cycloalkynyl group, or combination thereof. In some embodiments, one or more carbon atoms may be optionally and independently replaced with one or more heteroatoms such as O, S, N, B, or any combination thereof. In some embodiments, the cycloalkyl group is attached to the parent structure through one or more independent divalent intervening substituent groups. Some examples of cycloalkyl groups, which are not intended to be limiting, include cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, and the like. In the case of polycyclic groups, one or more of the rings may be tethered together via bond or other divalent intervening substituent group, fused (e.g., in which one or more rings shares two or more carbon atoms or heteroatoms, joined via a single atom (e.g., Spiro compound), or bridged.

In some embodiments, an alkenyl group is a univalent, straight or branched, substituted or unsubstituted, unsaturated hydrocarbon radical. In some embodiments, the alkenyl group has the general formula (notwithstanding optional substitution, higher degree of unsaturation, or the like) —$C_nH_{2n+2}$. In some embodiments, n is 2-20 (($C_2$-$C_{20}$) alkenyl), which may suitably include $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ alkenyl groups. In some embodiments, the alkenyl group may be straight or branched, substituted or unsubstituted, have more than one degree of unsaturation, or any combination thereof. In some embodiments, one or more carbon atoms may be optionally and independently replaced with one or more heteroatoms such as O, S, N, B, or any combination thereof. In some embodiments, the alkenyl group is attached to the parent structure through one or more independent divalent intervening substituent groups. Some examples of alkenyl groups, which are not intended to be limiting, include ethenyl, 1-propenyl, 2-propenyl (allyl), iso-propenyl, 2-methyl-1-propenyl, 1-butenyl, 2-butenyl, alkadienes, alkatrienes, and the like.

In some embodiments, an alkynyl group is a univalent, straight or branched, substituted or unsubstituted, hydrocarbon radical that contains one or more carbon-carbon triple bond. In some embodiments, the alkenyl group has the general formula (notwithstanding optional substitution, higher degree of unsaturation, or the like) —$C_nH_{2n-3}$. In some embodiments, n is 2-20 (($C_2$-$C_{20}$) alkynyl), which may suitably include $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ alkynyl groups. In some embodiments, the alkynyl group may be straight or branched, substituted or unsubstituted, have more than one degree of unsaturation, or any combination thereof. In some embodiments, one or more carbon atoms may be optionally and independently replaced with one or more heteroatoms such as O, S, N, B, or any combination thereof. In some embodiments, the alkynyl group is attached to the parent structure through one or more independent divalent intervening substituent groups. Some examples of alkynyl groups, which are not intended to be limiting, include alkadiynes, alkatriynes, ethynyl, propynyl, butynyl, and the like.

In some embodiments, an aryl group is a univalent, substituted or unsubstituted, monocyclic or polycyclic aromatic hydrocarbon radical. In some embodiments, an aryl group is a radical which, in accordance with Hückel's threory, includes a cyclic, delocalized (4n+2) pi-electron system. In some embodiments the aryl group is a $C_5$-$C_{20}$ aryl group. The $C_5$-$C_2O$ aryl group may suitably include $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ aryl groups. In some embodiments, the aryl group may be substituted or unsubstituted, be substituted with two or more groups that taken together form a cyclic group, or any combination thereof. In some embodiments, the aryl group is attached to the parent structure through one or more independent divalent intervening substituent groups. Some examples of aryl groups, which are not intended to be limiting, include phenyl, naphthyl, tetrahydronaphthyl, phenanthryl, pyrenyl, anthryl, indanyl, chrysyl, and the like.

In some embodiments, a heterocyclic group is a univalent, substituted or unsubstituted, saturated or unsaturated, mono- or polycyclic hydrocarbon radical that contains one or more heteroatoms in one or more of the rings. In some embodiments, the heterocyclic group is a $C_3$-$C_{20}$ cyclic group, in which one or more ring carbons is independently replaced with one or more heteroatoms. The $C_3$-$C_{20}$ heterocyclic group may suitably include $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ cyclic groups in which one or more ring carbons is independently replaced with one or more heteroatoms. In some embodiments, the heteroatoms are selected from one or more of N, O, or S, or any combination thereof. In some embodiments, the N or S or both may be independently substituted with one or more substituents. In some embodiments, the heterocyclic group is substituted or unsubstituted, saturated or unsaturated, mono-, bi-, tri-, or poly-cyclic, or any combination thereof. In some embodiments, one or more hydrogens may be optionally and independently replaced by one or more substituent groups. In some embodiments, the heterocyclic group may include one or more carbon-carbon double bonds, carbon-carbon triple bonds, carbon-nitrogen double bonds, or any combination thereof. In some embodiments, the heterocyclic group is attached to the parent structure through one or more independent divalent intervening substituent groups. Some examples of heterocyclic groups, which are not intended to be limiting, include cyclic amine, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl, tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, 1,4-oxazin-2-yl, 1,2,5-oxathiazin-4-yl, and the like In some embodiments, a heteroaryl group is univalent, substituted or unsubstituted, monocyclic or polycyclic aromatic hydrocarbon radical in which one or more ring carbons is independently replaced with one or more heteroatoms selected from O, S and N. In some embodiments, in addition to said heteroatom, the heteroaryl group may optionally have up to 1, 2, 3, or 4 N atoms in the ring. In some embodiments, the heteroaryl group is an aryl group in which one or more ring carbons are independently replaced with one or more heteroatoms. In some embodiments, a heteroaryl group is an aromatic radical, which contains one or more heteroatoms and which, in accordance with Hückel's threory, includes a cyclic, delocalized (4n+2) pi-electron system. In some embodiments, the heteroaryl group is a $C_5$-$C_{20}$ heteroaryl group. The $C_5$-$C_{20}$ heteroaryl group may suitably include $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ aryl groups in which one or more than one ring carbon is independently replaced with one or more heteroatoms. In some embodiments, the heteroaryl group may be substituted or unsubstituted, be substituted with two or more groups that taken together form a cyclic group, or any combination thereof. In some embodiments, the heteroaryl group is attached to the parent structure through one or more independent divalent intervening substituent groups. Some examples of heteroaryl groups, which are not intended to be limiting, include heteroaryl group includes pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofinyl, indolyl, and the like.

In some embodiments, alkylene, cycloalkylene, alkenylene, alkynylene, arylene, heteroarylene groups are divalent radicals derived from the removal of a hydrogen from the respective alkyl, cycloalkyl, alkenyl, alkynyl, arylene, and heteroarylene groups, and the like.

In some embodiments, an arylalkyl group is a univalent radical derived from one or more aryl groups attached to one or more of an alkylene group, cycloalkylene group, alkenylene group, alkynylene group, or combination thereof. The alkylene, cycloalkylene, alkenylene, and alkynylene groups are divalent radicals derived from the removal of hydrogen from the respective alkyl, cycloalkyl, alkenyl, or alkynyl groups. In this context, any combination of aryl group and alkyl, cycloalkyl, alkenyl, or alkynyl group is contemplated. In some embodiments, the aryl group is attached to the parent structure through one or more of the alkylene group, cycloalkylene group, alkenylene group, alkynylene group, or combination thereof as appropriate. In some embodiments, the arylalkyl group may be attached to the parent structure through one or more independent divalent intervening substituent groups.

In some embodiments, a heteroarylalkyl group is a univalent radical derived from one or more heteroaryl groups attached to one or more of an alkylene group, cycloalkylene group, alkenylene group, alkynylene group, or combination thereof. The alkylene, cycloalkylene, alkenylene, and alkynylene groups are divalent radicals derived from the removal of hydrogen from the respective alkyl, cycloalkyl, alkenyl, or alkynyl groups. In this context, any combination of heteroaryl group and alkyl, cycloalkyl, alkenyl, or alkynyl group is contemplated. In some embodiments, the heteroaryl group is attached to the parent structure through one or more of the alkylene group, cycloalkylene group, alkenylene group, alkynylene group, or combination thereof as appropriate. In some embodiments, the heteroarylalkyl group may be attached to the parent structure through one or more independent divalent intervening substituent groups.

In some embodiments, a halo group is a univalent halogen radical or halogen-containing substituent group, e.g., one that is or contains one or more F, Br, Cl, I, or combination thereof. As used herein, the term "halogen" or "halo" includes fluoro, Moro, bromo, or iodo, or fluoride, chloride, bromide or iodide. In some embodiments, a halogen containing substituent group may suitably include a substituent group in which one or more hydrogen atoms are independently replaced with one or more halogens. In some embodiments, the halo group may be attached to the parent structure through one or more independent divalent intervening substituent groups.

In some embodiments, a hydroxy group is a univalent hydroxyl radical (—OH) or hydroxy-containing substituent group, e.g., one that is or contains one or more —OH. As used herein the term, "hydroxy" includes an —OH group. In some embodiments, a hydroxy-containing substituent group may suitably include a substituent group in which one or more hydrogen atoms are independently replaced with one or more —OH groups. In some embodiments, the hydroxyl group may be attached to the parent structure through one or more independent divalent intervening substituent groups.

In some embodiments, an oxo group is a univalent radical that contains an oxygen atom, =O, doubly bonded to carbon or another element. In some embodiments, an oxo group is a divalent radical that contains an oxygen atom, —O—, bonded to two carbons or two other elements. In some embodiments, the oxo group suitably includes aldehydes, carboxylic acids, ketones, sulfonic acids, amides, esters, and combinations thereof. In some embodiments, the oxo group may be attached to the parent structure through one or more independent divalent intervening substituent groups.

In some embodiments, a mercapto or thiol group is a univalent —SR radical or an —SR-containing group. The R group is suitably chosen from any of the substituent groups.

In some embodiments, the mercapto group may be attached to the parent structure through one or more independent divalent intervening substituent groups.

In some embodiments, an amino group is a univalent —NH$_2$ radical or an —NH$_2$-containing substituent group. In some embodiments, the amino group may be attached to the parent structure through one or more independent divalent intervening substituent groups.

In some embodiments, an alkylamino group is a univalent —NRH radical or an —NRH-containing substituent group. The R group is suitably chosen from any of the substituent groups. In some embodiments, the alkylamino group may be attached to the parent structure through one or more independent divalent intervening substituent groups.

In some embodiments, a dialkylamino group is a univalent —NRR radical or an —NRR-containing substituent group. The R groups may be the same or different and are suitably and independently chosen from any of the substituent groups. In some embodiments, the dialkylamino group may be attached to the parent structure through one or more independent divalent intervening substituent groups.

In some embodiments, an acyl or carbonyl group is a univalent radical that contains a —C(=O)R group. In some embodiments, the acyl group suitably includes aldehydes, ketones, and combinations thereof. The R group is suitably chosen from any of the substituent groups. In some embodiments, the carbonyl group may be attached to the parent structure through one or more independent divalent intervening substituent groups.

In some embodiments, a carboxylic acid group is a univalent —C(=O)OH radical or a —C(=O)OH-containing substituent group. In some embodiments, the carboxylic acid group may be attached to the parent structure through one or more independent divalent intervening substituent groups.

In some embodiments, a carboxylate group is a univalent —C(=O)O$^-$ anion, —C(=O)OR, or —C(=O)OM, wherein M is a metal cation, or —C(=O)O$^-$ anion, —C(=O)OR, or —C(=O)OM-containing substituent group. The R group is suitably chosen from any of the substituent groups. The metal cation is suitably chosen from Li, Na, K, and the like. In some embodiments, the carboxylate group may be attached to the parent structure through one or more independent divalent intervening substituent groups.

In some embodiments, an amidine group is a univalent —C(=NR)NRR radical or a —C(=NR)NRR-containing substituent group. The R groups may be the same or different and are suitably and independently chosen from any of the substituent groups. In some embodiments, the amidine group may be attached to the parent structure through one or more independent divalent intervening substituent groups.

In some embodiments, an amide group is a univalent -E(=O)NRR radical or a -E(=O)NRR-containing substituent group, in which E may be other than carbon, e.g., a chalcogen (e.g., S, Se, Te), or P. In some embodiments, the amide group suitably includes univalent lactams, peptides, phosphoramides, or sulfamides, —S(=O)$_2$NRR, —P(=O)(OH)NRR, and the like. The R groups may be the same or different and are suitably and independently chosen from any of the substituent groups. In some embodiments, the amide group may be attached to the parent structure through one or more independent divalent intervening substituent groups.

In some embodiments, a carbamoyl group is a univalent —C(=O)NRR radical or a —C(=O)NRR-containing substituent group. The R groups may be the same or different and are suitably and independently chosen from any of the substituent groups. In some embodiments, the carbamoyl group may be attached to the parent structure through one or more independent divalent intervening substituent groups.

In some embodiments, a sulfonyl group is a univalent —S(=O)$_2$R radical or a —S(=O)$_2$R-containing substituent group. The R group is suitably chosen from any of the substituent groups. In some embodiments, the sulfonyl group may be attached to the parent structure through one or more independent divalent intervening substituent groups.

In some embodiments, an alkylthio or sulfide group is a univalent —SR radical or an —SR-containing substituent group. The R group is suitably chosen from any of the substituent groups. In some embodiments, the alkylthio group may be attached to the parent structure through one or more independent divalent intervening substituent groups.

In some embodiments, an alkoxy group is a univalent radical derived from an —O-alkyl group. In some embodiments, the alkylthio group may be attached to the parent structure through one or more independent divalent intervening substituent groups.

In some embodiments, an aryloxy group is a univalent radical derived from an —O-aryl group. In some embodiments, the aryloxy group may be attached to the parent structure through one or more independent divalent intervening substituent groups.

In some embodiments, a heteroaryloxy group is a univalent radical derived from an —O-heteroaryl group. In some embodiments, the heteroaryloxy group may be attached to the parent structure through one or more independent divalent intervening substituent groups.

In some embodiments, an arylalkoxy group is a univalent radical derived from an —O-arylalkyl group. In some embodiments, the arylalkoxy group may be attached to the parent structure through one or more independent divalent intervening substituent groups.

In some embodiments, a heteroarylalkoxy group is a univalent radical derived from an —O-heteroaryl group. In some embodiments, the heteroarylalkoxy group may be attached to the parent structure through one or more independent divalent intervening substituent groups.

In some embodiments, an alkylcarbonyl group is a univalent is radical derived from a -carbonyl-alkyl group. In some embodiments, the alkylcarbonyl group may be attached to the parent structure through one or more independent divalent intervening substituent groups.

In some embodiments, an alkoxycarbonyl group is a univalent radical derived from a -carbonyl-O-alkyl group. In some embodiments, the alkoxycarbonyl group may be attached to the parent structure through one or more independent divalent intervening substituent groups.

In some embodiments, an alkylaminocarbonyl group is a univalent radical derived from a -carbonyl-alkylamino group. In some embodiments, the heteroarylalkoxy group may be attached to the parent structure through one or more independent divalent intervening substituent groups.

In some embodiments, a dialkylamino carbonyl group is a univalent radical derived from a -carbonyl-dialkylamino group. In some embodiments, the dialkylamino carbonyl group may be attached to the parent structure through one or more independent divalent intervening substituent groups.

In some embodiments, an arylcarbonyl group is a univalent radical derived from a -carbonyl-aryl group. In some embodiments, the arylcarbonyl group may be attached to the parent structure through one or more independent divalent intervening substituent groups.

In some embodiments, a heteroarylcarbonyl group is a univalent radical derived from a -carbonyl-heteroaryl group. In some embodiments, the heteroarylcarbonyl group may be attached to the parent structure through one or more independent divalent intervening substituent groups.

In some embodiments, an aryloxycarbonyl group is a univalent radical derived from a -carbonyl-O-aryl group. In some embodiments, the aryloxycarbonyl group may be attached to the parent structure through one or more independent divalent intervening substituent groups.

In some embodiments, an alkylsulfonyl group is a univalent radical derived from a -sulfonyl-alkyl group. In some embodiments, the alkylsulfonyl group may be attached to the parent structure through one or more independent divalent intervening substituent groups.

In some embodiments, an arylsulfonyl group is a univalent radical derived from a -sulfonyl-aryl group. In some embodiments, the arylsulfonyl group may be attached to the parent structure through one or more independent divalent intervening substituent groups.

In some embodiments, a perhaloalkyl group is a univalent radical derived from a completely or substantially completely halogenated alkyl group. In some embodiments, the parhaloalkyl group may be attached to the parent structure through one or more independent divalent intervening substituent groups.

In some embodiments, a perhaloalkoxy group is a univalent radical derived from a completely or substantially completely halogenated alkoxy group. In some embodiments, the arylsulfonyl group may be attached to the parent structure through one or more independent divalent intervening substituent groups.

In some embodiments, a perhalocycloalkyl group is a univalent radical derived from a completely or substantially completely halogenated cycloalkyl group. In some embodiments, the perhalocycloalkyl group may be attached to the parent structure through one or more independent divalent intervening substituent groups.

In some embodiments, a perhaloalkenyl group is a univalent radical derived from a completely or substantially completely halogenated alkenyl group. In some embodiments, the perhaloalkenyl group may be attached to the parent structure through one or more independent divalent intervening substituent groups.

In some embodiments, a perhaloalkynyl group is a univalent radical derived from a completely or substantially completely halogenated alkynyl group. In some embodiments, the perhaloalkynyl group may be attached to the parent structure through one or more independent divalent intervening substituent groups.

In some embodiments, a perhaloaryl group is a univalent radical derived from a completely or substantially completely halogenated aryl group. In some embodiments, the perhaloaryl group may be attached to the parent structure through one or more independent divalent intervening substituent groups.

In some embodiments, a perhaloarylalkyl group is a univalent radical derived from a completely or substantially completely halogenated arylalkyl group. In some embodiments, the perhaloarylalkyl group may be attached to the parent structure through one or more independent divalent intervening substituent groups.

In some embodiments, referring to the replacement of one or more than one atom in each group with one or more heteroatoms, the heteroatoms may be suitably chosen from N, O, P, S, B, or any combination thereof.

The substituent groups are not particularly limiting. In some embodiments, the substituent group may be suitably and independently chosen from one or more of an acyl group, alkenyl group, alkoxy group, alkoxycarbonyl group, alkoxycarbonyloxy group, alkoxysulfonyloxy group, alkyl group, alkylamino group, alkylaminocarbonyl group, alkylcarbonyl group, alkylcarbonyloxy group, alkylsulfonyl group, alkylsulfonyloxy group, alkylthio group, alkynyl group, amide group, amidine group, amino group, arylalkoxy group, arylalkyl group, aryl group, arylcarbonyl group, arylcarbonyloxy group, aryloxy group, aryloxycarbonyl group, aryloxycarbonyloxy group, aryloxysulfonyloxy group, arylsulfonyl group, arylsulfonyloxy group, azido group, carbamido group, carbamoyl group, carbazoyl group, carbonyl group, carboxylate group, carboxylic acid group, cyanato group, cyano group, cycloalkenyl group, cycloalkyl group, dialkylamino carbonyl group, dialkylamino group, guanidino group, guanyl group, halo group, heteroarylalkoxy group, heteroarylalkyl group, heteroaryl group, heteroarylcarbonyl group, heteroaryloxy group, heterocyclic group, hydroxamino group, hydroxy group, imino group, isocyanato group, isocyano group, mercapto group, nitro group, oxo group, perhaloalkenyl group, perhaloalkoxy group, perhaloalkyl group, perhaloalkynyl group, perhaloarylalkyl group, perhaloaryl group, perhalocycloalkyl group, phosphate group, phosphine group, phospho group, sulfate group, sulfo group, sulfonyl group, oxidized form thereof, or combination thereof. Oxidized forms of the groups are possible. In some embodiments, the substituent group may be optionally and independently directly connected to the relevant parent structure via one or more chemical bonds. In some embodiments, the substituent group may be optionally and independently indirectly connected to the relevant parent structure via one or more divalent intervening substituent groups. In some embodiments, the substituent group may be optionally and independently further substituted with one or more substituent group.

The divalent intervening substituent groups are not particularly limiting. In some embodiments, the divalent intervening substituent group may be suitably and independently chosen from one or more of an azo group, azino group, azoxy group, carbonyl group, dioyl group, diazoamino group, disulfinyl group, dithio group, oxy group, hydrazo group, oxalyl group, sulfonyl group, thiocarbonyl group, thionyl group, phosphono ester group, carboxylate group, thio group; divalent residue of one or more of the following groups: acyl group, alkenyl group, alkoxy group, alkoxycarbonyl group, alkoxycarbonyloxy group, alkoxysulfonyloxy group, alkyl group, alkylamino group, alkylaminocarbonyl group, alkylcarbonyl group, alkylcarbonyloxy group, alkylsulfonyl group, alkylsulfonyloxy group, alkylthio group, alkynyl group, amide group, amidine group, amino group, arylalkoxy group, arylalkyl group, aryl group, arylcarbonyl group, arylcarbonyloxy group, aryloxy group, aryloxycarbonyl group, aryloxycarbonyloxy group, aryloxysulfonyloxy group, arylsulfonyl group, arylsulfonyloxy group, azido group, carbamido group, carbamoyl group, carbazoyl group, carbonyl group, carboxylate group, carboxylic acid group, cyanato group, cyano group, cycloalkenyl group, cycloalkyl group, dialkylamino carbonyl group, dialkylamino group, guanidino group, guanyl group, heteroarylalkoxy group, heteroarylalkyl group, heteroaryl group, heteroarylcarbonyl group, heteroaryloxy group, heterocyclic group, hydroxamino group, hydroxy group, imino group, isocyanato group, isocyano group, mercapto group, nitro group, oxo group, perhaloalkenyl group, perhaloalkoxy group, perhaloalkyl group, perhaloalkynyl group, perhaloarylalkyl group, perhaloaryl group, perhalocycloalkyl group, phosphate group, phosphine group, phospho group, sulfate group, sulfo group, sulfonyl group, oxidized form thereof, combination thereof; oxidized form thereof, or combination thereof. Oxidized forms of the groups are possible.

It should be understood that the terms univalent and divalent refer in most cases to the radical species resulting from removal of one or more protons or other atom from a parent group or molecule. For example, a methyl group (—$CH_3$) is the univalent form, radical or residue of methane. Similarly, a methylene group (—$CH_2$—) is the divalent form, radical or residue of methane. These terms are used for convenience in describing various structures and formulas herein, and should not be considered as limiting to a particular synthetic pathway.

In some embodiments, the compound may be included in a mixture of diastereomers. If desired, the diastereomers can be separated by taking advantage of their different physical properties, such as using either recrystallization or chromatography or a combination thereof. The recrystallizations can accomplished in organic solvents such as, but not limited to, pentane, hexane, cyclohexane, toluene, benzene, chlorobutane, dichloromethane, diethyl ether, tetrahydrofuran, dimethoxyethane, acetonitrile, methanol, ethanol or butanol or a combination of organic solvents with or without water. The chromatography can be accomplished with a silica gel or alumina solid phase, eluting with mixtures of organic solvents, with or without acidic or basic modifiers, such as triethylamine, aqueous ammonia, acetic acid or aqueous hydrochloric acid.

In some embodiments, the compounds are suitable for the treatment and/or prevention of diseases and disorders characterized by mycobacterial activity or infection. The mycobacteria may be pathogenic or non-pathogenic. The mycobacteria may be Gram positive or Gram negative.

In some embodiments, a composition is provided, which includes one or more of the compounds and optionally a physiologically acceptable carrier.

In some embodiments, a method is provided, which includes administering the compound or the composition to a subject in need thereof, to treat the subject.

In some embodiments the compounds, compositions, and methods are suitable for the treatment in humans (either or both of immunocompetent and immunocompromised) and animals of tuberculous, lepromatous, and non-tuberculous mycobacteria. Non-limiting examples of these include but are not limited to the following species and strains: Tuberculous mycobacteria, for example *M. tuberculosis, M. bovis, M. africamun, M. microti, M. canetti*; Lepromatous mycobacteria, for example *M. leprae, M. lepromcnosis*; Non-tuberculous mycobacteria, for example *M. abscessus, M. abcessus complex, M. avium, M. intracellularae, M. avium complex, M. kansasii, M. malmoense, M. xenopi, M. malmoense, M. flavences, M. scrofulaceum, M. chelonae, M. peregrinum, M. haemophilum, M. fortuitum, M. marinum, M. ulcerans, M. gordonae, M. haemophilum, M. mucogenicum, M. nonchromogenicum, M. terrae, M. terrae complex, M. asiaticum, M. celatum, M. shimoidei, M. simiae, M. smegmatis, M. szulgai, M. celatum, M. conspicuum, M. genavense, M. immunogenum, M. xenopi*.

In some embodiments the compounds, compositions, and methods are suitable for the treatment in humans (both immunocompetent and immunocompromised) and animals of non-mycobacterial infectious diseases.

In some embodiments, the subject is known or suspected to need treatment for one or more maladies related to non-pathogenic mycobacterial strain, *M. smegmatis, M. vaccae, M. aurum*, or combination thereof.

In some embodiments, the subject is known or suspected to need treatment for one or more maladies related to Gram positive bacteria, *S. aureus, M. luteus*, or combination thereof.

In some embodiments, the subject is known or suspected to need treatment for one or more maladies related to Gram negative bacteria, *P. aeruginosa, A. baumanii*, or combination thereof.

In some embodiments, the subject is known or suspected to need treatment for one or more maladies related to pathogenic mycobacterial strain, *M. tuberculosis, M. bovis, M. marinum, M. kansasaii*, H37Rv, *M. ofricanum, M. canetti, M. caprae, M. microti, M. mungi, M. pinnipedii, M. leprae, M. avium*, myobacterium tuberculosis complex, tuberculosis, or combination thereof.

In some embodiments, the subject is known or suspected to need treatment for one or more maladies related to non-pathogenic mycobacterial strain, *M. smegmatis, M. vaccae, M. aurum*, Gram positive bacteria, *S. aureus, M. luteus*, Gram negative bacteria, *P. aeruginosa, A. baumanii*, pathogenic mycobacterial strain, *M. tuberculosis, M. bovis, M. marinum, M. kansasaii*, H37Rv, *M. africanum, M. canetti, M. caprae, M. microti, M. mungi, M. pinnipedii, M. avium*, myobacterium tuberculosis complex, tuberculosis, or combination thereof.

In some embodiments, a method is provided, which includes killing or inhibiting the growth of a population of one or more of non-pathogenic mycobacterial strain, *M. smegmatis, M. vaccae, M. aurum*, Gram positive bacteria, *S. aureus, M. luteus*, Grain negative bacteria, *P. aeruginosa, A. baumanii*, pathogenic mycobacterial strain, *M. tuberculosis, M. bovis, M. marinum, M. kansasaii*, H37Rv, *M. africanum, M. canetti, M. caprae, M. microti, M. mungi, M. pinnipedii, M. avium*, myobacterium tuberculosis complex, tuberculosis, or combination thereof, by contacting one or more member of said population with the compound or composition.

In some embodiments the compounds, compositions, and methods are suitable for use or treatment alone or in combination with one or more additional treatments, for example either concurrently or with delayed administration.

In some embodiments, the compounds, compositions and methods are suitable for use in combination with one or more additional treatment with antimicrobials, for example including Isoniazid, Ethambutol, Rifampin, rifabutin, Aminoglycosides (e.g., streptomycin, amikacin, tobramycin), Macrolides (e.g., azithromycin, clarithromycin), Quinolones (e.g. ofloxacin, ciprofloxacin, moxifloxac in), Tetracyclines (e.g., doxycycline, minocycline), Sulfonaimides and combinations thereof (e.g., sulfonamides, trimethoprim/sulfamethoxazole), Beta-lactam containing antimicrobials (including peniciilins, and cephalosporins), Benzofuans (e.g. nitrofurantoin), Oxazolidinones (e.g. linezolid), Glycopeptides (e.g. vancomycin), Lipopeptides (e.g. daptomycin), Streptogramins (e.g. quinpristin/dalfopristin), Pleuromutatlins (e.g. retapamulin), Polymyxins (e.g. colistin), Lipoglycopeptides (e.g. telavancin), Glycylcyclines (e.g. tigecycline), Polyene antifungals (e.g. amphotericin B), Imidazole antifungals (e.g. ketoconazole), Allylamines antifungals (e.g. amorolfin), Triazole antifungals (e.g. voricoconizole), Thiazole antifungals (e.g. abafungin), Echinocandin antifungals (e.g., anidulafungin), Clofazimine, and the like, or other antimicrobials (e.g. anti-malarial, anti-helminth, anti-protozoal agents), Cytochrome P450 (CYP) inhibitors, 1-Aminobenzotriazole (ABT), cimetidine, amiodarone, erythromycin, fluconazole, miconazole, diltiazem, verapamil, delavirdine, amprenavir, fosamprenavir, conivaptan, ritonavir. Combinations are possible.

In some embodiments, e.g., in the case of TB, the compound may be administered to a subject in need thereof together with or in addition to one or more of Isoniazid, Rifampin, Rifadin, Rimactane, Ethambutol, Myambutol, Pyrazinamide, antibiotic, fluoroquinolone, Amikacin, Kanamycin, Capreomycin, Bedaquiline, Delamanid, PA-824, Linezolid, Sutezolid, or any combination thereof.

In some embodiments, the compounds, compositions and methods are suitable for use as single or combination agents to treat inflammatory diseases. Anti-inflammatory drugs may also be co-administered during the treatment. Inflammatory diseases are well known, and are typically pertaining to, characterized by, causing, resulting from, or becoming affected by inflammation. Non-limiting examples of inflammatory diseases or disorders include, without limitation, asthma, lung inflammation, COPD, inflammation post infection, atherosclerosis, pain, dermatitis, chronic granulomatous diseases such as tuberculosis, leprosy, sarcoidosis, and silicosis, nephritis, amyloidosis, rheumatoid arthritis, ankylosing spondylitis, chronic bronchitis, scleroderma, lupus, polymyositis, appendicitis, inflammatory bowel disease, ulcers, Sjogren's syndrome, Reiter's syndrome, psoriasis, pelvic inflammatory disease, orbital inflammatory disease, thrombotic disease, and inappropriate allergic responses to environmental stimuli such as poison ivy, pollen, insect stings and certain foods, including atopic dermatitis and contact dermatitis.

In some embodiments, the subject is mammalian, human, livestock, cow, pig, horse, or the like.

In some embodiments, the population is present on a surface, and the compound or composition is contacted with said surface.

In some embodiments, the compound can be administered to a human patient by itself or in pharmaceutical compositions where it may be mixed with suitable carriers or excipients at doses to treat or ameliorate various conditions characterized by mycobacterial activity or infection. A therapeutically effective dose may refer to that amount of the compound sufficient to inhibit the mycobacterial activity or infection, it being understood that such inhibition may occur at different concentrations such that a person skilled in the art could determine the required dosage of compound to inhibit the target mycobacterial activity or infection. Therapeutically effective doses may be administered alone or as adjunctive therapy in combination with other treatments. Some examples of techniques for the formulation and administration of the compounds may be found in Remington's Pharmaceutical Sciences, 18th Edition, A. R. Gennaro, Ed., Mack Publishing Co., Easton, Pa. (1990).

Suitable routes of administration which are not intended to be limiting may include, for example, oral, intravenous, inhaled, intra-peritoneal, rectal, transmucosal, buccal, intra-vaginal, intestinal, topical, intradermal, parenteral delivery, intramuscular, subcutaneous, intramedullary injection, intrathecal, direct intraventricular, intravenous, intraperitoneal, intranasal, intraocular, peritoneal, pleural, and optionally in a depot or sustained release formulation. Furthermore, one may administer the compound in a targeted drug delivery system, for example in a liposome.

The compounds may be administered systemically (e.g. oral, intravenous, inhaled, intra-peritoneal, rectal) or locally (e.g., topical, intradermal, intrathecal, peritoneal, pleural, intraocular, intra-vesicular, intra-vaginal, or delivered specifically to the infection site).

The pharmaceutical compositions and compounds may be manufactured in a manner that is itself known, e.g., by means of conventional mixing, dissolving, dragee-making, levitating, emulsifying, encapsulating, entrapping, or lyophilizing processes. The pharmaceutical compositions thus may be formulated in conventional manner using one or more physiologically acceptable carriers comprising excipients and auxiliaries that facilitate processing of the active compounds into preparations, which can be used pharmaceutically. Proper formulation may be dependent upon the route of administration chosen.

Any combination of one or more the present compounds, salts thereof, resonance forms thereof, prodrugs, metabolites, isotopically-labeled compounds, tautomers, isomers, and/or atropisomers is possible in the composition.

For injection, the compounds may be formulated in aqueous solutions, preferably in physiologically compatible buffers, such as Hank's solution, Ringer's solution, or physiological saline buffer. For transmucosal administration, penetrants appropriate to the barrier to be permeated are used in the formulation. Such penetrants are known in the art.

For oral administration, the compounds can be formulated readily by combining the active compounds with pharmaceutically acceptable carriers well known to those in the art. Such carriers enable the compounds to be formulated as tablets, pills, dragees, capsules, liquids, gels, syrups, slurries, suspensions and the like, for oral ingestion by a patient to be treated. Pharmaceutical preparations for oral use can be obtained by combining the compound with a solid excipient, optionally grinding the resulting mixture, and processing the mixture of granules, after adding suitable auxiliaries, if desired, to obtain tablets or dragee cores. Suitable excipients include but are not limited to fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as polyionic block (co)polymer, sodium carboxymethyl cellulose, sorbitol, or dextran. Optionally, the suspension may also contain suitable stabilizers or agents which increase the solubility of the compounds.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

The compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid- or gel-phase carriers or excipients. Examples of such carriers or excipients include but are not limited to calcium carbonate, calcium phosphate, various sugars, starches, cellulose derivatives, gelatin, and polymers such as polyethylene glycols.

In some embodiments, the compounds may be provided as salts with pharmaceutically compatible counterions. Pharmaceutically compatible salts may be formed with many acids, including but not limited to hydrochloric, sulfuric, acetic, lactic, tartaric, malic, succinic, etc.; or bases. Non-limiting examples of pharmaceutically acceptable salts include sodium, potassium, lithium, calcium, magnesium, iron, zinc, hydrochloride, hydrobromide, hydroiodide, acetate, citrate, tartrate and maleate salts, and the like.

Generally, pharmaceutical compositions contain the active compound in an effective amount to achieve their intended purpose. In one embodiment, a therapeutically effective amount means an amount effective to prevent or inhibit development or progression of a disease characterized by mycobacterial infection or activity in the subject being treated. Determination of the effective amounts is within the capability of those skilled in the art in light of the description provided herein.

Any group described herein, whether it is expressly denoted as a "group" or is not denoted as such (e.g., using terms such as "alkyl," "aryl," "aroyl," and the like, alone) may be optionally and independently straight or branched; may be optionally and independently substituted by one or more independent substituent groups; may be optionally and independently attached directly to the relevant parent structure; may be optionally and independently attached indirectly to the relevant parent structure via one or more divalent intervening substituent groups; and/or may have one or more than one atom optionally and independently replaced with one or more independent heteroatoms.

The use of the word "a" or "an" when used in conjunction with the term "comprising" in the claims and/or the specification may mean "one," but it is also consistent with the meaning of "one or more," "at least one," and "one or more than one."

The term, "about" is used to indicate that a value includes the standard deviation of error.

The term, "or" means "and/or" unless explicitly indicated to refer to alternatives only or the alternatives are mutually exclusive, although the disclosure supports a definition that refers to only alternatives and "and/or."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other embodiments of the invention are discussed throughout this application. Any embodiment discussed with respect to one aspect applies to other embodiments as well and vice versa. Each embodiment described herein and any obvious variation thereof is understood to be applicable to all embodiments of the invention. Given the description herein, combined with the knowledge of one of ordinary skill in the art to which the invention pertains, any embodiment described herein can be easily accomplished and/or further implemented with respect to any use, method, compound, composition, kit, obvious variant thereof, or any combination thereof.

Examples

The Examples herein are provided for illustration, and are not intended to limiting unless otherwise specified.

The present compounds have great potency, pharmacokinetics, and reduced toxicity. For example ND-10823 was found to have dose limiting toxicity in mice at 100 mg/kg limiting its potential usefulness as mice would die at doses higher than 100 mg/kg. However, the addition of the 3-fluorine increased potency and substantially decreased in vivo toxicity to 250 mg/kg with ND-10890.

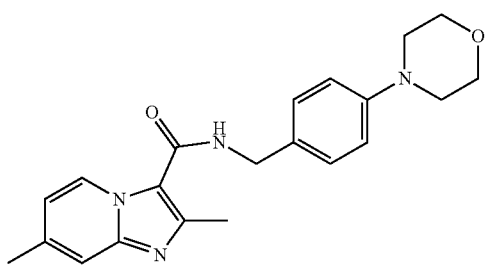

ND-10823
MIC Mtb = 0.3 - 1.3 µM
MTD = 100 mg/kg (mice)

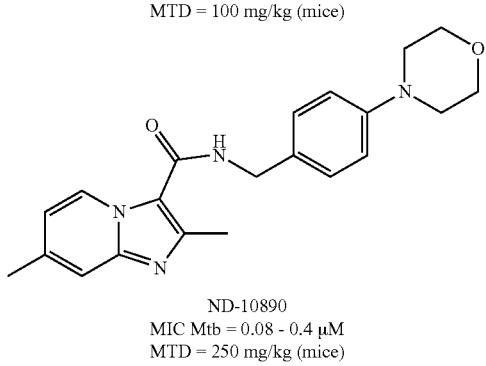

ND-10890
MIC Mtb = 0.08 - 0.4 µM
MTD = 250 mg/kg (mice)

Other compounds profiled bearing the 3-Fluorine moiety displayed great in vitro potency (nanomolar range) and high in vivo safety (for instance, ND-11543, ND-11544, ND-11598, ND-11622 all had MTD≥250 mg/kg).

Shown in FIG. 1 is the in vivo tolerability of two representative compounds ND-11598 and ND-11622 at 100 mg/kg dosed orally for two weeks and 250 mg/kg dosed orally for one week. The mice showed no signs of distress, no weight loss and all survived the treatment course. This suggests that the maximum tolerated dose is >250 mg/kg for these compounds.

Figure 2:
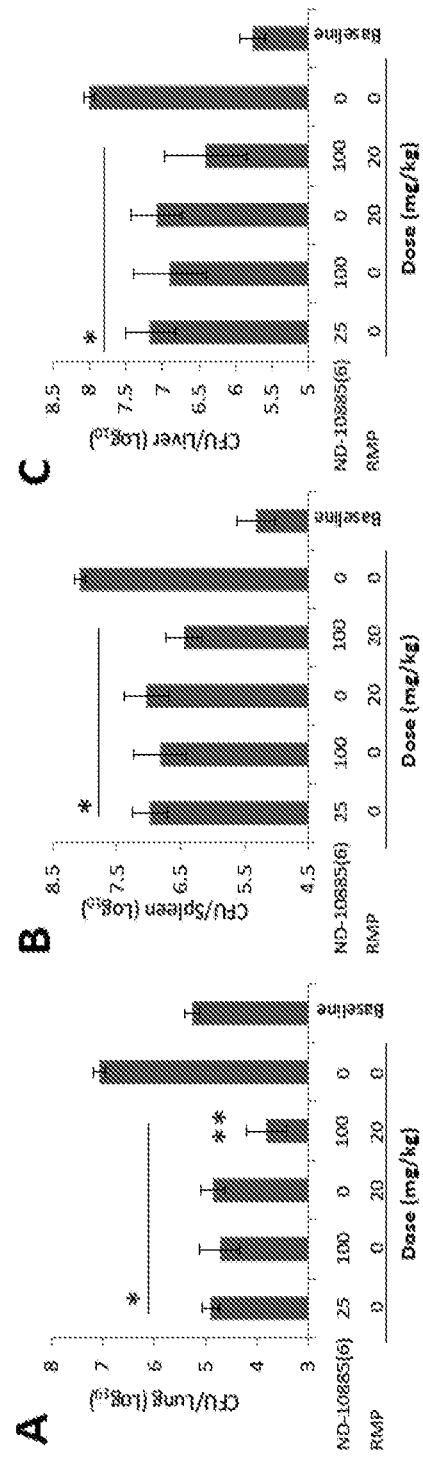
FIG. 2 graphically presents in vivo efficacy of ND-10885 in mice infected with *Mycobacterium avium* 101 when dosed orally with 25 mg/kg and 100 mg/kg. Panel A is the log 10 colony forming units (CFU) drop in bacteria in the lungs when treated with ND-10885 (at 25 and 100 mg/kg), rifampicin (RMP, 20 mg/kg) and a combination of ND-10885 (100 mg/kg) and rifampicin (20 mg/kg). Panel B is the log 10 colony forming units (CFU) drop in bacteria in the spleen when treated with ND-10885 (at 25 and 100 mg/kg), rifampicin (RMP, 20 mg/kg) and a combination of ND-10885 (100 mg/kg) and rifampicin (20 mg/kg). Panel C is the log 10 colony forming units (CFU) drop in bacteria in the liver when treated with ND-10885 (at 25 and 100 mg/kg), rifampicin (RMP, 20 mg/kg) and a combination of ND-10885 (100 mg/kg) and rifampicin (20 mg/kg). There is statistically supported improvement in efficacy in the drug combination within the lung and spleen.

Results shown in FIG. 2 validate the in vivo efficacy of ND-10885 in mice infected with *Mycobacterium avium* 101 when dosed orally with 25 mg/kg and 100 mg/kg. Panel A is the log 10 colony forming units (CFU) drop in bacteria in the lungs when treated with ND-10885 (at 25 and 100 mg/kg), rifampicin (RMP, 20 mg/kg) and a combination of ND-10885 (100 mg/kg) and rifampicin (20 mg/kg). Panel B is the log 10 colony forming units (CFU) drop in bacteria in the spleen when treated with ND-10885 (at 25 and 100 mg/kg), rifampicin (RMP, 20 mg/kg) and a combination of ND-10885 (100 mg/kg) and rifampicin (20 mg/kg). Panel C is the log 10 colony forming units (CFU) drop in bacteria in the liver when treated with ND-10885 (at 25 and 100 mg/kg), rifampicin (RMP, 20 mg/kg) and a combination of ND-10885 (100 mg/kg) and rifampicin (20 mg/kg). There is statically supported improvement in efficacy in the drug combination within the lung and spleen.

Results shown in FIG. 3 demonstrate the in vitro potency of compounds against various serotypes of *Mycobacterium avium* plus a gentamicin resistant *M. avium* strain. Rifampin is included as a positive control and DMSO as a negative control. MIC values are reported in µg/mL and read by Resazurin dye.

Results shown in FIG. 4 demonstrate the in vitro potency of compounds against *Mycobacterium intracellulare* (ATCC 13950). Rifampin, Clarithromycin, Ethanbutol, and Azithromycin are included as a positive controls and DMSO as a negative control. MIC values are reported in µg/mL and read by Resazurin dye.

Results shown in FIG. 5 demonstrate the in vitro potency of compounds against clinical isolates of *Mycobacterium avium* and Clarithromycin was used as a positive control. MIC values are reported in µg/mL and read by 3-(4,5-dimethylthiazol-2-yl)-2,5-diphenyltetrazolium bromide (MTT) dye.

Results shown in FIG. 6 demonstrate the in vitro potency of compounds against clinical isolates of *Mycobacterium kansasii*; Clarithromycin was used as a positive control. MIC values are reported in µg/mL and read by 3-(4,5-dimethylthiazol-2-yl)-2,5-diphenyltetrazolium bromide (MTT) dye.

Figure 7:
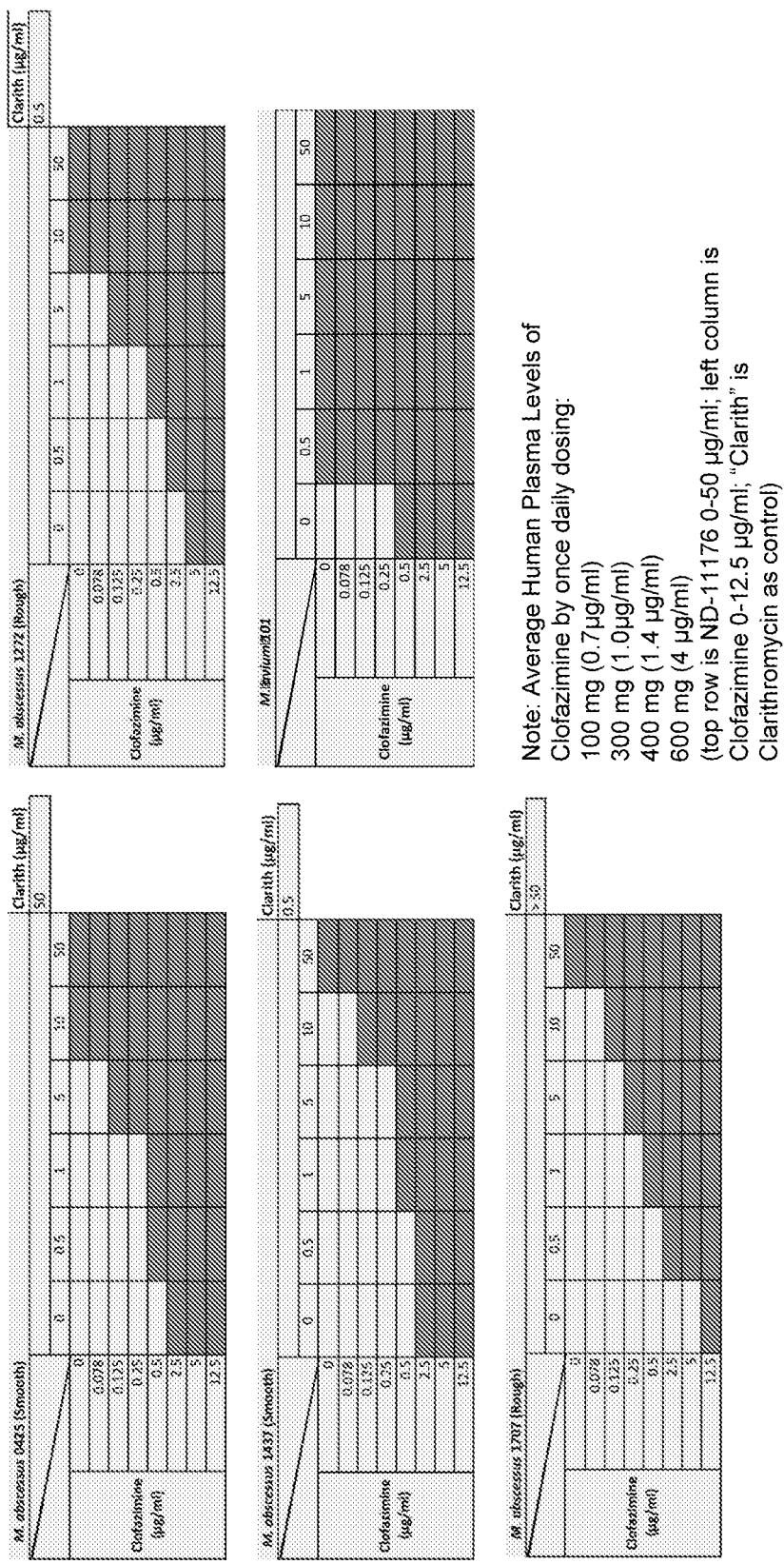
FIG. 7 graphically presents MICs of ND-11176 and Clofazimine, both alone and in combination, against *Mycobacterium abscessus* in a "checker board" assessment. Clarithromycin was used as a positive control. MIC values are reported in μg/mL read by Resazurin dye. In the figure, dark boxes represent dead, lighter boxes represent alive.

Results shown in FIG. 7 demonstrate synergistic effects of ND-11176 and Clofazimine against *Mycobacterium abscesses* in a "checker board" assessment. Clarithromycin was used as a positive control. MIC values are reported in µg/mL read by Resazurin dye. In the figure, dark boxes represent dead, lighter boxes represent alive.

FIG. 8 is a table of compounds and screening results of compounds against *Mycobacterium tuberculosis* (Mtb) H37Rv in various media (GAS, 71-112), in low oxygen conditions (LORA), the toxicity to Vero cells, as well as the potency against *Mycobacterium avium* (101 and 2151) and *Mycobacterium intracellulare*. Resazurin dye is used to read MICs against *M. avium* and *M. intracellulare* while MABA was used to read out MICs against Mtb.

Assays:

In vitro activity VS. Mtb-H37Rv were evaluated in both GAS (glycerol-alanine salt) and 7H12 media with metabolic activity measured using a Microplate Alamar Blue Assay (MABA) by the protocols described by Cho, S.; Lee, H. S.; Franzblau, S. G. in the article "Microplate Alamar Blue Assay (MABA) and Low Oxygen Recovery Assay (LORA) for *Mycobacterium tuberculosis*." Mycobacteria Protocols 2015, 281-292. Activity against non-replicating (latent) Mtb was evaluated with a luminescence readout using the low oxygen recovery assay (LORA).

Description of TB (GAS, 7H12) by Microplate Alamar Blue Assay (MABA) to Determine $MIC_{90}$ Values Against Replicating TB:

The test compound MICs against Mtb $H_{37}Rv$ (ATCC #27294) were assessed by the MABA (Cho, S.; Lee, H. S.; Franzblau, S. G. "Microplate Alamar Blue Assay (MABA) and Low Oxygen Recovery Assay (LORA) for *Mycobacterium tuberculosis*." Mycobacteria Protocols 2015, 281-292) using rifampin and PA-824 as positive controls. Compound stock solutions were prepared in DMSO at a concentration of 128 µM, and the final test concentrations ranged from 128 µM to 0.5 µM. Two fold dilutions of compounds were prepared in glycerol-alanine-salt media in a volume of 100 µL in 96-well microplates (BD Optilux™, 96-well Microplates, black/clear flat bottom) for the GAS assay (Collins, L., and Franzblau, S. G. (1997) Microplate alamar blue assay versus BACTEC 460 system for high-throughput screening of compounds against *Mycobacterium tuberculosis* and *Mycobacterium avium*. Antimicrob. Agents Chemother. 41, 1004-1009), in an iron deficient glycerol-alanine-salt media with 20% Tween 80 added in the GAST assay and in Middlebrook 7H12 medium (7H9 broth containing 0.1% w/v casitone, 5.6 µg/mL palmitic acid, 5 mg/mL bovine serum albumin, 4 mg/mL catalase; De Voss, J. J., Rutter, K., Schroeder, B. G., Su, H., Zhu, Y., and Barry, C. E. (2000) The salicylate-derived mycobactin siderophores of *Mycobacterium tuberculosis* are essential for growth in macrophages. Proc. Nat. Acad. Sci. U.S.A. 97, 1252-1257). In a volume of 100 µL in 96-well microplates (BD Optilux™, 96-well Microplates, black/clear flat bottom) for the TB assay. The TB cultures (100 µL inoculums of 2×105 cfu/mL) were added to the media, yielding a final testing volume of 200 µL. The plates were incubated at 37° C. On the seventh day of incubation, 12.5 µL of 20% Tween 80, and 20 µL of Alamar Blue (Invitrogen BioSource™) were added to the wells of test plate. After incubation at 37° C. for 16-24 h, fluorescence of the wells was measured at 530 nm (excitation) and 590 nm (emisSion). The MICs are defined as the lowest concentration effecting a reduction in fluorescence of ≥90% relative to the mean of replicate bacteria-only controls.

Description of MDR- and XDR-Mtb Assay:

MICs were set up as described in Wong et al. (Wong, S. Y., Lee J. S., Kwak, H. K., Via, L. E., Boshoff, H. I., and Barry, C. E. 3rd. (2011) *Antimicrob Agents Chemother.* 55, 2515-22.)

Briefly, the *M. tuberculosis* strains were grown in Middlebrook 71-19 broth (Becton Dickinson, NJ) supplemented with 10% albumin-dextrose-catalase, 0.05% Tween 80, and 0.2% glycerol to an optical density at 650 nm of 0.25. Cells were diluted 1000-fold in the above medium. Compounds were added to the first column of a round-bottom, 96-well plate in triplicate and 2-fold serial dilutions created across the remaining columns with supplemented Middlebrook 7H9 medium as the diluent. An equal volume of the diluted cell suspension was added to well with a final volume of 100 µl per well. Plates were incubated at 37° C. for 14 days, after which cell growth was visually inspected. The MIC value was defined as the lowest drug concentration that completely inhibited all visual growth.

Description of VERO (Faizari, K, Zhou. 7, Pan, D., Liu, H, Hongmanee, P., and Franzblau, S. G. (2005) In Vitro and In Vivo Activities of Macrolide Derivatives Aagainst *Mycobacterium tuberculosis*. Antimicrob Agents Chemother. 49, 1447-1454) Cytotoxicity Assay to Determine $IC_{50}$ Values:

Samples were dissolved at 12.8 mM in DMSO. Geometric three-fold dilutions were performed in growth medium MEM (Gibco, Grand Island, N.Y.), containing 10% S5 fetal bovine serum (FlyClone, Logan, Utah), 25 mM N-(2-hydroxyethyl)-piperazine-N'-2-ethanesulfonic acid (HEPES, Gibco), 0.2% $NaHCO_3$ (Gibco), and 2 mM glutamine (Irvine Scientific, Santa Ana, Calif.). Final DMSO concentrations did not exceed 1% v/v. Drug dilutions were distributed in duplicate in 96-well tissue culture plates (Becton Dickinson Labware, Lincoln Park, N.J.) at a volume of 50 µL per well. An equal volume containing $5 \times 10^5$ log phase VERO cells (Green African Monkey kidney cells, CCL-81; American Type Culture Collection, Rockville, Md.) was added to each well and the cultures were incubated at 37° C. in an atmosphere containing 5% of $CO_2$. After 72 h, cell viability was measured using the CellTiter 96 aqueous non-radioactive cell proliferation assay (Promega Corp., Madison, Wis.) according to the manufacturer's instructions. Then absorbance at 490 nm was read in a Victor multilabel reader (PerkinElmer). The $IC_{50}$ values (inhibition concentration at 50%) were determined using a curve-fitting program.

In vitro activity vs. MAC—Eleven *M. avium* strains were exposed to compounds for 3 days and metabolic activity and bacteriostatic/bactericidal activity was measured by resazurin. This was done by the methods described in J. Antimicrob. Chemother. (2007) 60 (1): 152-155.

Efficacy against MAC infections compounds like ND-10890 has shown efficacy in the murine infection model see, ANTIMICROBIAL AGENTS AND CHEMO-THERAPY, 1995, 39(8), 1647-1654 for review of MAC infection model and Antimicrob Agents Chemother. 1992, 36(11):2413-7 for a typical experiment (done with clarithromycin). In a two week infection experiment in Balb/c mice with 25 mg and 100 mg doses of ND-10890 there was >2 log 10 CFU drop in the amount of *M. avium* in the lungs of treated mice. This was better bacterial clearing than control rifampicin (1.8 log 10 CFU). ND-10890 (100 mg) and rifampicin (20 mg) combination therapy was even more effective with near sterilization of *M. avium* bacteria (~3 log 10 CFU drop). These data suggest that these compounds will be effective treatments for mycobacterial infections.

A set of lead compounds were screened against a panel of diverse organisms which included five Gram positive strains (*Bacillus subtilis, Staphylococcus aureus*, MRSA *Staphylococcus aureus*, VRE *Enterococcus Faecalis, Mycobacterium vaccae*) two Gram negative strains (*E. coli, Pseudomonas aeruginosa*), a yeast (*Sporobolomyces salmonicolor*) and fungi (*Candida albicans* and *Penicillium notatum*). Remarkably, this class was weak against all of the control organisms studied except for good activity against *M. vaccae* as well as other mycobacteria. Against a panel of Nontuberculous Mycobacteria (NTM) strains this class was found to be potent inhibitors of *M. avium, M. Bovis* BCG, *M. kansasii* (<0.08 mM) and mostly weak to *M. abscesses, M. chelonae, M. marinum* and *M. smegmatis* (>10 mM). These compounds have nanomolar potency against mono-drug resistant, multi-drug resistant (MDR−) and extensively drug resistant (XDR−) Mtb. Mechanism of action (MOA) studies via generation of Mtb mutants revealed a high frequency of spontaneous mutants ($>10^{-8}$) and that these compounds target the respiratory bc1 complex (Complex III). Lead compounds were screened against six mammalian cell lines (PC-3, MCF-7, Huvec, K-562, HeLa and VERO) showing no toxicity $IC_{50}$>50 µM.

Synthesis:

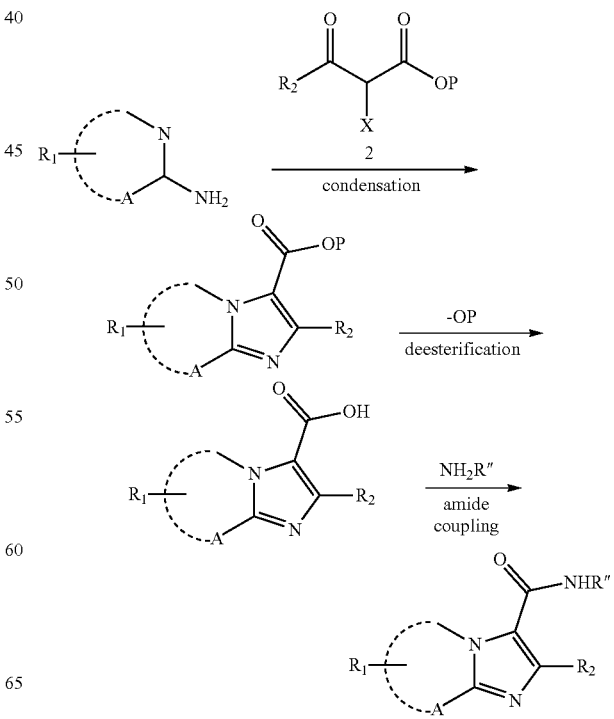

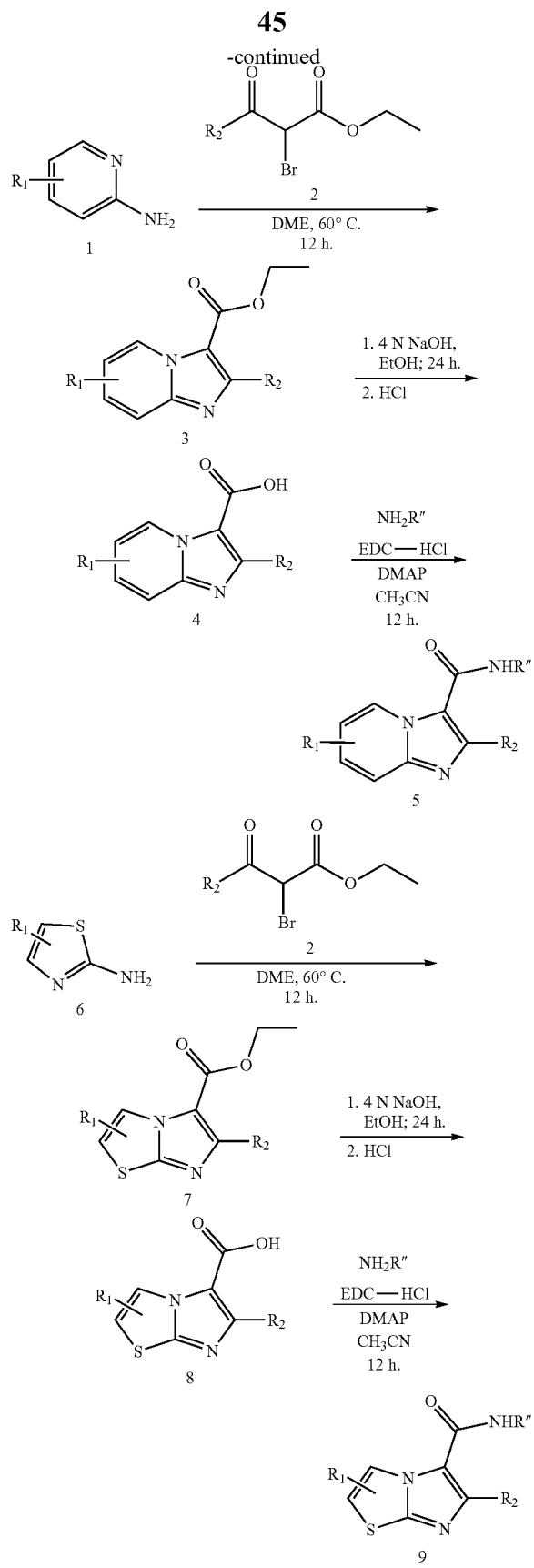

a 2-amino-pyridine 1 or a 2-amino-thiazole 6 with an α-halo-ketone 2 (ie. 2-bromo acetoacetate or 2-chloro acetoacetate) in a suitable solvent like dimethoxyethane or ethanol. Deesterification with base (LiOH, NaOH, KOH, etc) in a suitable alcohol solvent (MeOH, EtOH) followed by acidification with HCl gives the heterocyclic carboxylic acid core (4 and 8). The heterocylic carboxylic acids (4 or 8) are then coupled to various amines ($NH_2R''$) by any method of amide formation reactions as described by Bodansky, M. in "Principles of Peptide Synthesis" from Springer-Verlag, 1988, to give desired amides 5 and 9.

Various reagents of structure 2 are commercially available for instance ethyl 2-chloroacetoacetate [CAS: 609-15-4, Sigma-Aldrich] and Ethyl 2-bromo-3-oxobutanoate [CAS: 609-13-2, Ark Pharm] while others can be prepared by either the method in Synthetic Communications, 37(23), 4149-4156; 2007 using N-chlorosuccinimide (NCS) or N-bromo-succinimide (NBS) in DMSO;

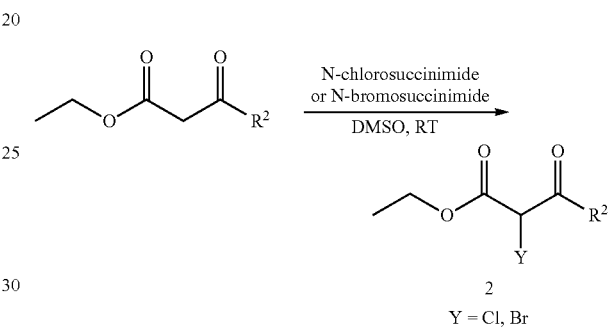

or by the methods described in the Journal of Medicinal Chemistry, 57(12), 5293-5305; 2014 (using NBS or NCS with ammonium acetate in diethyl ether).

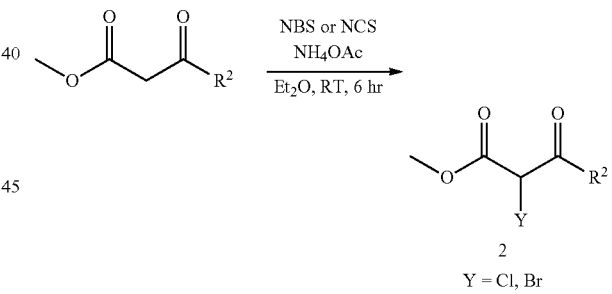

Specifically, the ethyl 2-bromo-3-oxobutanote can be prepared by the following method:

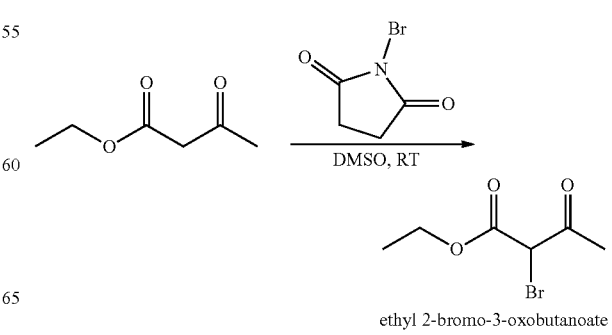

ethyl 2-bromo-3-oxobutanoate

The general synthesis involves first the formation of the heterocyclic scaffold as a methyl or ethyl ester by heating of Ethyl acetoacetate (5.2 mL, 37.7 mmol) was added to N-bromosuccinimide (9.2 g, 49 mmol) followed by 40 mL of dry DMSO. The reaction was stirred for 2 hours at RT or when complete by TLC (50% Hexane:CH$_2$Cl$_2$). Reaction mixture diluted with hexanes and organic layer was washed with saturated NH$_4$Cl solution (2×), water, then organic layer was dried over sodium sulfate. Drying agent was removed by filtration and upon concentration in vacuo crude material was purified by silica gel column with 50% Hexanes:CH$_2$Cl$_2$ to give ethyl 2-bromo-3-oxoburanoate as a light yellow oil. IR (neat): 1718, 1462, 1227 cm-1; 1H NMR (400 MHz, CDCl3): δ ppm 4.67 (1H, s), 4.28 (2H, q, J=7.0 Hz), 2.43 (3H, s), 1.32 (3H, t, J=7.0 Hz); 13C NMR (50 MHz, CDCl3): δ 197.6, 167.3, 6.8, 54.6, 27.1, 14.2.

mmol) and ammonium acetate (53 mg, 0.7 mmol) were combined together and stirred as a thick slurry for 3 hours. Next, 25 mL of diethyl ether was added and reaction was allowed to warm to room temperature where it stirred for 3 hours as reaction grew white. At which time, reaction was taken up in 100 mL of diethyl ether and washed (3×) with water, brine and dried over sodium sulfate. The drying agent was filtered off and organics were concentrated to give methyl 2-bromo-3-oxopentanoate as a clear oil, 13.45 grams. $^1$H NMR (200 MHz, CDCl3): δ ppm 1.12 (t, J=7.2 Hz, 3H, CH$_3$CH$_2$), 2.79 (q, J=7.2 Hz, 2H, CH$_3$CH$_2$), 3.82 (s, 3H, OCH$_3$), 4.81 (s, 1H, CHBr).

General synthesis of the imidazo[1,2-a]pyridine-3-carboxylic acid cores (4a, 4b, 4c, 4d) for coupling with various amines (NH$_2$R") to give the general

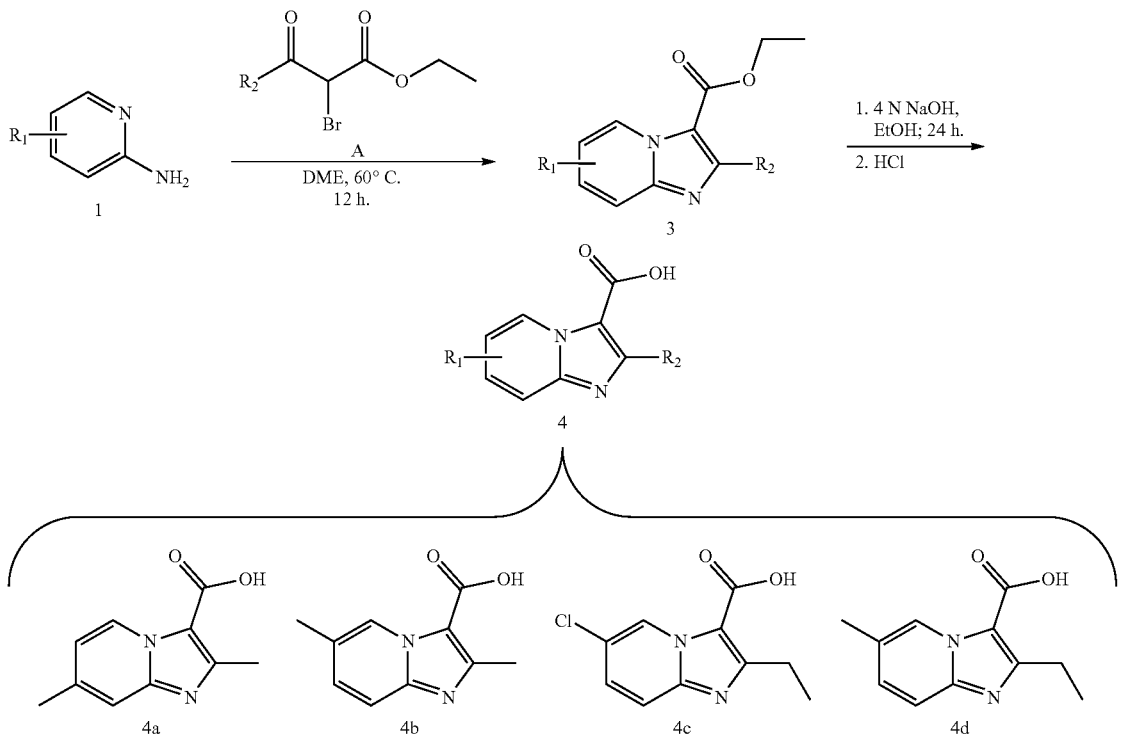

Specifically, the methyl 2-bromo-3-oxopentanoate can be prepared by the following method:

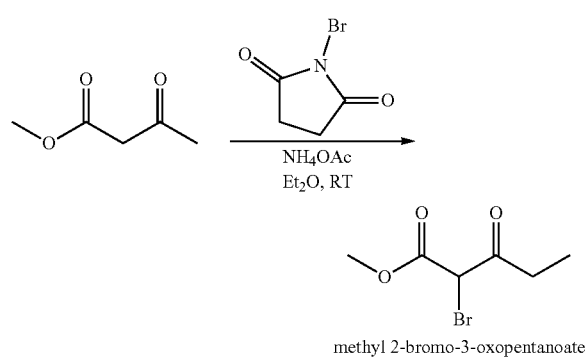

methyl 2-bromo-3-oxopentanoate

In a round bottom flask cooled in an ice bath, the methyl propionylacatate (8.7 mL, 69.2 mmol), NBS (13.5 g, 76.1

Specifically, imidazo[1,2-a]pyridine-3-carboxylic acid cores 4a and 4b can be prepared by the methods found in ACS Med. Chem. Lett., 2013, 4 (7), pp 675-679 and ACS Med. Chem. Lett., 2011, 2 (6), pp 466-470.

As specific example the 2,7-dimethylimidazo[1,2-a]pyridine-3-carboxylic acid can be prepared the following way. 2-Amino-4-picoline (10.0 g, 91.5 mmol) and ethyl-2-chloroacetoacetate (7.93 g, 45.8 mmol) were dissolved in 92 mL of 1,2-dimethoxyethane (DME) and heated for 36 h at reflux. The reaction mixture was filtered and (2-amino-4-picoline hydrochloride salt) solids were collected and washed with hexanes. The filtrate was concentrated in vacuo and the residue was dissolved in CH$_2$Cl$_2$ and washed with 5% acetic acid solution (2×) and brine. The organic phase was collected, dried over sodium sulfate (Na$_2$SO$_4$), filtered and then concentrated in vacuo. Crude material obtained was purified by silica gel column chromatography with a 20% ethyl acetate:CH$_2$Cl$_2$ solvent system to give 7.8 g (78%) of ethyl 2,7-dimethylimidazo[1,2-a]pyridine-3-carboxylate as a tan solid. Mp 59-61° C.; $^1$H NMR (300 MHz, CDCl$_3$) δ 9.14 (d, J=7.1 Hz, 1H), 7.34 (s, 1H), 6.78 (dd, J=7.1, 1.7 Hz, 1H), 4.40 (q, J=7.1, 7.1, 7.1 Hz, 2H), 2.66 (s, 3H), 2.42 (s, 3H), 1.42 (t, J=7.1, 7.1 Hz, 3H). HRMS (EI), M+1 calcd. for $C_{12}H_{15}N_2O_2$, 219.1155; found 219.1128.

Ethyl 2,7-dimethylimidazo[1,2-a]pyridine-3-carboxylate (6.64 g, 30.4 g) was dissolved in of 75 mL ethanol (95:5) and 61 mL of 1 N LiOH solution was added (61 mmol). The reaction was stirred at reflux for 36 h. Once complete, the reaction was concentrated in vacuo to near dryness and the pH was adjusted to 3 with slow addition of 4 N HCl while cooling in an ice bath. The resulting solids were collected by filtration and were dried under vacuum overnight to give 3.86 g (67%) of 2,7-dimethylimidazo[1,2-a]pyridine-3-carboxylic acid as an off white solid. Mp 180-183° C.; $^1$H NMR (300 MHz, $CD_3OD$) δ 9.52 (d, J=7.1 Hz, 1H), 7.73 (td, J=1.8, 0.9, 0.9 Hz, 1H), 7.48 (dd, J=7.1, 1.3 Hz, 1H), 2.81 (s, 3H), 2.63 (s, 3H). HRMS (EI), M+1 calcd. for $C_{10}H_{11}N_2O_2$, 191.0815; found 191.0837.

2-Ethyl-6-chloro imidazo[1,2-a]pyridine-3-carboxylic acid core 4c can be prepared by the method described in the Journal of Medicinal Chemistry, 57(12), 5293-5305; 2014. The 2-Ethyl-6-methyl-imidazo[1,2-a]pyridine-3-carboxylic acid core 4d (CAS: 1216036-36-0) can be prepared by a modification of the above procedure involving heating of 2-amino-4-picoline (CAS: 695-34-1) and methyl 2-bromo-3-oxopentanoate (CAS: 117481-97-7) in a suitable solvent (DME, EtOH) followed by saponification of resulting methyl ester to give the desire carboxylic acid.

reaction bubbled for 5 mins. The reaction concentrated to near dryness with air. Residue was dissolved in EtOAc and washed with water (2×) followed by 1 N HCl (3×), brine and then dried over sodium sulfate. Removed drying agent and concentrated in vaccuo. Residue was dissolved in $CH_2Cl_2$ and purified by a silica gel column eluding with $CH_2Cl_2$ to remove upper running spot followed by 20% EtOAc: $CH_2Cl_2$ to collected product as a yellow-orange solid upon concentration. 4.78 g (25%) of Ethyl 2,6-dimethylimidazo [2,1-b]thiazole-5-carboxylate. 1H NMR (300 MHz, $CDCl_3$) δ ppm 7.78 (s, 1H), 4.38 (dd, J=14.0, 7.0 Hz, 2H), 2.59 (s, 3H), 2.44 (s, 3H), 1.40 (t, J=7.0, 7.0 Hz, 3H).

The Ethyl 2,6-dimethylimidazo[2,1-b]thiazole-5-carboxylate (4.78 g, 21.3 mmol) was dissolved in 90 mL EtOH and then the 4 N NaOH aq. sol (10.6 mL, 42.6 mmol) was added and reaction stirred overnight at 50° C. and until TLC shows conversion to more polar spot. Reaction was concentrated to ¼ volume by blowing with air over the reaction. Residue was cooled in an ice bath and then pH was adjusted to 2-3 with the careful addition of conc. HCl (~2 mL) followed by 4 N HCl solution. Product precipitated from solution and was collected by filtration and dried under vacuum overnight. Collected 1.9 grams of 2,6-dimethylimidazo[2,1-b]thiazole-5-carboxylic acid (4a) as a light yellow solid. 1H NMR (300 MHz, $CH_3OD$) δ ppm 7.67 (s, 1H), 2.51 (s, 1H), 2.44 (s, 1H).

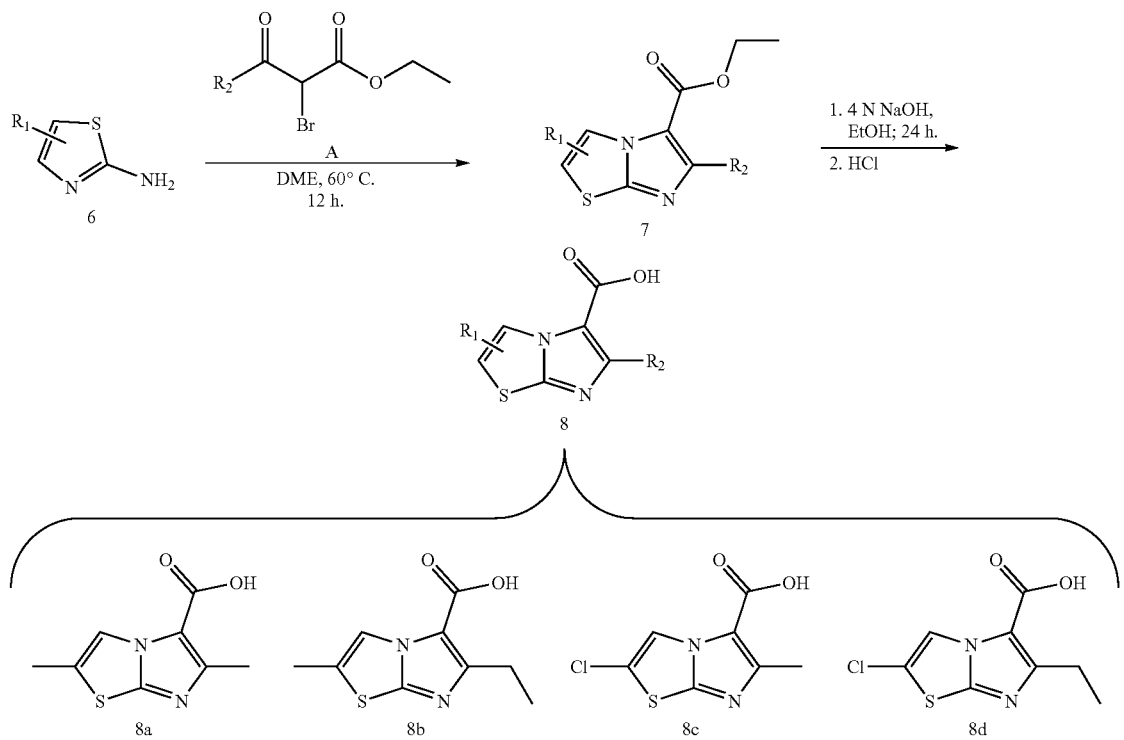

Using the same methods described above for synthesis of the imidazo[1,2-a]pyridine-3-carboxylic acids (4a-4d) the imidazo[2,1-b]thiazole-5-carboxylic acids (8a-8d) can be prepared.

For example, 2,6-dimethylimidazo[2,1-b]thiazole-5-carboxylic acid (4a) can be prepared by combining the 5-methyl-2-aminothiazole (10 g, 86.7 mmol) and ethyl 2-chloroacetoacetate (13.3 mL, 86.7 mmol) and heating the reaction to 60° C. in a minimal amount of 1,2-dichloroethane (15 mL) added for aid stirring under argon overnight. At which time, the sodium bicarbonate added (1 eq) and In some embodiments, B in the general structures,

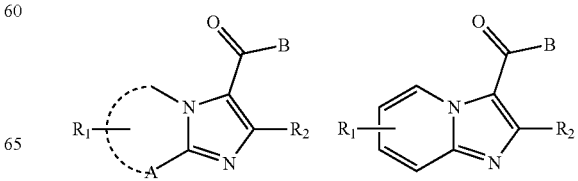

-continued
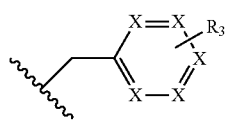
may be derived from one of the following amines, below.
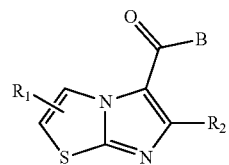
55746-20-8 and
Bioogranic Med Chem 23
(2015) 4792-4803
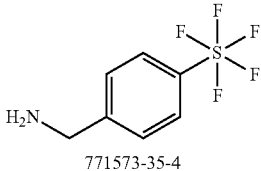
CAS: 55745-74-9
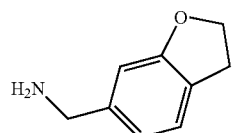
17450-69-0
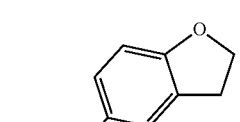
933726-50-2
864263-28-5
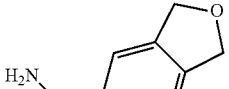
55746-19-5
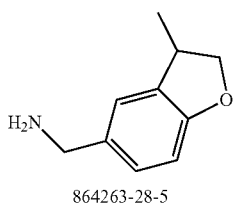
1431851-43-2
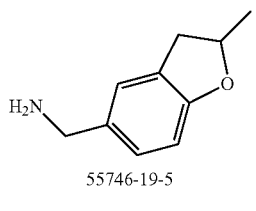
864263-33-2
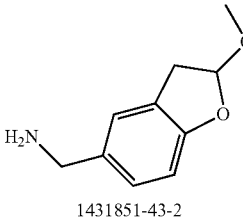
132570-56-0
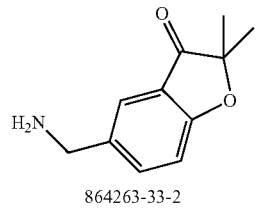
864263-30-9
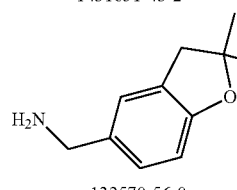
1630261-74-3
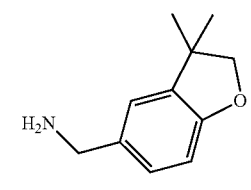
933726-57-9
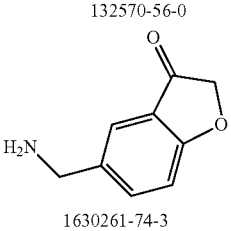
2620-50-0
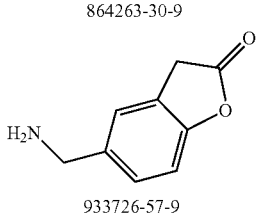
135132-35-3
-continued
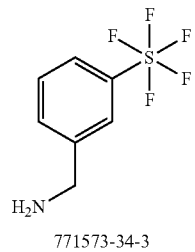
771573-35-4
771573-34-3
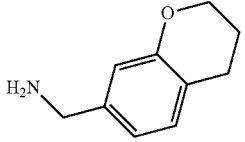
1501255-85-1
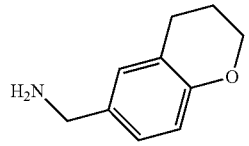
55746-21-9
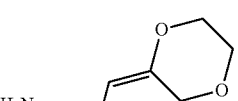
17413-10-4
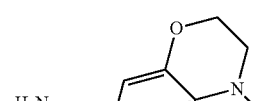
946409-08-1
In some embodiments, the R3 group, e.g., the "C-group" in the pendant group below,
may be derived from one of the following cyclic amines and substituted cyclic amines shown below:
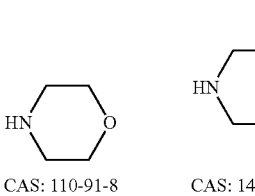
CAS: 110-91-8
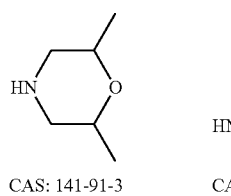
CAS: 141-91-3
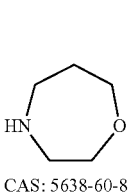
CAS: 5638-60-8
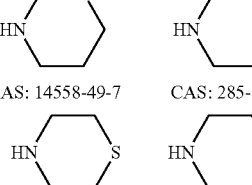
CAS: 14558-49-7
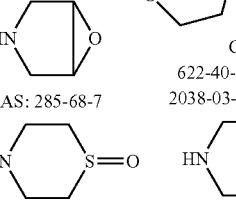
CAS: 285-68-7
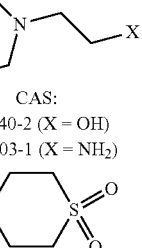
CAS:
622-40-2 (X = OH)
2038-03-1 (X = NH$_2$)
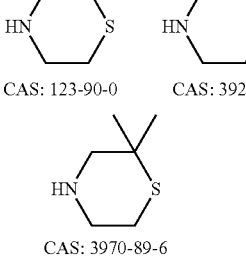
CAS: 123-90-0
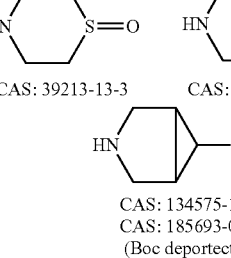
CAS: 39213-13-3
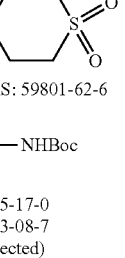
CAS: 59801-62-6
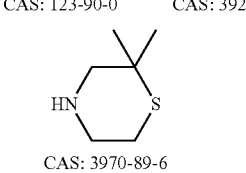
CAS: 3970-89-6
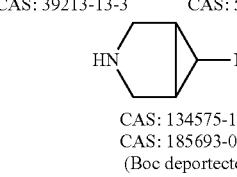
CAS: 134575-17-0
CAS: 185693-08-7
(Boc deprotected)

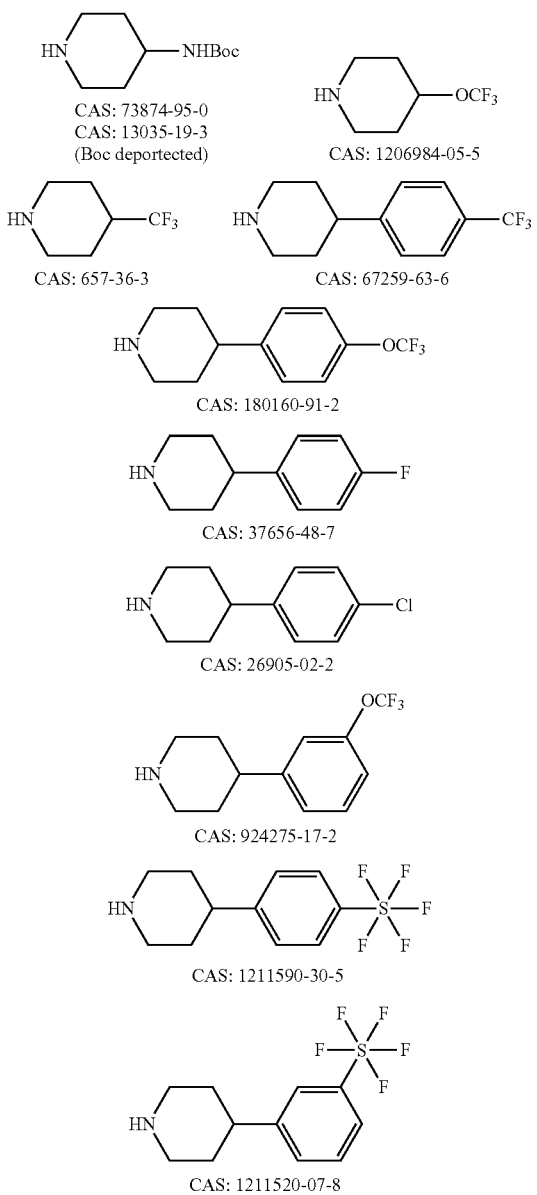
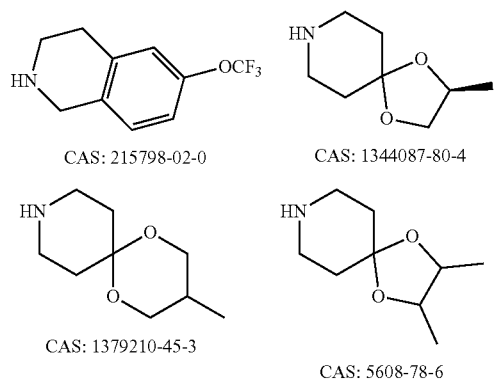
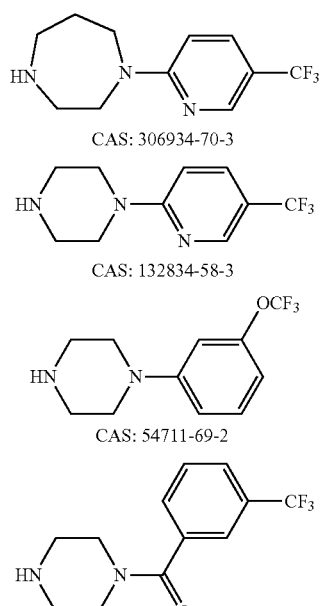
Spiro-piperidine derivatives can be prepared, for example, by ACS Medicinal Chemistry Letters, 5(5), 587-591; 2014; Bioorganic & Medicinal Chemistry Letters, 24(10), 2288-2294; 2014; Beilstein Journal of Organic Chemistry, 8, 1700-1704, No. 193; 2012.
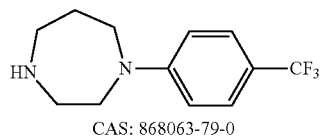
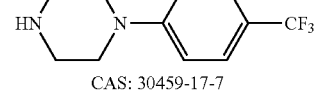
Piperidine-aryl derivatives can be prepared, for example, by U.S. Pat. Appl. Publ., 20070032469, 8 Feb. 2007; PCT Int. Appl., 2004058727, 15 Jul. 2004 and PCT Int. Appl., 2011028947, 10 Mar. 2011.
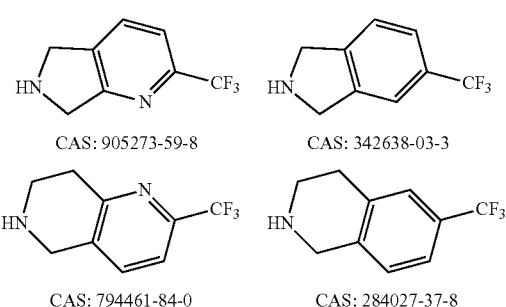
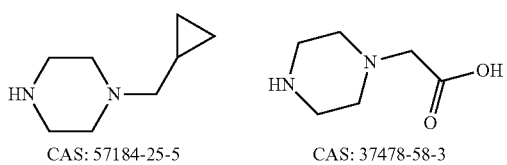

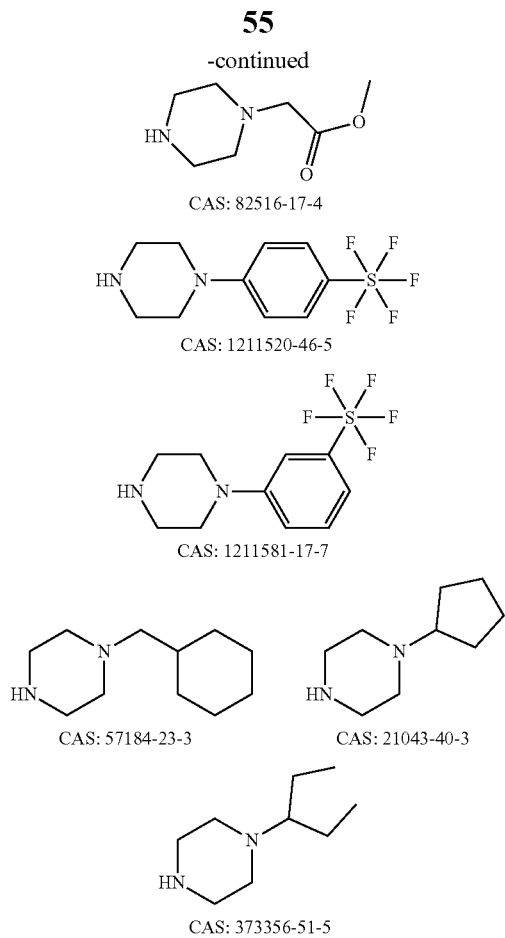

CAS: 82516-17-4

CAS: 1211520-46-5

CAS: 1211581-17-7

CAS: 57184-23-3    CAS: 21043-40-3

CAS: 373356-51-5

Piperazine-aryl derivatives can be prepared by Medicinal Chemistry, 56(24), 10158-10170; 2013; PCT Int. Appl., 9900386, 7 Jan. 1999; Tetrahedron Letters, 47(15), 2549-2552; 2006; PCT Int. Appl., 2009095773, 6 Aug. 2009; U.S. Pat. Appl. Publ., 20140142114, 22 May 2014; Journal of Medicinal Chemistry, 57(3), 1063-1078; 2014; and PCT Int. Appl., 2010094126, 26 Aug. 2010.

Other cyclic amines and substituted cyclic amines are possible.

The general scheme below shows a method for coupling of an R3 C-groups ("C" in reaction scheme) with an aryl-fluoride (11) through an $S_NAr$ reaction (see, PCT Int. Appl., 2010097410, 2 Sep. 2010). The $S_NAR$ reaction is run at elevated temperatures (typically 100° C. or greater) with non-nucleophilic bases (like, $K_2CO_3$) in polar solvents (like, DMF or DMSO). The resulting intermediate (11) will give rise to a B group amine 12 by reduction of the nitrile 11 by any number of methods (Palladium and hydrogen, $PtO_2$ and hydrogen, Raney Nickel, Red-Al, Lithium aluminum hydride, Boranes).

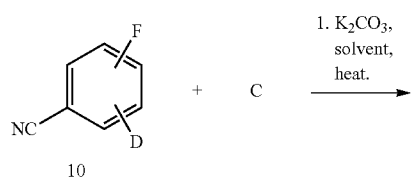

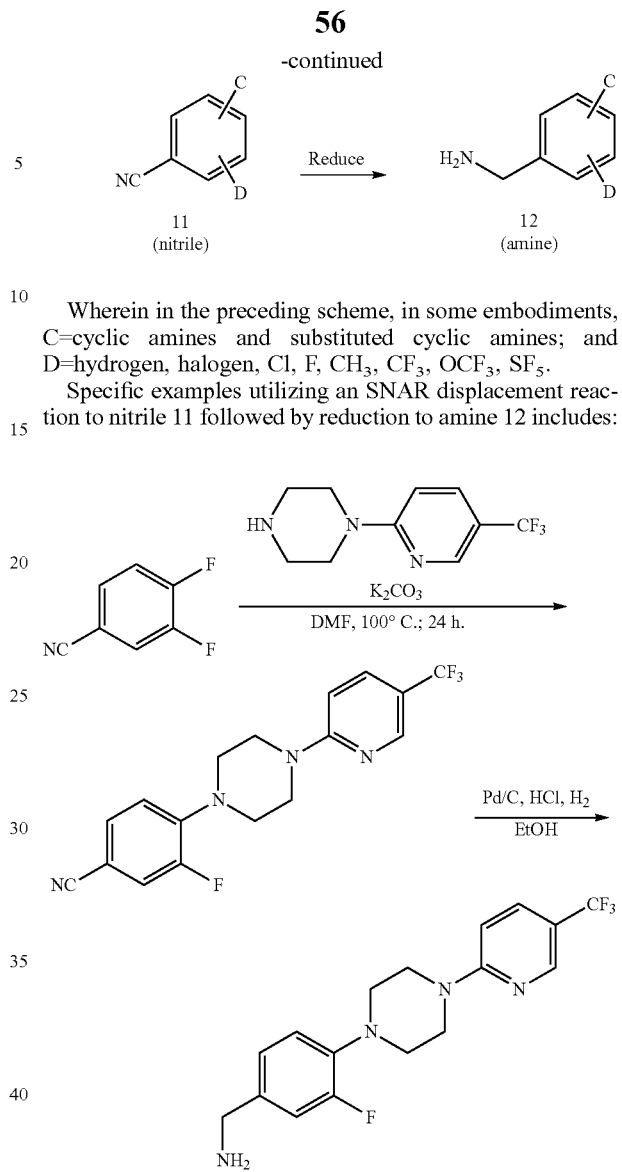

11 (nitrile)    12 (amine)

Wherein in the preceding scheme, in some embodiments, C=cyclic amines and substituted cyclic amines; and D=hydrogen, halogen, Cl, F, $CH_3$, $CF_3$, $OCF_3$, $SF_5$.

Specific examples utilizing an SNAR displacement reaction to nitrile 11 followed by reduction to amine 12 includes:

Which can be prepared by combining the [5-(trifluoromethyl)-2-pyridyl]piperazine [CAS: 132834-58-3](9 g, 38.9 mmol), potassium carbonate (10.8 g, 77.8 mmol) and the 3,4-difluorobenzenenitrile (5.4 g, 38.9 mmol) in 50 mL DMF. Reaction was heated to 100° C. overnight.

Reaction was blown to dryness with air and residue was taken up in EtOAc and washed with water (2x), brine and then dried over sodium sulfate. Drying agent was removed by filtration and organic layer was concentrated down to a tan solid. Crude solid can by purified through a silica gel column or recrystallized from hot isopropanol to give to give 11.95 g of 3-fluoro-4-(4-(5-(trifluoromethyl)pyridin-2-yl)piperazin-1-yl)benzonitrile as light yellow solid.

3-fluoro-4-(4-(5-(trifluoromethyl)pyridin-2-yl)piperazin-1-yl)benzonitrile (4.0 g, 11.4 mmol) was dissolved in 120 mL of EtOH. Next, 9.5 mL of HCl (114.2 mmol, 10 eq.) and Pd/c (5%, 2.43 g, 1.1 mmol) was added under argon. Three balloons of hydrogen gas was bubbled through solution and reaction stirred under 1 atm $H_2$ for 3 hours. Reaction was checked by TLC (ninhydrin stain, EtOH elute) and stopped once complete. At which time, reaction was filtered through glass paper (or celite) to remove palladium and washed with $CH_2Cl_2$ then filtrate was concentrated in vacuo. Residue was stirred in 4N NaOH (100 mL) for 10 mins (until basic) and extracted with CH₂Cl₂ (5×). Organic layer was washed with brine and then dried over sodium sulfate. Drying agent was removed by filtration and organics were concentrated down to 3.85 g of (3-fluoro-4-(4-(5-(trifluoromethyl)pyridin-2-yl)piperazin-1-yl)phenyl)methanamine as an off white solid.

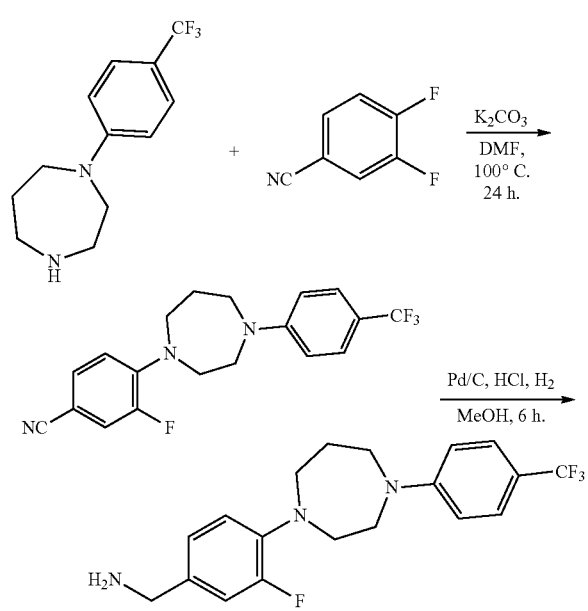

1-(4-(trifluoromethyl)phenyl)-1,4-diazepane [CAS: 868063-79-0] (2 g, 8.2 mmol) and potassium carbonate (1.7 g, 12.3 mmol) was dissolved in 25 mL DMF and the 3,4-difluorobenzenenitrile (1.14 g, 8.2 mmol) was added. Reaction heated to 100° C. overnight. Reaction was blown to dryness and residue was taken up in EtOAc and washed with water (2×), brine and then dried over Na₂SO₄. Drying agent was removed by filtration and organics were concentrated down. Residue can be purified by silica gel or recrystallized from hot isopropanol to give 2 grams of 3-fluoro-4-(4-(4-(trifluoromethyl)phenyl)-1,4-diazepan-1-yl)benzonitrile as a light tan solid.

3-fluoro-4-(4-(4-(trifluoromethyl)phenyl)-1,4-diazepan-1-yl)benzonitrile (2 g, 5.5 mmol) was dissolved in 50 mL of MeOH. Next, 4.6 mL HCl and Pd/c (5%, 1.2 g, 0.55 mmol) was added under argon. Two balloons of hydrogen gas was bubbled through solution and reaction stirred under 1 atm H₂ for 3 hours. Reaction was checked by TLC (ninhydrin stain, EtOH elute) and stopped once complete. At which time, reaction was filtered through glass paper (or celite) to remove palladium and washed with CH₂Cl₂ then filtrate was concentrated in vacuo. Residue was stirred in 4N NaOH (100 mL) for 10 mins (until basic) and extracted with CH₂Cl₂ (5×). Organic layer was washed with brine and then dried over sodium sulfate. Drying agent was removed by filtration and organics were concentrated down to give 1.8 g of (3-fluoro-4-(4-(4-(trifluoromethyl)phenyl)-1,4-diazepan-1-yl)phenyl)methanamine.

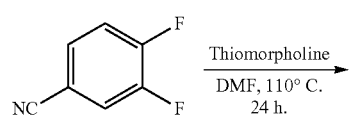

Thiomorpholine
DMF, 110° C.
24 h.

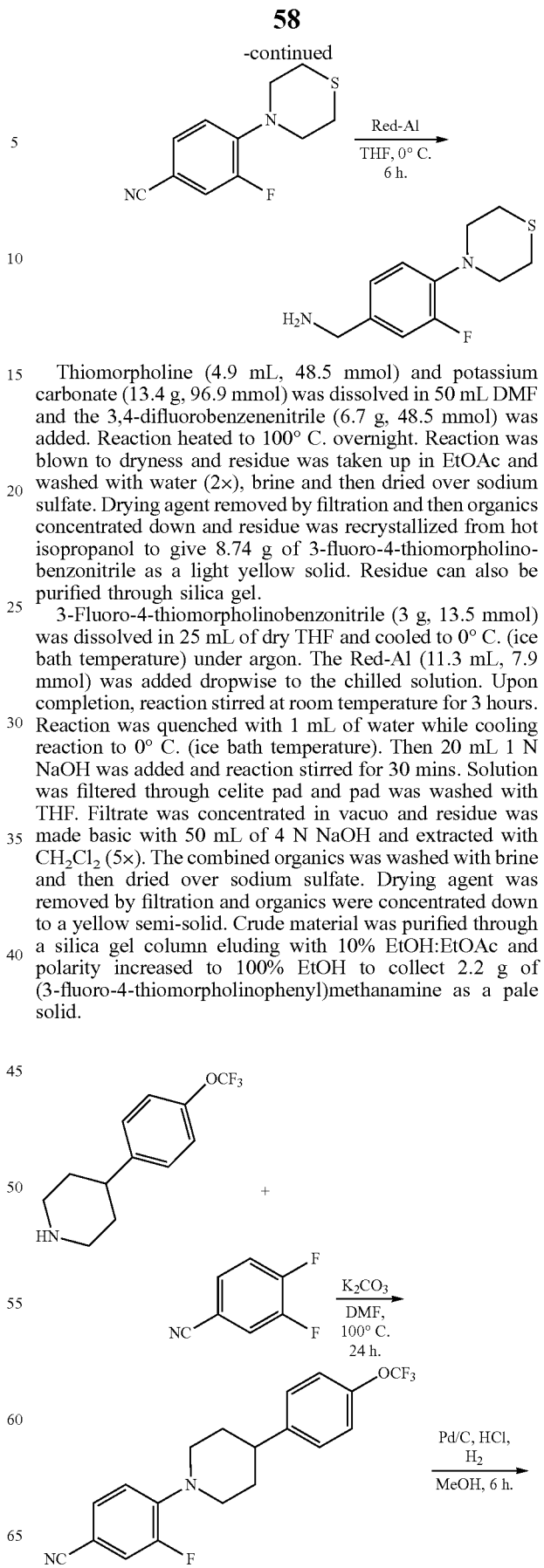

Thiomorpholine (4.9 mL, 48.5 mmol) and potassium carbonate (13.4 g, 96.9 mmol) was dissolved in 50 mL DMF and the 3,4-difluorobenzenenitrile (6.7 g, 48.5 mmol) was added. Reaction heated to 100° C. overnight. Reaction was blown to dryness and residue was taken up in EtOAc and washed with water (2×), brine and then dried over sodium sulfate. Drying agent removed by filtration and then organics concentrated down and residue was recrystallized from hot isopropanol to give 8.74 g of 3-fluoro-4-thiomorpholinobenzonitrile as a light yellow solid. Residue can also be purified through silica gel.

3-Fluoro-4-thiomorpholinobenzonitrile (3 g, 13.5 mmol) was dissolved in 25 mL of dry THF and cooled to 0° C. (ice bath temperature) under argon. The Red-Al (11.3 mL, 7.9 mmol) was added dropwise to the chilled solution. Upon completion, reaction stirred at room temperature for 3 hours. Reaction was quenched with 1 mL of water while cooling reaction to 0° C. (ice bath temperature). Then 20 mL 1 N NaOH was added and reaction stirred for 30 mins. Solution was filtered through celite pad and pad was washed with THF. Filtrate was concentrated in vacuo and residue was made basic with 50 mL of 4 N NaOH and extracted with CH₂Cl₂ (5×). The combined organics was washed with brine and then dried over sodium sulfate. Drying agent was removed by filtration and organics were concentrated down to a yellow semi-solid. Crude material was purified through a silica gel column eluding with 10% EtOH:EtOAc and polarity increased to 100% EtOH to collect 2.2 g of (3-fluoro-4-thiomorpholinophenyl)methanamine as a pale solid.

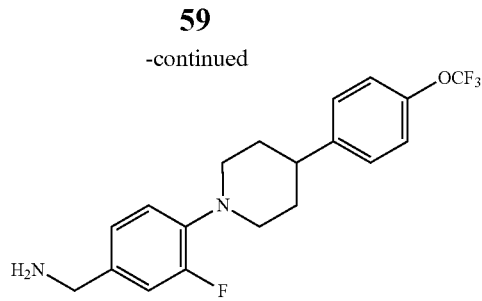

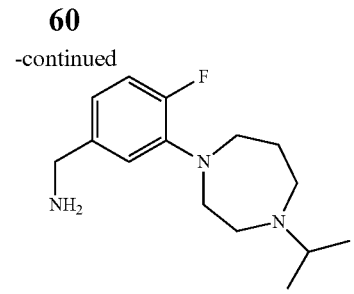

4-(4-(trifluoromethoxy)phenyl)piperidine [CAS: 180160-91-2] (2 g, 8.2 mmol) and potassium carbonate (2.3 g, 16.3 mmol) was dissolved in 25 mL DMF and the 3,4-difluorobenzenenitrile (1.14 g, 8.2 mmol) was added. Reaction heated to 100° C. overnight. Reaction was blown to dryness and residue was taken up in EtOAc and washed with water (2×), brine and then dried over $Na_2SO_4$. Drying agent was removed by filtration and organics were concentrated down. Residue can be purified by silica gel or recrystallized from hot isopropanol to give 1.75 grams of 3-fluoro-4-(4-(5-(trifluoromethylpyridin-2-yl)piperazin-1-yl)benzonitrile as a light tan solid.

3-fluoro-4-(4-(5-(trifluoromethyl)pyridin-2-yl)piperazin-1-yl)benzonitrile (1.75 g, 4.8 mmol) was dissolved in 50 mL of MeOH. Next, 4 mL HCl and Pd/c (5%, 1.0 g, 0.48 mmol) was added under argon. Two balloons of hydrogen gas was bubbled through solution and reaction stirred under 1 atm $H_2$ for 3 hours. Reaction was checked by TLC (ninhydrin stain, EtOH elute) and stopped once complete. At which time, reaction was filtered through glass paper (or celite) to remove palladium and washed with $CH_2Cl_2$ then filtrate was concentrated in vacuo. Residue was stirred in 4N NaOH (100 mL) for 10 mins (until basic) and extracted with $CH_2Cl_2$ (5×). Organic layer was washed with brine and then dried over sodium sulfate. Drying agent was removed by filtration and organics were concentrated down to give 1.1 g of (3-fluoro-4-(4-(5-(trifluoromethyl)pyridin-2-yl)piperazin-1-yl)phenyl)methanamine.

Alternatively, the formation of nitrile 11 can be accomplished through a buchwald palladium cross-coupling reaction as described in PCT Int. Appl., 2012113850, 30 Aug. 2012 for the preparation of piperidinylcarbonyl(homo)piperazines, in PCT Int. Appl., 2008076243, 26 Jun. 2008, and in PCT Int. Appl., 2013122897, 22 Aug. 2013.

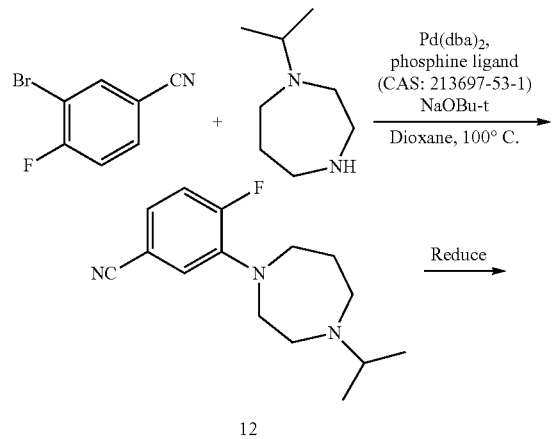

Additionally, the formation of the nitrile 12 can be accomplished through other methods. For instance, a titanium-mediated amination of Grignard reagents as described in Angewandte Chemie, International Edition, 2022, 50(36), 8325-8328. Which was used to prepare 4-fluoro-3-morpholinobenzonitrile which then can be reduced to the desired amine.

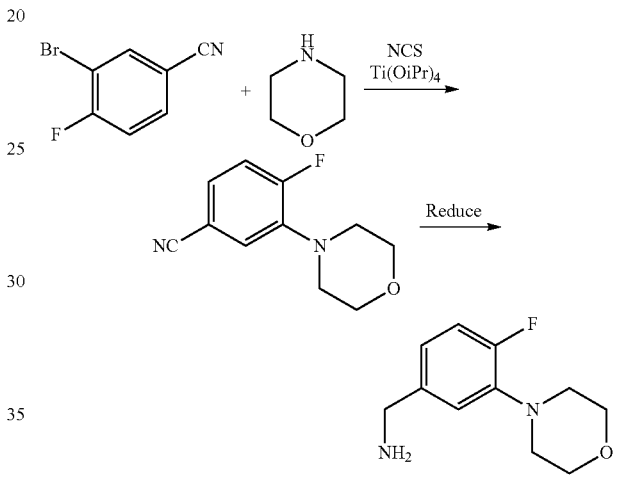

The nitriles 11 can also be reduced to amines 12 by borane as described in J. Med. Chem. 2007, 50, 3651-3660 for the preparation of (4-(2,6-Dimethylmorpholino)-3-fluorophenyl)methanamine hydrochloride.

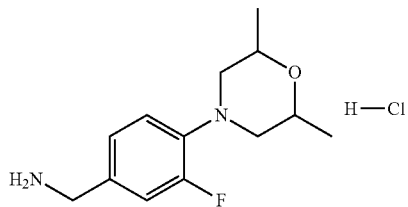

(4-(2,6-Dimethylmorpholino)-3-fluorophenyl)methanamine hydrochloride

Specifically, the 4-(2,6-dimethylmorpholino)-3-fluorobenzonitrile (1.23 g, 3.99 mmol) was taken up in 10 mL of THF followed by addition of 1M $BH_3$·THF (12.0 mL, 12.0 mmol), and the mixture was heated to reflux. After 2 h the solution was cooled to ambient temperature, and the reaction was quenched by careful addition of 3 N NaOH solution and stirred for 30 min. The mixture was partitioned between EtOAc and $H_2O$, and the separated organic phase was washed with brine, dried ($Na_2SO_4$), and concentrated in vacuo. Flash chromatography (5-10% $CH_3OH/CH_2Cl_2$) the title compound as a colorless oil. (2,5-Difluoro-4-(8-azaspiro[bicyclo[3.2.1]octane-3,2-[1,3]dioxolane]-8-yl)

phenyl)methanamine, yield 73% $^1$H NMR (DMSO-d$_6$): δ 7.18 (dd, J=14.6, 7.1 Hz, 1H), 6.77 (dd, J=12.6, 7.5 Hz, 1H), 4.28 (m, 2H), 3.94 (t, J=6.4 Hz, 2H), 3.70 (t, J=6.4 Hz, 2H), 3.61 (s, 2H), 2.03 (m, 2H), 1.64-1.94 (m, 8H).

The nitriles 11 can also be reduced to amines 12 by LiAlH$_4$ as described in U.S. Pat. Appl. 20050113576, 26 May 2005 for the preparation of hydrochloride.

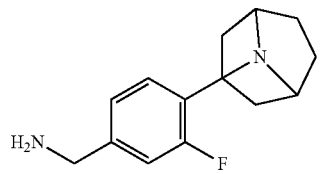

(4-(8-azabicyclo[3.2.1]octan-8-yl)-3-fluorophenyl)methanamine 4-(8-azabicyclo[3.2.1]oct-8-yl)-3-fluorobenzylamine. Lithium aluminum hydride (1.6 g; 43.2 mmol) in THF was treated with 4-(8-azabicyclo[3.2.1]oct-8-yl)-3-fluorobenzonitrile (2.48 g; 10.8 mmol) dropwise. After complete addition, the slurry was refluxed for 2 hours, allowed to cool to ambient temperature, and quenched with sodium sulfate decahydrate. The mixture was filtered and the filter cake was washed with THF (2×50 mL). The organics were combined and concentrated under reduced pressure. The residue was chromatographed (SiO2; 5% methanol in methylene chloride). 4-(8-azabicyclo[3.2.1]oct-8-yl)-3-fluorobenzylamine. 1H NMR (DMSO-d6) δ 7.03 (dd, 1H), 7.92 (dd, 1H), 7.85 (t, 1H), 4.21 (s, 2H), 3.60 (s, 2H), 1.93 (m, 2H), 1.77 (m, 5H), 1.42 (m, 1H), 1.32 (m, 2H).

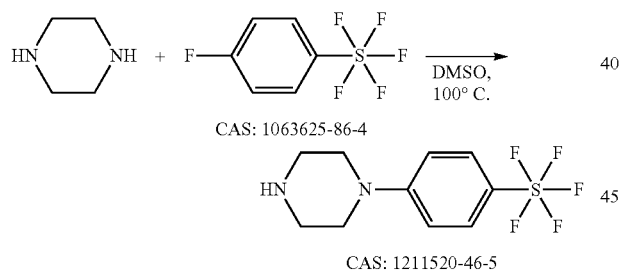

4-Fluorobenzopentafluorsulfide (CAS: 1063625-86-3, 1.0 g, 13.3 mmol) was dissolved in 6 mL DMSO and piperazine (2 g, 19.9 mmol) was added and reaction heated to 110° C. overnight (12 h). The reaction was concentrated to dryness and the residue was purified through a silica gel column (110 g) eluding with EtOAc (to remove upper running spot, di-coupled product) then solvent polarity was increased stepwise to 100% EtOH to collect 1.1 grams of 1-(4-(pentafluoro-λ$^6$-sulfanyl)phenyl)piperazine (most polar spot) $^1$H NMR (300 MHz, CDCl3) δ ppm 7.64 (d, J=9.1 Hz, 2H), 6.87 (d, J=8.9 Hz, 2H), 3.52-3.44 (m, 4H), 3.30-3.23 (m, 4H).

1-(3-(Pentafluoro-λ$^6$-sulfanyl)phenyl)piperazine (CAS: 1211581-17-7) can be prepared by the methods described above but using instead 3-Fluorobenzopentafluorsulfide (CAS: 1422-41-9).

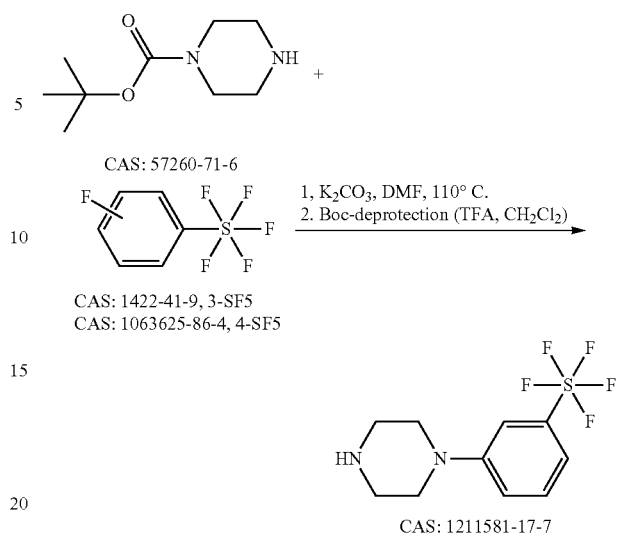

Alternatively, a Boc protected piperazine (CAS: 57260-71-6) can heated with 4-fluorobenzopentafluorsulfide or 3-fluorobenzopentafluorsulfide in an S$_N$Ar reaction. Then the coupled product is deprotection with trifuloroacetic anhydride (TFA) or HCl gas to give of 1-(4-(pentafluoro-λ$^6$-sulfanyl)phenyl)piperazine or 1-(3-(pentafluoro-λ$^6$-sulfanyl)phenyl)piperazine as the TFA or HCl, respectively. These salts can be neutralize with base (NaOH in methanol) to give the free amines.

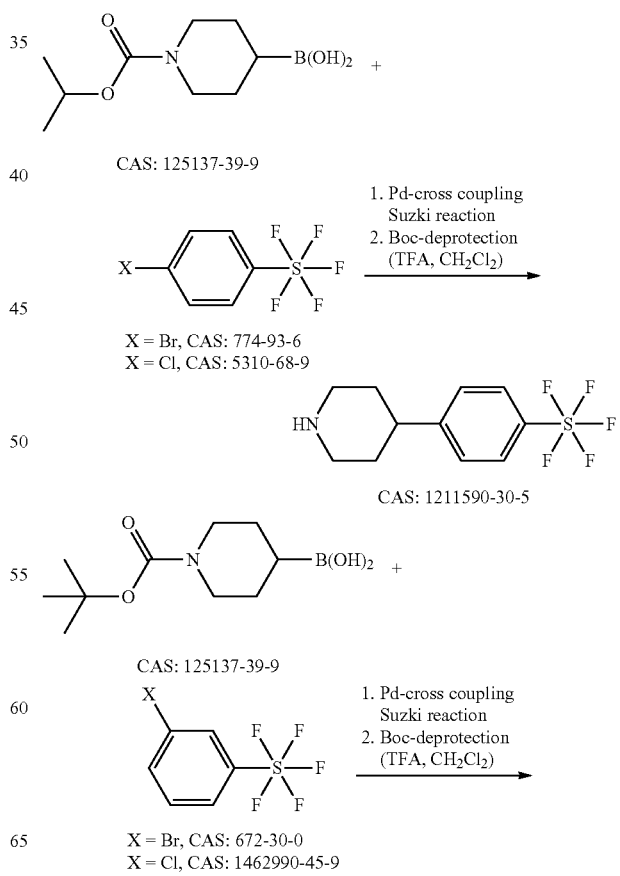

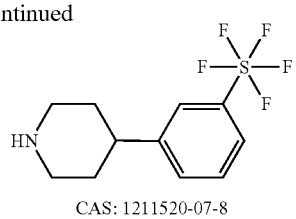

CAS: 1211520-07-8

4-(4-(pentafluoro-λ⁶-sulfanyl)phenyl)piperidine (CAS: 1211590-30-5) and 4-(3-(pentafluoro-λ⁶-sulfanyl)phenyl)piperidine (CAS: 1211520-07-8) can be prepared by the methods of 3. Med. Chem., 2014, 57 (12), 5293-5305 but using instead either 4-bromobenzopentafluorsulfide (CAS: 774-93-6), 4-chlorobenzopentafluorsulfide (CAS: 5310-68-9) or 3-bromobenzopentafluorsulfide (CAS: 672-30-0), 3-chlorobenzopentafluorsulfide (CAS: 1462990-45-9) as the halides within the Suzuki coupling reaction. The resulting product of the Suzuki coupling is deprotected with either trifluoroacetic acid (TFA) or HCl gas and then these salts can be neutralized with base to give the free amines.

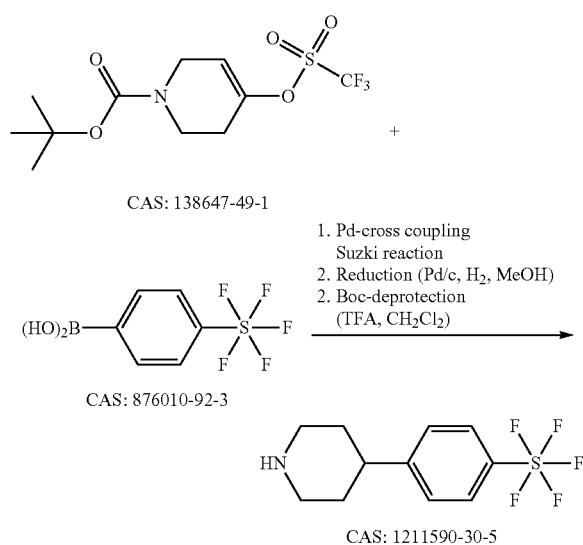

Alternatively, 4-(4-(pentafluoro-λ⁶-sulfanyl)phenyl)piperidine (CAS: 1211590-30-5) can be prepared by the methods in ACS Med. Chem. Lett., 2015, 6 (7), 814-818 but using instead (4-(pentafluoro-λ⁶-sulfanyl)phenyl)boronic acid (CAS: 876010-92-3) is used as the boronic acid in the Suzuki coupling reaction. The Suzuki reaction product is then reduced with palladium on carbon and hydrogen followed by Boc-deprotection and neutralization to give the free amine.

Coupling of amines 12 to heterocyclic cores (4a-4d; 8a-8d) is accomplished through standard amide bond formation reactions (as described in "The Practice of Peptide Synthesis," by M. Bodansky and A. Bodansky, Springer-Verlag, New York. 1994, 2nd ed.) or alternatively the carboxylic acids can be converted to an acid chlorides (via oxalyl chloride or thionyl chloride) and then stirring with 12 with base (trimethylamine, diisopropylethylamine, pyridine) in a non-protic solvent (CH₃CN, CH₂Cl₂, DMF).

Examples of amide coupling to prepare desired compounds include:

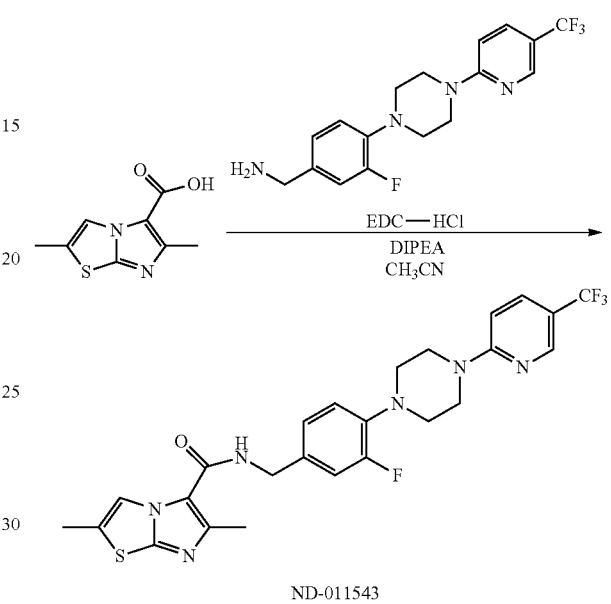

ND-011543

2,6-dimethylimidazo[2,1-b]thiazole-5-carboxylic acid (1.17 g, 5.9 mmol) was dissolved in dry CH₃CN and then the EDC-HCl (1.38 g, 7.2 mmol) was added and reaction stirred for 10 mins. Then (3-fluoro-4-(4-(5-(trifluoromethyl)pyridin-2-yl)piperazin-1-yl)phenyl)methanamine (2.29 g, 7.2 mmol) and diisopropylethylamine (1.3 mL, 7.2 mmol) were added in a round bottom flask. Reaction stirred for 12 hours under argon. Reaction was concentrated in vacuo. Residue was taken up in CH₂Cl₂ and washed with saturated aqueous NaHCO₃ solution (2×), 5% aqueous acetic acid solution (2×), brine and then dried over sodium sulfate. Drying agent was removed by filtration and organics were concentrated in vacuo. Resulting residue was purified by silica gel column or by recrystallization with hot CH₃CN to give N-(3-fluoro-4-(4-(5-(trifluoromethyl)pyridin-2-yl)piperazin-1-yl)benzyl)-2,6-dimethylimidazo[2,1-b]thiazole-5-carboxamide as an off white solid, 945 mg. 1H NMR (500 MHz, CDCl3) 8.42 (s, 1H), 7.99 (s, 1H), 7.67 (dd, J=8.9, 1.9 Hz, 1H), 7.38 (d, J=8.3 Hz, 1H), 7.31 (d, J=12.5 Hz, 1H), 6.95 (t, J=8.5, 8.5 Hz, 1H), 6.69 (d, J=9.0 Hz, 1H), 4.57 (d, J=5.4 Hz, 2H), 3.85-3.79 (m, 41-1), 3.35-3.30 (m, 4H).

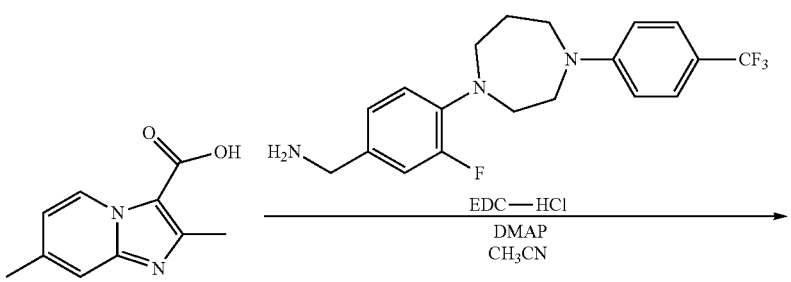

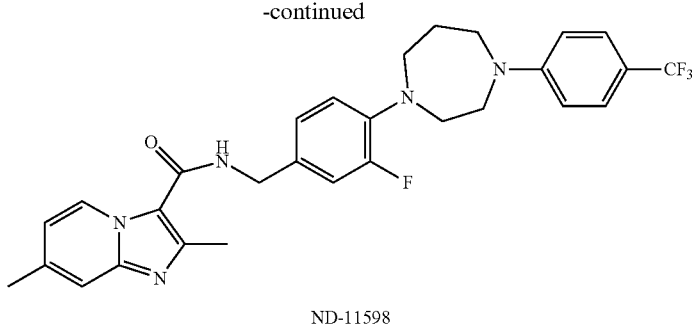

ND-11598

2,7-dimethylimidazo[1,2-a]pyridine-3-carboxylic acid (420 mg, 2.2 mmol) was dissolved in dry CH₃CN and then the EDC-HCl (510 mg, 2.6 mmol) was added and reaction stirred for 10 mins. Then the (3-fluoro-4-(4-(4-(trifluoromethyl)phenyl)-1,4-diazepan-1-yl)phenyOmethanam ine (878 mg, 2.3 mmol) and DMAP (323 mg, 2.7 mmol) were added in a round bottom flask under argon. Reaction stirred for 12 hours under argon. Reaction was concentrated in vacuo. Residue was taken up in CH₂Cl₂ and washed with saturated aqueous NaHCO₃ solution (2×), 5% aqueous acetic acid solution (2×), brine and then dried over sodium sulfate. Drying agent was removed by filtration and organics were concentrated in vacuo. Resulting residue was purified by silica gel column or by recrystallization with hot CH₃CN to give N-(3-fluoro-4-(4-(4-(trifluoromethyl)phenyl)-1,4-diazepan-1-yl)benzyl)-2,7-dimethylimidazo[1,2-a]pyridine-3-carboxamide as an off white solid, 847 mg.

¹H NMR (500 MHz, CDCl₃) δ ppm 9.30 (d, J=7.1 Hz, 1H), 7.43 (d, J=8.8 Hz, 2H), 7.32 (s, 1H), 6.86 (t, J=8.7, 8.7 Hz, 2H), 6.76 (d, J=7.2, 1H), 6.73 (d, J=8.8, 2H), 5.98 (bs, 1H, NH), 4.57 (d, J=5.7 Hz, 2H), 3.75-3.71 (m, 2H), 3.63 (t, J=6.2, 6.2 Hz, 2H), 3.54-3.50 (m, 2H), 3.30 (t, J=5.7, 5.7 Hz, 2H), 2.66 (s, 3H), 2.42 (s, 3I4), 2.13-2.04 (m, 2H).

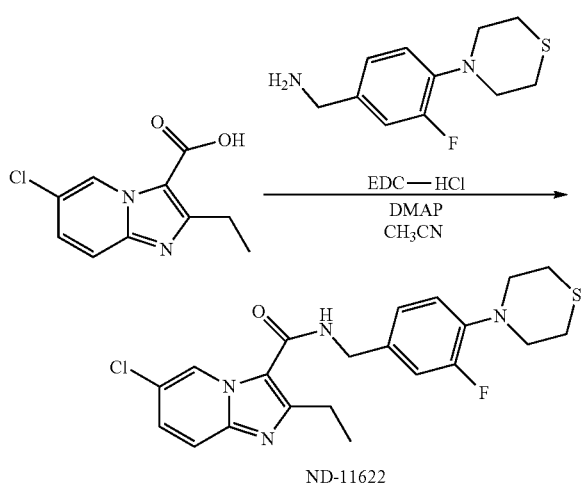

ND-11622

6-chloro-2-ethylimidazo[1,2-a]pyridine-3-carboxylic acid (900 mg, 4 mmol) was dissolved in dry CH₃CN and then the EDC-HCl (921 mg, 4.8 mmol) was added and reaction stirred for 10 mins. Then the (3-fluoro-4-thiomorpholinophenypmethanamine (998 mg, 4.4 mmol) and DMAP (587 mg, 4.8 mmol) were added in round bottom flask. Reaction stirred for 12 hours under argon. Reaction was concentrated in vacuo. Residue was taken up in CH₂Cl₂ and washed with saturated aqueous NaHCO3 solution (2×), 5% aqueous acetic acid solution (2×), brine and then dried over sodium sulfate. Drying agent was removed by filtration and organics were concentrated in vacuo. Resulting residue was purified by silica gel column or by recrystallization with hot CH₃CN to give 6-chloro-2-ethyl-N-(3-fluoro-4-thiomorpholinobenzyl)imidazo[1,2-a]pyridine-3-carboxamide, 777 mg. 1H NMR (500 MHz, CDCl3) δ ppm 9.50 (s, 1H), 7.56 (d, J=9.3 Hz, 1H), 7.32 (d, J=9.2 Hz, 1H), 7.06 (t, J=8.9, 8.9 Hz, 1H), 6.94 (t, J=8.4, 8.4 Hz, 1H), 6.25 (bs, 1H, NH), 4.61 (d, J=5.5 Hz, 1H), 3.35-3.26 (m, 4H), 2.99 (q, J=7.4 Hz, 2H), 2.84-2.77 (m, 4H), 1.41 (t, J=7.4, 7.4 Hz, 3H).

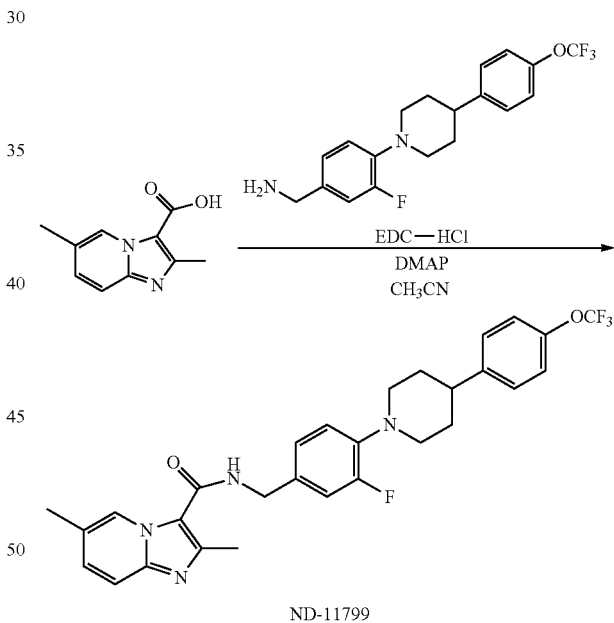

ND-11799

2,6-dimethylimidazo[1,2-a]pyridine-3-carboxylic acid (814 mg, 3.6 mmol) was dissolved in dry CH₃CN and then the EDC-HCl (757 mg, 3.9 mmol) was added and reaction stirred for 10 mins. Then (3-fluoro-4-(4-(4-(trifluoromethoxy)phenyl)piperidin-1-yl)phenyl)methanamine (1.19 g, 3.3 mmol) and DMAP (523 mg, 4.3 mmol) were added and reaction stirred under argon overnight. Reaction was concentrated in vacuo. Residue was taken up in CH2Cl2 and washed with saturated aqueous NaHCO3 solution (2×), 5% aqueous acetic acid solution (2×), brine and then dried over sodium sulfate. Drying agent was removed by filtration and organics were concentrated in vacuo. Resulting residue was purified by silica gel column or by recrystallization with hot CH₃CN to give N-(3-fluoro-4-(4-(4-(trifluoromethoxy)phenyl)piperidin-1-yl)benzyl)-2,6-dimethylimidazo[1,2-a]pyridine-3-carboxamide, 1.1 g.

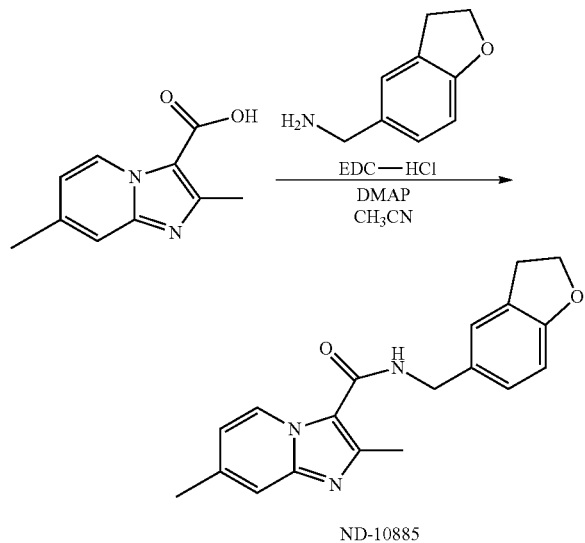

ND-10885

2,7-dimethylimidazo[1,2-a]pyridine-3-carboxylic acid (4 g, 21 mmol) and the EDC-HCl (4.8 g, 25.2 mmol) was added together and reaction stirred for 10 mins in dry CH₃CN. Then the 5-(Aminomethyl)-2,3-dihydrobenzo[b]furan (CAS: 55745-74-9, 3.5 g, 23.1 mmol) and DMAP (3.1 g, 25.2 mmol) were added and reaction stirred for 16 hours under argon. Reaction was concentrated in vacuo. Residue was taken up in CH₂Cl₂ and washed with saturated aqueous NaHCO₃ solution (2×), 5% aqueous acetic acid solution (2×), brine and then dried over sodium sulfate. Drying agent was removed by filtration and organics were concentrated in vacuo. Resulting residue was purified by silica gel column or by recrystallization with hot CH₃CN to give N-((2,3-dihydrobenzofuran-5-yl)methyl)-2,7-dimethylimidazo[1,2-a]pyridine-3-carboxamide as a white solid, 4.2 g. ¹H NMR (300 MHz, CDCl₃) δ ppm 9.28 (d, J=7.1 Hz, 1H), 7.37 (s, 1H), 7.21 (s, 1H), 7.10 (d, J=7.8 Hz, 1H), 6.75 (d, J=7.8 Hz, 1H), 6.04 (bs, 1H, NH) 4.58 (d, J=7.4 Hz, 1H), 4.55 (app. t, 2H, hidden), 3.19 (t, J=8.6, 8.6 Hz, 1H), 2.63 (s, 3H), 2.41 (s, 3H). ¹³C (126 MHz, CDCl₃) δ ppm 161.4, 159.7, 146.3, 138.4, 130.3, 127.7, 127.3, 127.2, 124.7, 115.7, 115.0, 114.9, 109.4, 71.4, 43.2, 29.7, 21.3, 16.7. Melting point=140-141.5° C. HRMS (EI), M+1 calcd. for C₁₉H₂₀N₃O₂, 322.1550; found 322.1568. HPLC $t_R$=1.2-1.4 min (99% pure).

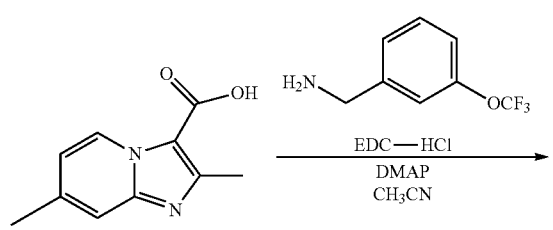

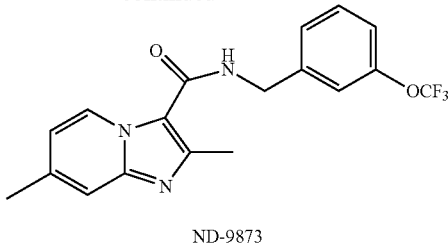

ND-9873

2,7-dimethylimidazo[1,2-a]pyridine-3-carboxylic acid (200 mg, 1 mmol) and EDC-HCl (287 mg, 1.5 mmol) were dissolved in 15 ml of dry CH₃CN (dried over sieves). Then the 3-trifluoromethoxybenzyl amine (0.15 mL, 1.06 mmol) and DMAP (305 mg, 2.5 mmol) were added. Reaction stirred at room temperature for 12 hours under argon. Reaction was concentrated in vacuo. Residue was taken up in CH₂Cl₂ and washed with saturated aqueous NaHCO₃ solution (2×), 5% aqueous acetic acid solution (2×), brine and then dried over sodium sulfate. Drying agent was removed by filtration and organics were concentrated in vacuo. Resulting residue was purified by silica gel column (with 10% EtOAc:CH₂Cl₂ to remove upper running amine and polarity was increased to 50% EtOAc:CH₂Cl₂ to collect product) or by recrystallization with hot CH₃CN to give 2,7-dimethyl-N-(3-(trifluoromethoxy)benzyl)imidazo[1,2-a]pyridine-3-carboxamide as a white solid, 265 mg. ¹H NMR (500 MHz, CDCl₃) δ ppm 9.24 (d, J=7.1 Hz, 1H), 7.36 (t, J=7.9, 7.9 Hz, 1H), 7.31-7.20 (m, 3H), 7.13 (d, J=8.0 Hz, 1H), 6.73 (d, J=7.1 Hz, 1H), 6.26 (bs, 1H, NH), 4.69 (d, J=5.9 Hz, 2H), 2.65 (s, 3H), 2.40 (s, 3H). ¹³C (126 MHz, CDCl₃) δ ppm 161.2, 149.5, 146.5, 145.5, 140.9, 138.5, 130.1, 127.2, 125.7, 120.7 (q, J=257.4 Hz), 120.0, 119.9, 115.8, 115.0, 114.7, 42.7, 21.3, 16.7. Melting point=110-111° C. HRMS (EI), M+1 calcd. for C₁₈H₁₇F₃N₃O₂, 364.1267; found 364.1271. HPLC $t_R$=2.8 min (99% pure).

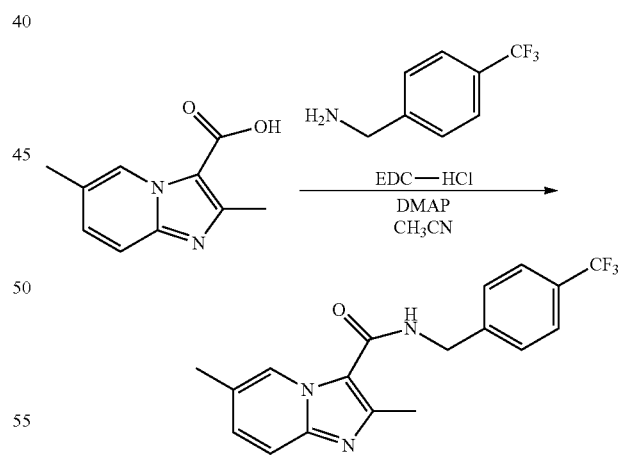

ND-11176

2,6-dimethylimidazo[1,2-a]pyridine-3-carboxylic acid (3.5 g, 18.4 mmol) was dissolved in dry CH₃CN and then the EDC-HCl (4.2 g, 22.1 mmol) was added and reaction stirred for 10 mins under argon. Then the 4-(trifluoromethoxy)benzyl amine (3.5 g, 20.2 mmol) and DMAP (2.7 g, 22.1 mmol) were added and reaction stirred for 16 hours under argon. Reaction was concentrated in vacuo. Residue was taken up in CH2Cl2 and washed with saturated aqueous NaHCO3 solution (2×), 5% aqueous acetic acid solution (2×), brine and then dried over sodium sulfate. Drying agent was removed by filtration and organics were concentrated in vacuo. Resulting residue was purified by silica gel column or by recrystallization with hot CH₃CN to give 2,6-dimethyl-N-(4-(trifluoromethyl)benzyl)imidazo[1,2-a]pyridine-3-carboxamide as a white solid, 5.1 grams. ¹H NMR (500 MHz, CDCl₃) δ ppm 9.25 (s, 1H), 7.66 (d, J=7.8 Hz, 1H), 7.55 (d, J=7.9 Hz, 1H), 7.29 (m, 4H), 6.38 (bs, 1H, NH), 4.79 (d, J=5.7 Hz, 2H), 2.75 (s, 3H), 2.40 (s, 3H). Melting point=110.5-111.1° C. HRMS (EI), M+1 calcd. for C₁₈H₁₇F₃N₃O, 348.1318; found 348.1332. HPLC t_R=2.7-2.9 min (99% pure).

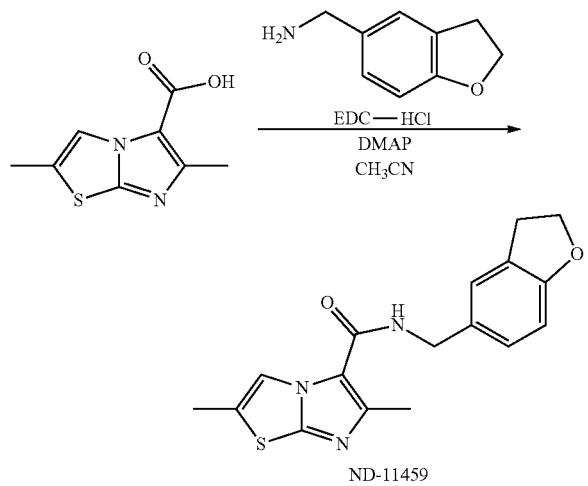

ND-11459

2,6-dimethylimidazo[2,1-b]thiazole-5-carboxylic acid (250 mg, 1.3 mmol) and EDC-HCl (268 mg, 1.4 mmol) was added together in 12 mL dry CH₃CN and reaction stirred for 10 mins. Then the 5-(Aminomethyl)-2,3-dihydrobenzo[b]furanhydrochloride salt (CAS: 635309-62-5, 236 mg, 1.4 mmol) and DMAP (342 g, 2.8 mmol) were added and reaction stirred for 16 hours under argon. Reaction was concentrated in vacuo. Residue was taken up in CH2Cl2 and washed with saturated aqueous NaHCO3 solution (2×), 5% aqueous acetic acid solution (2×), brine and then dried over sodium sulfate. Drying agent was removed by filtration and organics were concentrated in vacuo. Resulting residue was purified by silica gel column (DCM:EtOAc solvent gradient) or by recrystallization with hot CH₃CN to give N-((2,3-dihydrobenzofuran-5-yl)methyl)-2,6-dimethylimidazo[2,1-b]thiazole-5-carboxamide as a white solid (ND-11459), 173 mg. ¹H NMR (300 MHz, CDCl3) δ ppm 8.02 (s, Hz, 1H), 7.21 (s, 1H), 7.10 (d, J=8.0 Hz, 1H), 6.75 (d, J=8.13 Hz, 1H), 6.02 (bs, 1H, NH), 4.66-4.49 (m, 4H, overlap) 3.19 (t, J=8.7, 8.7 Hz, 1H), 2.59 (s, 3H), 2.45 (s, 3H).

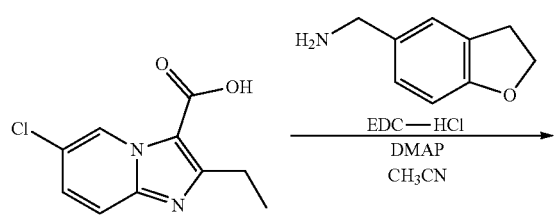

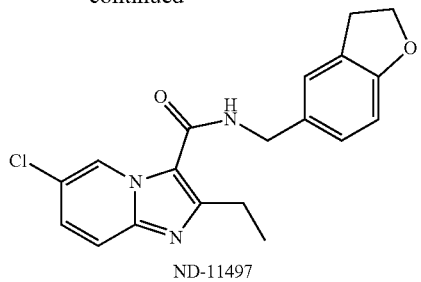

ND-11497

6-chloro-2-ethylimidazo[1,2-a]pyridine-3-carboxylic acid (107 mg, 0.48 mmol) and EDC-HCl (110 mg, 0.57 mmol) was added together in 5 mL of dry CH₃CN and reaction stirred for 10 mins. Then the 5-(Aminomethyl)-2,3-dihydrobenzo[b]furan hydrochloride salt (CAS: 635309-62-5, 100 mg, 0.52 mmol) and DMAP (128 g, 1.0 mmol) were added and reaction stirred for 16 hours under argon. Reaction was concentrated in vacuo. Residue was taken up in CH2Cl2 and washed with saturated aqueous NaHCO3 solution (2×), 5% aqueous acetic acid solution (2×), brine and then dried over sodium sulfate. Drying agent was removed by filtration and organics were concentrated in vacuo. Resulting residue was purified by silica gel column (DCM:EtOAc solvent gradient) or by recrystallization with hot CH₃CN to give 6-chloro-N-((2,3-dihydrobenzofuran-5-yl)methyl)-2-ethylimidazo[1,2-a]pyridine-3-carboxamide (ND-11497) as a white solid, 81 mg. ¹H NMR (300 MHz, CDCl3) δ ppm 9.53 (s, 1H), 7.54 (d, J=9.5 Hz, 1H), 7.24 (m, 2H), 7.11 (d, J=7.0 Hz, 1H), 6.77 (d, J=8.0 Hz, 1H), 6.08 (bs, 1H, NH2), 4.58 (m, 4H, overlap), 3.22 (d, J=8.5 Hz, 2H), 2.96 (d, J=7.41 Hz, 2H), 1.39 (t, J=7.2, 7.2 Hz, 3H).

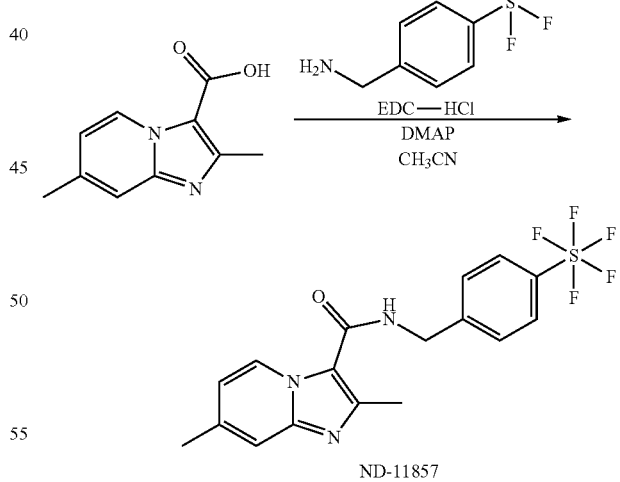

ND-11857

2,7-dimethylimidazo[1,2-a]pyridine-3-carboxylic acid (150 mg, 0.79 mmol) was dissolved in 7 mL dry CH₃CN and then the EDC-HCl (181 mg, 0.95 mmol) was added and reaction stirred for 10 mins. 4-(Pentafluorosulfur)benzylamine (CAS: 771573-35-4, 202 mg, 0.87 mmol) and DMAP (116 mg, 0.95 mmol) were added in a round bottom flask under argon. Reaction stirred for 12 hours under argon. Reaction was concentrated in vacuo. Residue was taken up in CH₂C₁₂ and washed with saturated aqueous NaHCO₃ solution (2×), 5% aqueous acetic acid solution (2×), brine and then dried over sodium sulfate. Drying agent was removed by filtration and organics were concentrated in vacuo. Resulting residue was purified by silica gel column (DCM:EtOAc solvent gradient) or by recrystallization with hot CH₃CN to give 180 mg of 2,7-dimethyl-N-(4-(pentafluoro-λ⁶-sulfanyl)benzyl)imidazo[1,2-a]pyridine-3-carboxamide (ND-11857) as a white solid. Mp=186-187° C., benzoic acid standard measured at 113-114° C.; ¹H NMR (300 MHz, CDCl3) δ ppm 9.20 (d, J=7.1 Hz, 1H), 7.73 (d, J=8.6 Hz, 2F1), 7.47 (d, J=8.3 Hz, 2H), 7.40 (s, 1H), 6.77 (d, J=7.1 Hz, 1H), 6.51 (bs, 1H, NH2), 4.72 (d, J=5.9 Hz, 2H), 2.69 (s, 3H), 2.41 (s, 3H). ¹⁹F NMR (282 MHz, CDCl3) δ ppm 84.4 (penta, J=150.0 Hz, 1F), 63.0 (d, J=150.07 Hz, 4F).

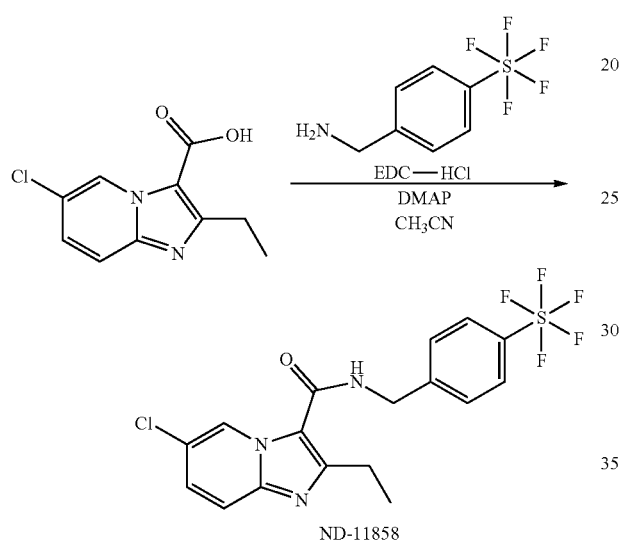

ND-11858

6-chloro-2-ethylimidazo[1,2-a]pyridine-3-carboxylic acid (150 mg, 0.66 mmol) was dissolved in 7 mL dry CH₃CN and then the EDC-HCl (153 mg, 0.80 mmol) was added and reaction stirred for 10 mins. 4-(Pentafluorosulfur)benzylamine (CAS: 771573-35-4, 171 mg, 0.73 mmol) and DMAP (98 mg, 0.80 mmol) were added in a round bottom flask under argon. Reaction stirred for 12 hours under argon. Reaction was concentrated in vacuo. Residue was taken up in CH₂Cl₂ and washed with saturated aqueous NaHCO₃ solution (2×), 5% aqueous acetic acid solution (2×), brine and then dried over sodium sulfate. Drying agent was removed by filtration and organics were concentrated in vacuo. Resulting residue was purified by silica gel column (DCM:EtOAc solvent gradient) or by recrystallization with hot CH₃CN to give 115 mg of 6-chloro-2-ethyl-N-(4-(pentafluoro-λ⁶-sulfanyl)benzyl)imidazo[1,2-a]pyridine-3-carboxamide (ND-11858) as a white solid. Mp=191-192° C., benzoic acid standard measured at 113-114° C.; ¹H NMR (300 MHz, CDCl3) δ ppm 9.50 (s, 1H), 7.75 (d, J=8.6 Hz, 2H), 7.55 (d, J=9.5 Hz, 1H), 7.46 (d, J=8.3 Hz, 2H), 7.32 (d, J=9.5 Hz, 1H), 6.30 (bs, 1H, NH2) 4.74 (d, J=5.9 Hz, 2H), 3.01 (q, J=7.5, 7.5, 7.5 Hz, 2H), 1.43 (t, J=7.5, 7.5 Hz, 3H). ¹⁹F NMR (282 MHz, CDCl3) δ ppm 84.4 (penta, J=150.1 Hz, 1F), 63.0 (d, J=150.1 Hz, 4F).

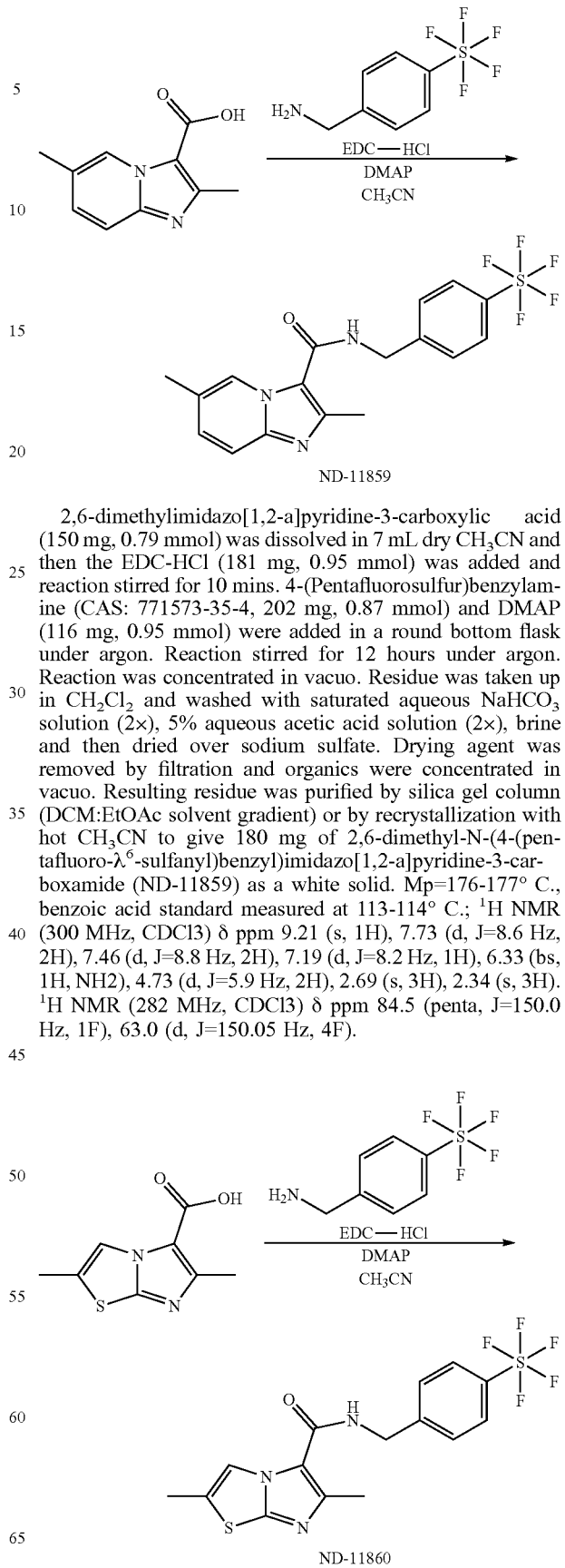

ND-11859

2,6-dimethylimidazo[1,2-a]pyridine-3-carboxylic acid (150 mg, 0.79 mmol) was dissolved in 7 mL dry CH₃CN and then the EDC-HCl (181 mg, 0.95 mmol) was added and reaction stirred for 10 mins. 4-(Pentafluorosulfur)benzylamine (CAS: 771573-35-4, 202 mg, 0.87 mmol) and DMAP (116 mg, 0.95 mmol) were added in a round bottom flask under argon. Reaction stirred for 12 hours under argon. Reaction was concentrated in vacuo. Residue was taken up in CH₂Cl₂ and washed with saturated aqueous NaHCO₃ solution (2×), 5% aqueous acetic acid solution (2×), brine and then dried over sodium sulfate. Drying agent was removed by filtration and organics were concentrated in vacuo. Resulting residue was purified by silica gel column (DCM:EtOAc solvent gradient) or by recrystallization with hot CH₃CN to give 180 mg of 2,6-dimethyl-N-(4-(pentafluoro-λ⁶-sulfanyl)benzyl)imidazo[1,2-a]pyridine-3-carboxamide (ND-11859) as a white solid. Mp=176-177° C., benzoic acid standard measured at 113-114° C.; ¹H NMR (300 MHz, CDCl3) δ ppm 9.21 (s, 1H), 7.73 (d, J=8.6 Hz, 2H), 7.46 (d, J=8.8 Hz, 2H), 7.19 (d, J=8.2 Hz, 1H), 6.33 (bs, 1H, NH2), 4.73 (d, J=5.9 Hz, 2H), 2.69 (s, 3H), 2.34 (s, 3H). ¹H NMR (282 MHz, CDCl3) δ ppm 84.5 (penta, J=150.0 Hz, 1F), 63.0 (d, J=150.05 Hz, 4F).

ND-11860

2,6-dimethylimidazo[2,1-b]thiazole-5-carboxylic acid (150 mg, 0.76 mmol) was dissolved in 7 mL dry $CH_3CN$ and then the EDC-HCl (196 mg, 0.92 mmol) was added and reaction stirred for 10 mins. 4-(Pentafluorosulfur)benzylamine (CAS: 771573-35-4, 196 mg, 0.84 mmol) and DMAP (112 mg, 0.92 mmol) were added in a round bottom flask under argon. Reaction stirred for 12 hours under argon. Reaction was concentrated in vacuo. Residue was taken up in $CH_2Cl_2$ and washed with saturated aqueous $NaHCO_3$ solution (2×), 5% aqueous acetic acid solution (2×), brine and then dried over sodium sulfate. Drying agent was removed by filtration and organics were concentrated in vacuo. Resulting residue was purified by silica gel column (DCM:EtOAc solvent gradient) or by recrystallization with hot $CH_3CN$ to give 131 mg of 2,6-dimethyl-N-(4-(pentafluoro-$\lambda^6$-sulfanyl)benzyl)imidazo[2,1-b]thiazole-5-carboxamide (ND-11860) as a white solid. Mp=147-148° C., benzoic acid standard measured at 113-114° C.; $^1$H NMR (300 MHz, CDCl3) δ ppm 7.96 (s, 1H), 7.73 (d, J=8.7 Hz, 2H), 7.44 (d, J=8.3 Hz, 2H), 6.17 (bs, 1H, NH2), 4.69 (d, =6.0 Hz, 2H), 2.59 (s, 3H), 2.42 (s, 3H). $^{19}$F NMR (282 MHz, CDCl3) δ ppm 84.5 (penta, J=150.1 Hz, 1F), 63.0 (d, J=150.04 Hz, 4F).

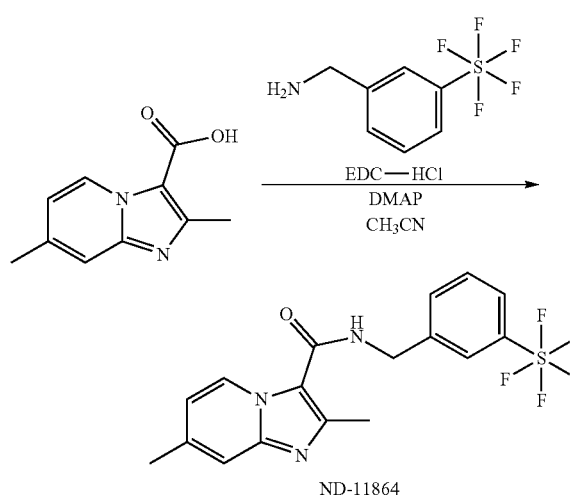

ND-11864

2,7-dimethylimidazo[1,2-a]pyridine-3-carboxylic acid (100 mg, 0.52 mmol) was dissolved in 5 mL dry $CH_3CN$ and then the EDC-HCl (82 mg, 0.57 mmol) was added and reaction stirred for 10 mins. 3-(Pentafluorosulfur)benzylamine (CAS: 771573-34-3, 134 mg, 0.57 mmol) and DMAP (77 mg, 0.63 mmol) were added in a round bottom flask under argon. Reaction stirred for 12 hours under argon. Reaction was concentrated in vacuo. Residue was taken up in $CH_2Cl_2$ and washed with saturated aqueous $NaHCO_3$ solution (2×), 5% aqueous acetic acid solution (2×), brine and then dried over sodium sulfate. Drying agent was removed by filtration and organics were concentrated in vacuo. Resulting residue was purified by silica gel column (DCM:EtOAc solvent gradient) or by recrystallization with hot $CH_3CN$ to give 111 mg of 2,7-dimethyl-N-(3-(pentafluoro-$\lambda^6$-sulfanyl)benzyl)imidazo[1,2-a]pyridine-3-carboxamide (ND-11864) as a white solid. $^1$H NMR (300 MHz, CDCl3) δ ppm 9.25 (d, J=7.1 Hz, 1H), 7.77 (s, 1H), 7.68 (d, J=8.1 Hz, 1H), 7.33 (s, 1H), 7.59-7.41 (m, 2H), 6.78 (d, J=7.1, 1H), 6.32 (bs, 1F1, NH2), 4.75 (d, J=6.0 Hz, 2H), 2.68 (s, 3H), 2.42 (s, 3H). $^{19}$F NMR (282 MHz, CDCl3) δ ppm 84.4 (penta, J=149.5 Hz, 1F), 62.9 (d, J=150.00 Hz, 4F).

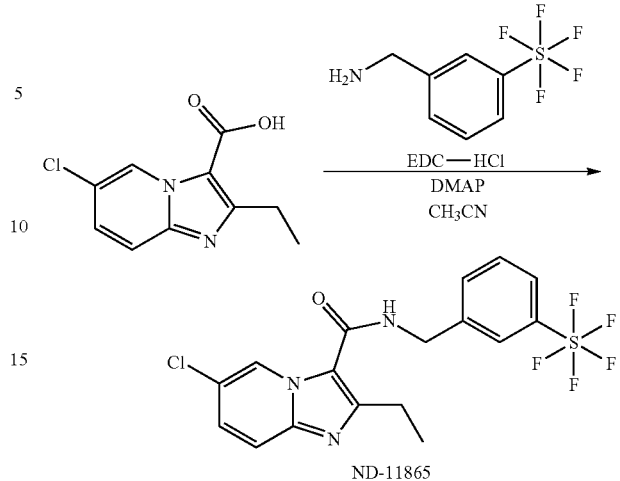

ND-11865

6-chloro-2-ethylimidazo[1,2-a]pyridine-3-carboxylic acid (100 mg, 0.45 mmol) was dissolved in 5 mL dry $CH_3CN$ and then the EDC-HCl (69 mg, 0.45 mmol) was added and reaction stirred for 10 mins. 3-(Pentafluorosulfur)benzylamine (CAS: 771573-34-3, 114 mg, 0.49 mmol) and DMAP (65 mg, 0.53 mmol) were added in a round bottom flask under argon. Reaction stirred for 12 hours under argon. Reaction was concentrated in vacuo. Residue was taken up in $CH_2Cl_2$ and washed with saturated aqueous $NaHCO_3$ solution (2×), 5% aqueous acetic acid solution (2×), brine and then dried over sodium sulfate. Drying agent was removed by filtration and organics were concentrated in vacuo. Resulting residue was purified by silica gel column (DCM:EtOAc solvent gradient) or by recrystallization with hot $CH_3CN$ to give 71 mg of 6-chloro-2-ethyl-N-(3-(pentafluoro-$\lambda^6$-sulfanyl)benzyl)imidazo[1,2-a]pyridine-3-carboxamide (ND-11865) as a white solid. $^1$H NMR (300 MHz, CDCl3) δ ppm 9.49 (s, 1H), 7.77 (s, 111), 7.70 (d, J=8.0 Hz, 1H), 7.63-7.43 (m, 4H), 7.33 (d, J=9.4 Hz, 1F1), 6.36 (bs, 1H, NH2), 4.76 (d, J=5.9 Hz, 2H), 3.02 (q, J=7.5, 7.5, 7.5 Hz, 2H), 1.42 (t, J=7.5, 7.5 Hz, 3H). $^1$H NMR (282 MHz, CDCl3) δ ppm 84.6 (penta, J=149.8 Hz, 1F), 62.8 (d, J=150.00 Hz, 4F).

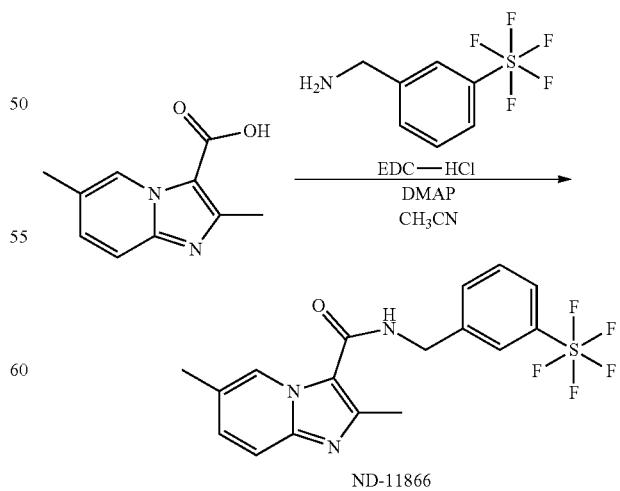

ND-11866

2,6-dimethylimidazo[1,2-a]pyridine-3-carboxylic acid (100 mg, 0.52 mmol) was dissolved in 5 mL dry $CH_3CN$ and then the EDC-HCl (82 mg, 0.57 mmol) was added and reaction stirred for 10 mins. 3-(Pentafluorosulfur)benzylamine (CAS: 771573-34-3, 134 mg, 0.57 mmol) and DMAP (77 mg, 0.63 mmol) were added in a round bottom flask under argon. Reaction stirred for 12 hours under argon. Reaction was concentrated in vacuo. Residue was taken up in CH$_2$Cl$_2$ and washed with saturated aqueous NaHCO$_3$ solution (2×), 5% aqueous acetic acid solution (2×), brine and then dried over sodium sulfate. Drying agent was removed by filtration and organics were concentrated in vacuo. Resulting residue was purified by silica gel column (DCM:EtOAc solvent gradient) or by recrystallization with hot CH$_3$CN to give 75 mg of 2,6-dimethyl-N-(3-(pentafluoro-λ$^6$-sulfanyl)benzyl)imidazo[1,2-a]pyridine-3-carboxamide (ND-11866) as a white solid. $^1$H NMR (300 MHz, CDCl3) δ ppm 9.19 (s, 1H), 7.77 (s, 1H), 7.69 (d, J=8.2 Hz, 1H), 7.60-7.45 (m, 3H), 7.21 (d, J=9.1 Hz, 1H), 6.34 (bs, 1H, NH2), 4.76 (d, J=6.0 Hz, 2H), 2.70 (s, 3H), 2.36 (s, 3H). $^{19}$F NMR (282 MHz, CDCl3) δ ppm 84.4 (penta, J=149.5 Hz, 1F), 62.3 (d, J=150.00 Hz, 4F).

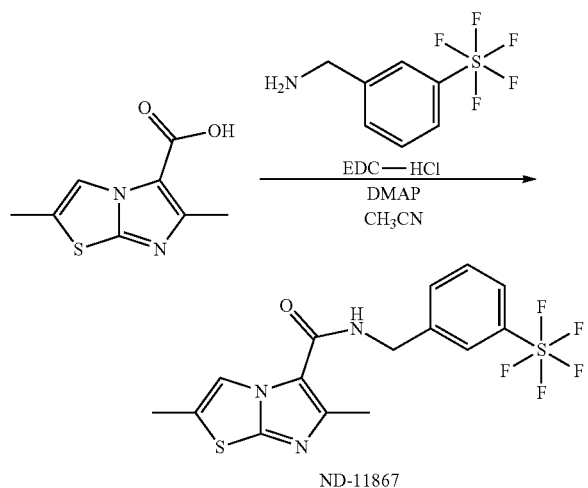

2,6-dimethylimidazo[2,1-b]thiazole-5-carboxylic acid acid (100 mg, 0.51 mmol) was dissolved in 5 mL dry CH$_3$CN and then the EDC-HCl (72 mg, 0.46 mmol) was added and reaction stirred for 10 mins. 3-(Pentafluorosulfur)benzylamine (CAS: 771573-34-3, 118 mg, 0.51 mmol) and DMAP (68 mg, 0.55 mmol) were added in a round bottom flask under argon. Reaction stirred for 12 hours under argon. Reaction was concentrated in vacuo. Residue was taken up in CH$_2$Cl$_2$ and washed with saturated aqueous NaHCO$_3$ solution (2×), 5% aqueous acetic acid solution (2×), brine and then dried over sodium sulfate. Drying agent was removed by filtration and organics were concentrated in vacuo. Resulting residue was purified by silica gel column (DCM:EtOAc solvent gradient) or by recrystallization with hot CH$_3$CN to give 109 mg of 2,6-dimethyl-N-(3-(pentafluoro-λ$^6$-sulfanyl)benzyl)imidazo[2,1-b]thiazole-5-carboxamide (ND-11867) as a white solid. $^1$H NMR (300 MHz, CDCl3) δ ppm 7.97 (s, 1H), 7.74 (s, 1H), 7.69 (d, J=8.2 Hz, 1H), 7.55-7.43 (m, 2H), 6.07 (bs, 1H, NH2), 4.72 (d, J=6.0 Hz, 2H), 2.59 (s, 3H), 2.44 (s, 3H).

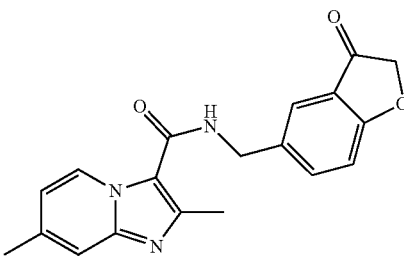

2,7-dimethyl-N-((3-oxo-2,3-dihydrobenzofuran-5yl)methyl)imidazo[1,2-a]pyridine-3-carboxamide 2,7-dimethylimidazo[1,2-a]pyridine-3-carboxylic acid (1 mmol) and the EDC-HCl (1.2 mmol) was added together and reaction stirred for 10 mins in dry CH$_3$CN. Then 5-(aminomethyl)benzofuran-3(2H)-one (CAS: 1630261-74-3) (1.1 mmol) and DMAP (1.2 mmol) were added and reaction stirred for 16 hours under argon. Reaction was concentrated in vacuo.

Residue was taken up in CH2Cl2 and washed with saturated aqueous NaHCO3 solution (2×), 5% aqueous acetic acid solution (2×), brine and then dried over sodium sulfate. Drying agent was removed by filtration and organics were concentrated in vacuo. Resulting residue was purified by silica gel column (CH2Cl2:EtOAc or EtOAc:EtOH gradient) or by recrystallization from hot CH$_3$CN to give desired product 2,7-dimethyl-N-((3-oxo-2,3-dihydrobenzofuran-5-yl)methyl)imidazo[1,2-a]pyridine-3-carboxamide

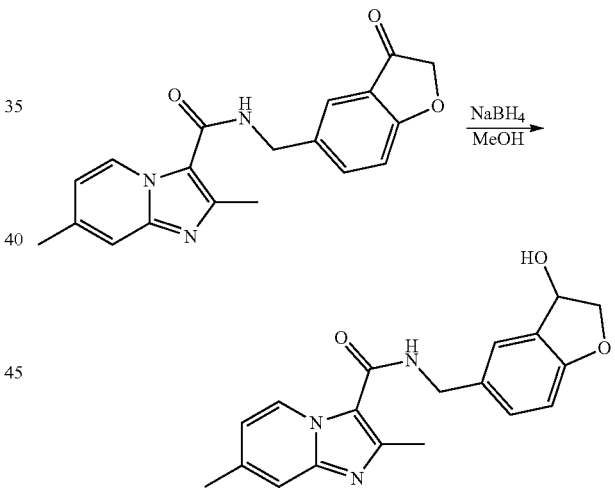

2,7-dimethyl-N-((3-oxo-2,3-dihydrobenzofuran-5-yl)methyl)imidazo[1,2-a]pyridine-3-carboxamide was can be reduced by NaBH4 as described in Tetrahedron, 45(5), 1441-6; 1989 or Beilstein Journal of Organic Chemistry, 6, 1061-1069, No. 121; 2010.

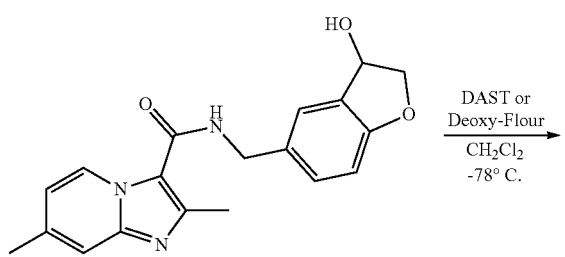

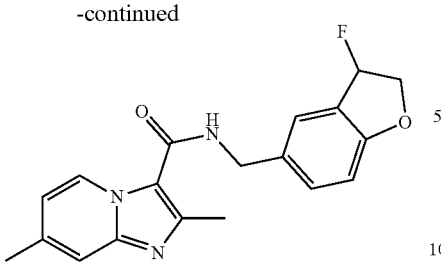

The alcohol can be converted to fluoride with use of DAST as in Journal of Heterocyclic Chemistry, 45(3), 887-896; 2008.

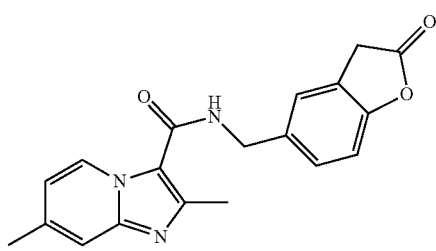

2,7-dimethyl-N-((2-oxo-2,3-dihydrobenzofuran-5-yl)methyl)imidazo[1,2-a]pyridine-3-carboxamide 2,7-dimethylimidazo[1,2-a]pyridine-3-carboxylic acid (1 mmol) and the EDC-HCl (1.2 mmol) was added together and reaction stirred for 10 mins in dry CH3CN. Then 5-(aminomethyl)benzofuran-2(3H)-one (CAS: 16933726-57-9) (1.1 mmol) and DMAP (1.2 mmol) were added and reaction stirred for 16 hours under argon. Reaction was concentrated in vacuo.

Residue was taken up in CH2Cl2 and washed with saturated aqueous NaHCO3 solution (2×), 5% aqueous acetic acid solution (2×), brine and then dried over sodium sulfate. Drying agent was removed by filtration and organics were concentrated in vacuo. Resulting residue was purified by silica gel column (CH$_2$Cl$_2$:EtOAc or EtOAc:EtOH gradient) or by recrystallization from hot CH3CN to give desired product 2,7-dimethyl-N-((2-oxo-2,3-dihydrobenzofuran-5-yl)methyl)imidazo[1,2-a]pyridine-3-carboxamide.

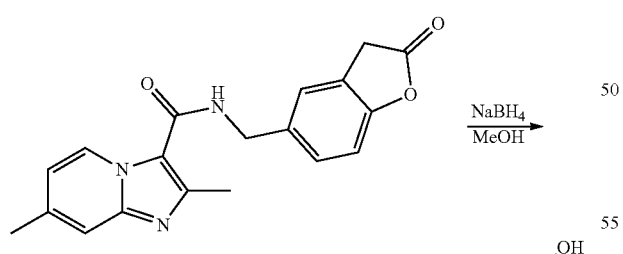

2,7-dimethyl-N-((3-oxo-2,3-dihydrobenzofuran-5-yl)methyl)imidazo[1,2-a]pyridine-3-carboxamide was can be reduced by NaBH4 as described in Tetrahedron, 45(5), 1441-6; 1989 or Beilstein Journal of Organic Chemistry, 6, 1061-1069, No. 121; 2010.

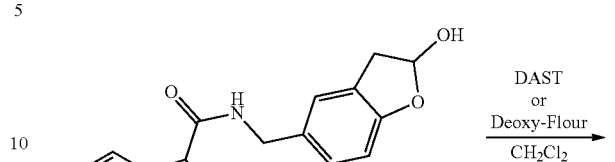

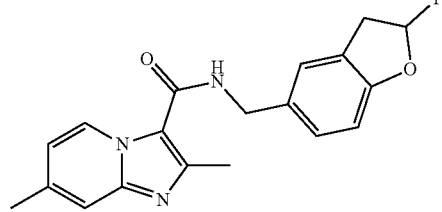

The alcohol can be converted to fluoride with use of DAST as in Journal of Heterocyclic Chemistry, 45(3), 887-896; 2008.

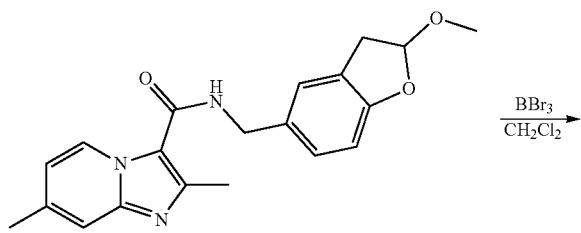

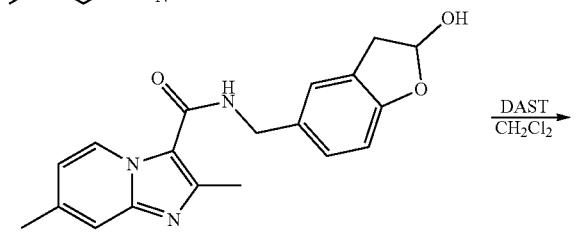

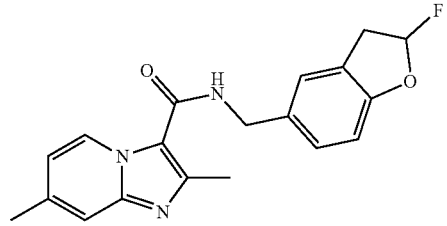

Alternatively, the hydroxyl compound can be arrived at through the synthesis of N-((2-methoxy-2,3-dihydrobenzofuran-5-yl)methyl)-2,7-dimethylimidazo[1,2-a]pyridine-3-carboxamide followed by subsequent demethylated by bromine tribromide (BBr$_3$) by the method in Bioorganic & Medicinal Chemistry Letters, 19(16), 4882-4884; 2009.

N-((2-methoxy-2,3-dihydrobenzofuran-5-yl)methyl)-2,7-di methylimidazo[1,2-a]pyridine-3-carboxamide is prepared by an EDC mediated coupling of 2,7-dimethylimidazo[1,2-a]pyridine-3-carboxylic acid and (2-methoxy-2,3-dihydrobenzofuran-5-yl)methanamine (CAS: 1431851-43-2) by the general procedure described previously.

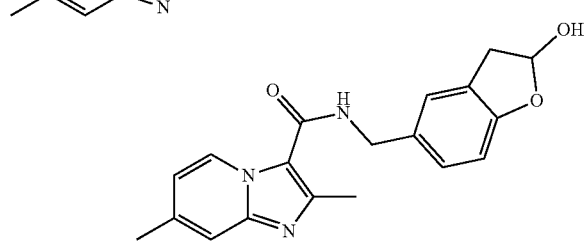

Each of the compounds shown in the figures are hereby incorporated and made part of this description.

The entire contents of each reference, patent document, article, and the like described herein are hereby independently incorporated by reference.

What is claimed is:

1. A compound, having one of the following formulas:

ND-011544
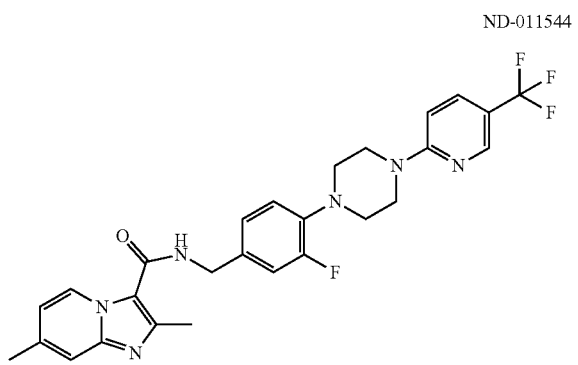

ND-011598
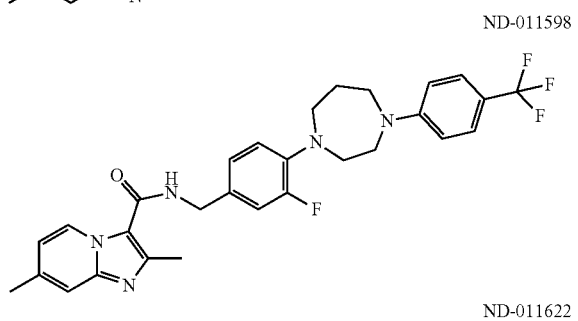

ND-011622
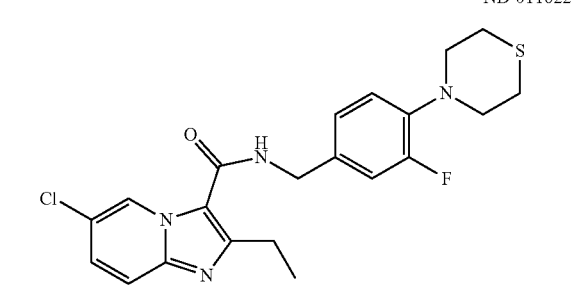

ND-10885
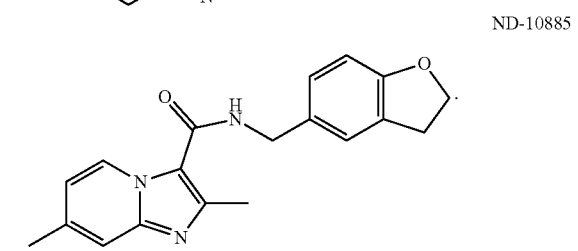

2. A composition, comprising the compound of claim 1 and a physiologically acceptable carrier.

3. A method, comprising administering the compound of claim 1 or the composition of claim 2 to a subject known or suspected to need treatment for one or more maladies related to non-pathogenic mycobacterial strain, M. smegmatis, M. vaccae, M. aurum, Gram positive bacteria, S. aureus, M. luteus, M. intracellulare, M. Gram negative bacteria, P. aeruginosa, A. baumanii, pathogenic mycobacterial strain, M. tuberculosis, M. bovis, M. marinum, M. kansasaii, H37Rv, M. africanum, M. canetti, M. caprae, M. microti, M. mungi, M. pinnipedii, M. avium, myobacterium tuberculosis complex, tuberculosis, or combination thereof, to treat said subject.

4. The compound of claim 1, having the following formula:

ND-011544
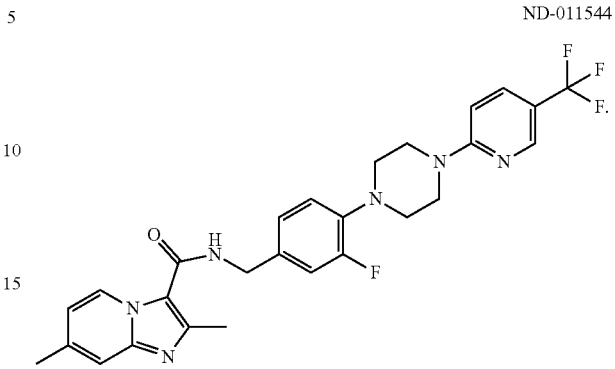

5. The compound of claim 1, having the following formula:

ND-011598
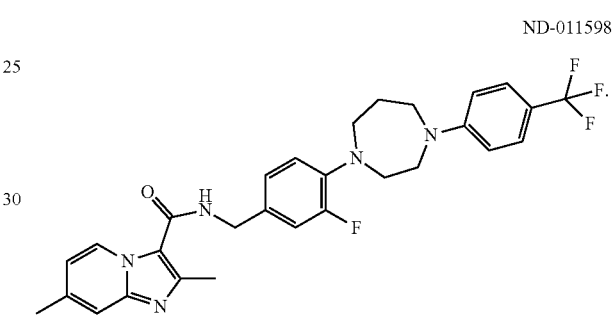

6. The compound of claim 1, having the following formula:

ND-011622
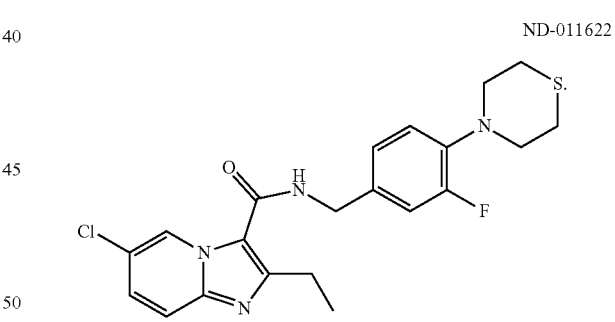

7. The compound of claim 1, having the following formula:

ND-10885
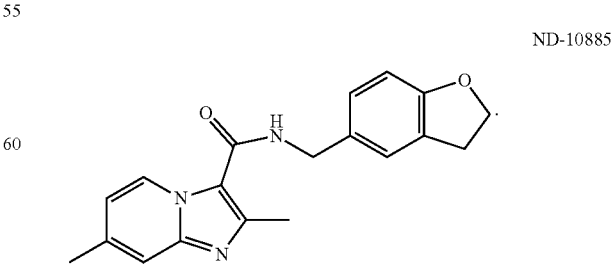

* * * * *